(12) United States Patent
Raymond et al.

(10) Patent No.: US 7,718,781 B2
(45) Date of Patent: May 18, 2010

(54) HYDROXYPYRIDONATE AND HYDROXYPYRIMIDINONE CHELATING AGENTS

(75) Inventors: Kenneth N. Raymond, Berkeley, CA (US); Daniel M. J. Doble, Tigard, OR (US); Christopher J. Sunderland, Menlo Park, CA (US); Marlon Thompson, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 884 days.

(21) Appl. No.: 10/902,772

(22) Filed: Jul. 30, 2004

(65) Prior Publication Data

US 2005/0008570 A1 Jan. 13, 2005

Related U.S. Application Data

(63) Continuation of application No. 10/194,502, filed on Jul. 12, 2002, now Pat. No. 6,846,915, and a continuation of application No. PCT/US02/26026, filed on Aug. 13, 2002.

(60) Provisional application No. 60/312,132, filed on Aug. 13, 2001.

(51) Int. Cl.
C07F 5/00 (2006.01)
(52) U.S. Cl. ............... 534/15; 424/1.11; 424/1.65; 544/180; 544/224; 549/200
(58) Field of Classification Search .......... 424/1.11, 424/1.65, 9.1, 1.37; 534/7, 10–16; 544/224, 544/180; 549/200
See application file for complete search history.

(56) References Cited

U.S. PATENT DOCUMENTS

| | | | | |
|---|---|---|---|---|
| 4,181,654 A | 1/1980 | Weitl | | 260/999.999 |
| 4,309,305 A | 1/1982 | Weitl | | 252/999.999 |
| 4,442,305 A | 4/1984 | Weitl | | 562/451 |
| 4,543,213 A | 9/1985 | Weitl | | 260/239 |
| 4,666,927 A | 5/1987 | Hider | | 514/350 |
| 4,698,431 A | 10/1987 | Raymond | | 546/262 |
| 4,939,254 A | 7/1990 | McMurry | | 540/452 |
| 5,010,191 A | 4/1991 | Englstad | | 544/225 |
| 5,049,280 A | 9/1991 | Raymond | | 210/638 |
| 5,624,901 A | 4/1997 | Raymond | | 514/17 |
| 5,892,029 A * | 4/1999 | Raymond et al. | | 540/474 |
| 6,406,297 B1 * | 6/2002 | Raymond et al. | | 434/15 |
| 6,515,113 B2 * | 2/2003 | Raymond et al. | | 534/15 |
| 6,846,915 B2 * | 1/2005 | Raymond et al. | | 534/15 |
| 6,864,103 B2 * | 3/2005 | Raymond et al. | | 436/546 |

OTHER PUBLICATIONS

Southwood-Jones et al (Journal of Chemical Physics, 1980, vol. 73, No. 12, pp. 5909-5918).*
Aime et al (European Journal of Inorganic Chemistry, 1998, vol. 9, pp. 1283-1289).*
Cohen et al (Inorganic Chemistry, 2000, vol. 39, pp. 5747-5756).*
Alessandra Villa, et al., "Force Field Parametrization for Gadolinium Complexes Based on ab Initio Potential Energy Surface Calculations," J. Phys. Chem. A, 104:3421-3429 (2000).
Cohen et al., "Syntheses and Relaxation Properties of Mixed Gadolinium Hydroxypyridinonate MRI Contrast Agents", Inorg. Chem., Nov. 17, 2000, vol. 39, pp. 5747-5756.
Cohen, S.M. et al. "Syntheses and relaxation properties of mixed gadolinium hydroxypyridinonate MRI contrast agents," Inorg. Chem. 39, 5747-5756, 2000.
Hajela, S. et al., "A tris-hydroxymethyl-substituted derivative of Gd-TREN-Me-3,2-HOPO: An MRI relaxation agent with imroved efficiency," J. am. Chem. Soc., 122, p. 11228-11229, 2000.
Hajela, S.P., et al., "Synthesis of homochiral tris(2-alkyl-2-aminoethyl) amine derivatives from chiral a-amino aldehydes and their application in the synthesis of water soluble chelators," lnorg. Chem., 40, p. 3208-3216, May 16, 2001.
Unger, E.C. et al., "Gadolinium-containing copolymeric chelates-a new potential MR contrast agent," Magnetic Resonance Materials in Physics, Biology and Medicine, p. 154-162, 1998.
Frank, H. et al., "Detection of pulmonary emboli by using MR angiography with MPEG-PL-GdDTPA: an experimental study in rabbits," American J. of Roentgenology, v. 162, n. 5, p. 1041-1046, 1994.
Bryant, L.H. et. al. "Synthesis and relaxometry of high-generation {G=5, 7, 9, and 10} PAMAM dendrimer-DOTA-gadolinium chelates," J. Magnetic Resonance Imaging, v. 9, n. 2, p. 348-352, 1999.
Vander Elst, L., et al., "Stereospecific binding of MRI contrast agents to human serum albumin: the case of Gd-(S)- EOB-DTPA (Eovist) and its (R) isomer," J. Biol. lnorg. Chem., 6, p. 196-200, Jan. 17, 2001.
Curtet, C. et al., "In Vivo diagnosis and therapy of human tumors with monoclonal antibodies," Int. J. of Radiation Applications and Instrumentation Part B, v. part b/16, n. 2, p. 180, 1989.
Xu, S. et al., "Gadolinium complex of tris[(3-hydroxy-1-methyl-2-oxo-1,2-didehydropyridine-4-carboxamido)ethyl]-amine: A new class of gadolinium magnetic resonance relaxation agents," J. Am. Chem. Soc., 117, p. 7245-7246, 1995.
Johnson, A.R., et al., "Sunthesis of a ligand based upon a new entry into the 3-hydroxy-N-alkyl- 2(1H0-pyridinone ring system and thermodynamic evaluation of its gadolinium complex," Inorg. Chem., v. 39, p. 2652-2660, 2000.

* cited by examiner

*Primary Examiner*—D L Jones
(74) *Attorney, Agent, or Firm*—Morgan, Lewis & Bockius LLP; Jeffry S. Mann

(57) ABSTRACT

The present invention provides hydroxypyridinone and hydroxypyrimidone chelating agents. Also provides are Gd(III) complexes of these agents, which are useful as contrast enhancing agents for magnetic resonance imaging. The invention also provides methods of preparing the compounds of the invention, as well as methods of using the compounds in magnetic resonance imaging applications.

9 Claims, 23 Drawing Sheets

Small molecules that interact with HSA

- Drug-protein interactions are dominated by hydrophobic contacts
- Electrostatic interactions also play an important role
- Complementarity between the shape of the pocket and the drug is important

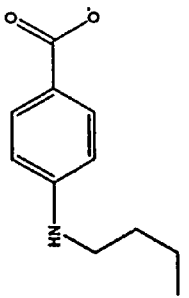
n-butyl-p-aminobenzoate - Site I

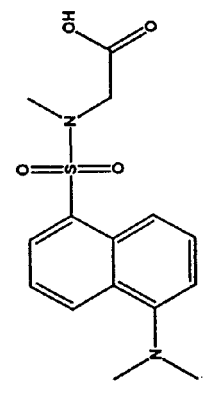
Dansylsarcosine - Site I

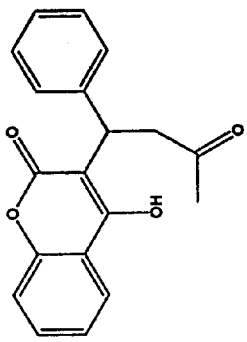
Warfarin - Site I

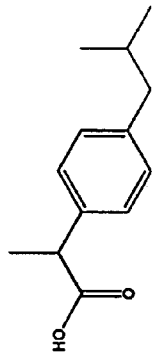
Ibuprofen - Site II

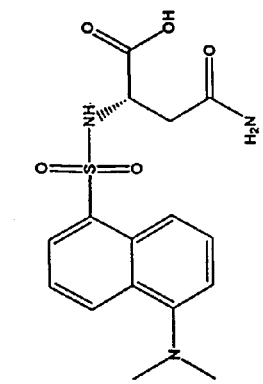
Dansyl-L-asparagine - Site II

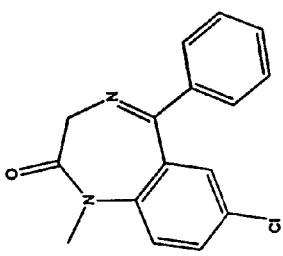
Diazepam (Valium) - Site II

FIG. 11

| Ligand | pGd | pCa | pZn |
|---|---|---|---|
| TREN-1-Me-HOPO | 19.2 | 7.6 | 13.1 |
| TREN-6-Me-HOPO | 19.5 | 6.8 | 11.4 |
| TREN-MOE-HOPO | 19.8 | - | - |
| SerTREN-1-Me-HOPO | 17.7 | - | - |
| TREN-HOPY | 18.0 | - | - |
| TREN-bis(6-Me-HOPO)-(TAM-TRI) | 22.6 | - | - |
| TREN-bis(1-Me-HOPO)-(TAM-EA) | 23.3 | 6.0 | 12.3 |
| TREN-bis(1-Me-HOPO)-(TAM-Me) | 23.7 | - | - |
| DTPA | 19.2 | 7.5 | 15.5 |
| DTPA-BMA | 15.8 | 6.4 | 11.0 |
| DOTA | 19.4 | 10.5 | 13.6 |

HOPO = 3,2-HOPO pM = -log[M]$_{free}$; [M]$_{total}$ = 1 μM, [ligand]$_{total}$ = 10 μM, pH 7.4 (25° C, 0.1 M KCl)

FIG. 23

HYDROXYPYRIDONATE AND HYDROXYPYRIMIDINONE CHELATING AGENTS

CROSS-REFERENCE TO RELATED APPLICATIONS

This application is a continuation application of U.S. patent application Ser. No. 10/194,502, filed Jul. 12, 2002 and issued as U.S. Pat. No. 6,846,915; and claims the benefit under 35 USC 119(e) to U.S. Provisional Patent Application No. 60/312,132, filed Aug. 13, 2001, and to International Patent Application No. PCT/US2002/026026, filed Aug. 13, 2002, all of which are incorporated by reference in their entirety for all purposes.

BACKGROUND OF THE INVENTION

It was first shown in 1972 that by superimposing linear field gradients to the static magnetic field of a nuclear magnetic resonance (NMR) experiment it is possible to obtain three-dimensional images of an object (Lauterbur, P. C., *Nature* 1973, 190). The new technique became known as magnetic resonance imaging (MRI). MRI has developed impressively, becoming one of the most powerful tools "to look inside matter" (Aime, S. B. et al., E. *Acc. Chem. Res.* 1999, 32, 941). As X-ray imaging did in the beginning of the 20th century, magnetic resonance imaging (MRI) has revolutionized modern diagnostic medicine (Caravan, P. E. et al., *Chem. Rev.* 1999, 99, 2293). Whereas conventional X-rays show skeletal structure, MRI enables the acquisition of high resolution, three-dimensional images of the distribution of water in vivo. This powerful diagnostic tool is invaluable in the detection of a wide variety of physiological abnormalities including tumors, lesions, and thromboses. Additionally, recent advances in dynamic MRI open up the exciting possibility of real-time imaging of biochemical activity ("A New Generation of In Vivo Diagnostics," MetaProbe, 2000).

The medical utility of MRI is enhanced through the administration of contrast agents prior to the scan, which alters the relaxation times of protons in the vicinity of the agent, increasing the degree of contrast between healthy and diseased tissue. The use of contrast agents is increasingly popular in medical protocols, with some 30-35% of MRI scans now acquired with the aid of a contrast agent (Caravan, P. E. et al., *Chem. Rev.* 1999, 99, 2293; Aime, S. B. et al., E. *Acc. Chem. Res.* 1999, 32, 941). Consequently, contrast agents now represent a very large market, with sales of over $250 million in 2000 ("RC-211, Contrast Agents for Medical Imaging," Business Communications Company, Inc., 1999).

Several new contrast agents are currently under development, which are designed to be more site-specific, facilitating, for example, detailed images of cardiovascular features (Lauffer, R. B., Magn. Reson. Med. 1991, 22, 339). Additionally, recent reports have demonstrated that contrast agents can detect the presence of enzymes and metal cations (Moats, R. A. F. et al., *Angew Chem., Int. Ed. Engl* 1997, 36, 726; Li, W. F. et al., *J. Am. Chem. Soc.* 1999, 121, 1413).

At present, clinically accepted contrast agents are based upon a gadolinium complex of a poly(aminocarboxylate) ligand, e.g., the gadolinium chelates of DTPA, DOTA, DO3A and DTPA-BMA (FIG. 1). The agents are extracellular agents that distribute non-specifically throughout the plasma and interstitial space of the body. A typical use of such agents is in the detection of tumors in the brain.

The image enhancing capability of available agents is far lower than the optimal values predicted by theory (Aime, S. B. et al., *Coord. Chem. Rev.,* 321: 185-6 (1999)). The relatively low image enhancing properties of current contrast agents requires injection of gram quantities in order to obtain satisfactory contrast in the resulting image. With such large doses required for reasonable image enhancement, present contrast agents are limited to targeting sites where they can be expected to accumulate in high concentrations. To accomplish greater resolution with lower dose and to enable a variety of target-selective imaging (such as hepatobiliary features), there is a need for contrast agents of increased image enhancement capacity and corresponding enhanced water proton relaxivity. Moreover, a useful complex must be highly water soluble, resistant to in vivo dissociation of the metal ion from the chelate and of acceptably low toxicity. A promising new class metal-binding ligands are based upon the heterocyclic pyridinone and pyrimidinone nuclei.

Distinct in both structure and properties from poly(aminocarboxylate) chelate-based MRI contrast agents is a class of compounds that include one or more hydroxypyridinone or hydroxypyrimidinone subunit. Both homopodal and heteropodal chelating agents incorporating a hydroxypyridinone or hydroxypyrimidinone moiety are known in the art. Although many of the reported compounds exhibit the desirable water exchange kinetics and complex stability characteristic of this class of compounds, the reported water solubilities of the Gd(III) complexes are generally insufficient to allow the complexes to be considered as candidate MRI contrast enhancing agents.

For example, Xu et al. (*J. Am. Chem. Soc.,* 117: 7245-7246 (1995) reported the synthesis and characterization of Gd(III) TREN-Me-3,2-HOPO (tris((3-hydroxy-1-methyl-2-oxo-1, 2-didehydropyridine-4-carboxamido)ethyl)amine)). The solubility of the disclosed complex in water is only about 0.1 mM, making it less than ideal as a MRI contrast enhancing pharmaceutical.

Furthermore, Cohen et al. (*Inorg. Chem.,* 39: 5747-5746 (2000)) prepared a series of mixed ligand systems that are based on the TREN-Me-3,2-HOPO platform. The ligands include two HOPO chelators and a non-HOPO chelator. The ligands set forth in Cohen et al. incorporate salicylamide, 2-hydroxyisophthalamide, 2,3-dihydroxyterephthalamide and bis(acetate) as the non-HOPO chelators. The Gd(III) complexes of the ligands according to the disclosed motif were of moderate water solubility (approx. 1-3 mM).

Hajela et al. (*J. Am. Chem. Soc.* 122: 11228-11229 (2000)) prepared a homopodal Me-3,2-HOPO chelate based on a functionalized TREN backbone. The functionalized TREN backbone was a homochiral tris(2-hydroxymethyl)-TREN-Me-3,2-HOPO. The Gd(III) complex of the ligand has a water solubility of approximately 15 mM.

HOPO ligands in which the endocyclic nitrogen of the pyridinone moiety is functionalized are known. For example, the ligand TREN-MOE-3,2-HOPO (tris(3-hydroxy-1-methoxyethyl)-2-oxo-1,2-didehydropyridine-4-carboxamido) ethyl)amine) and its Gd(III) complex was prepared and characterized by Johnson et al. (*Inorg. Chem.* 39: 2652-2660 (2000)). The complex was reported to have a water solubility of about 1 mM.

In addition to those references discussed above, U.S. Pat. No. 5,049,280 discloses homopodal chelating agents based on the 2,3-dihydroxyterephthalamide moiety. The '280 patent does not disclose or suggest combining the disclosed moiety with a HOPO or HOPY subunit to form a heteropodal chelating agent. U.S. Pat. No. 4,698,431 discloses chelating agents having 1-hydroxy-2-pyridinone subunits. The complexes are disclosed to exhibit a high affinity for iron ions and actinides such as Pu(IV). Neither the '280 nor the '431 patent suggest the use of the novel chelates to complex Gd(III).

U.S. Pat. No. 5,892,029 and 5,624,901 set forth a class of homo- and heteropodal chelate systems having at least one 3,2-HOPO subunit within their structure. Neither the '029 nor the '901 patent suggest that the disclosed ligands are of use in forming a highly water soluble Gd(III) chelate.

Other related art includes U.S. Pat. No. 4,666,927, which discloses a number of chelating agents having 1,2-HOPO, 3,2-HOPO, or 3,4-HOPO moieties incorporated within their structures that are linked through a number of possible combinations of linking groups, including —CONH— groups. However, U.S. Pat. No. 4,666,927 teaches against a HOPO moiety having a substitution ortho to the hydroxy or oxo group of the HOPO ring. U.S. Pat. No. 6,221,476 discloses polyhydroxypyridinone ligands that are attached to a membrane support. The compositions are useful for removing metal ions from solutions. Zbinden (U.S. Pat. No. 5,688,815) sets forth a class of 3-hydroxypyridin-4-ones, which are effective chelators of iron and useful to treat iron overload. Neither the '927 nor the '476 teach one of skill in the art how to prepare a highly water soluble Gd(III) chelate that is of use as a contrast enhancing pharmaceutical.

As discussed above, Gd(III) chelates of hydroxypyrimidinone and hydroxypyridinone ligands have a number of properties that make them superior MRI contrast agents relative to the widely used Gd(III)-poly(aminocarboxylate) agents. The development of the new contrast media based on the pyrimidinone and pyridinone ring systems has, however, been hampered by the inadequate water solubility of such agents. A new generation of Gd(III) complexes based upon the heterocyclic ring systems would represent a significant advance in the field of MRI contrast enhancement. Quite surprisingly, the present invention provides such complexes.

BRIEF SUMMARY OF THE INVENTION

Metal chelates and chelating agents are pharmaceutical agents that are useful in both diagnostic and therapeutic applications. The present invention is directed to a new class of highly water-soluble paramagnetic metal chelates of use as contrast agents in medical imaging modalities, such as magnetic resonance imaging (MRI). The paramagnetic chelates of the invention have unexpectedly high water exchange rates, and correspondingly high proton relaxation rates, making them highly effective MRI contrast agents. Moreover, the synthetic pathways to the chelates of the invention provide for the facile incorporation of subunits that modify one or more properties of the chelates. Thus, there are provided chelates that include water-soluble groups, targeting groups, chelates conjugated to diverse macromolecules and the like.

The present invention provides a new class of highly water soluble Gd(III) complexes that also exhibit excellent stability and resistance to dissociation in vivo. Moreover, the Gd(III) complexes have surprisingly rapid water exchange kinetics, giving the compounds potent relaxivity. Thus, the invention provides complexes that are water soluble, powerful, and non-toxic proton relaxation agents.

The present invention provides thermodynamically stable Gd(III) complexes of HOPO ligands that have relaxivities approximately twice those of commercial agents such as Gd[DOTA] and Gd[DTPA]. The stability of the Gd complexes is also reflected in the preference of the ligands for Gd(III) in the presence of other metal ions. Moreover, selected compounds of the invention have relaxivities that are at least about twice those of commercial agents. In addition complexes provided by the present invention have near optimal water exchange rates, which are about 100 times greater than existing agents.

Thus, in a first aspect, the present invention provides a complex between a Gd(III) ion and an organic ligand comprising only oxygen donor atoms coordinating the Gd(III) ion. The complexed gadolinium ion has a water exchange rate of at least about $10 \times 10^6$ sec$^{-1}$. The solubility in water of the complex is at least about 15 mM, preferably, at least about 20 mM.

In a second aspect the invention provides an aqueous solution of a compound of the invention. The aqueous solution includes a complex between a gadolinium (III) ion and an organic ligand comprising only oxygen donor atoms coordinating the gadolinium (III) ion. The solution has a pM of at least about 15. The solution is about pH 7.4, and includes about 10 μM of the ligand and about 1 μM of Gd(III). The complex has a solubility in water of at least about 15 mM, more preferably, at least about 20 mM.

In a third aspect, the invention provides a complex between a gadolinium (III) ion and an organic ligand. The ligand includes the structure according to Formula I:

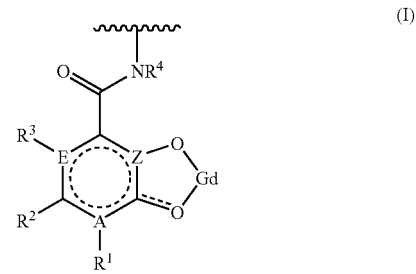

in which, the symbols $R^1$, $R^2$, and $R^3$ are independently selected from a linking member, an aryl group substituent, H, substituted or unsubstituted alkyl, substituted or unsubstituted aryl, substituted or unsubstituted heteroalkyl, hydroxy, carboxy, amide, ester, amine, and reactive functional groups, with the proviso that when A is nitrogen, $R^1$ is other than amino, and with the further proviso that when E is nitrogen, $R^3$ is not present. The symbol $R^4$ represents a linking member, H, substituted or unsubstituted alkyl, substituted or unsubstituted heteroalkyl, substituted or unsubstituted aryl, hydroxy, carboxy, amide, or an ester group. A, E and Z are independently selected from carbon and nitrogen. The gadolinium complex preferably has a solubility in water of at least about 15 mM, more preferably, at least about 20 mM.

Also provided is a method of performing contrast-enhanced magnetic resonance imaging on a patient. The method includes administering to the patient an amount of a compound of the invention sufficient to provide contrast enhancement, and acquiring a contrast enhanced MR image.

The invention also provides selective structural modifications of the ligand scaffold result in in vivo residence times that are enhanced relevant to analogous compounds that are not modified. Other modifications are provided that generate greater specificity in the in vivo distribution of the modified $Gd^{3+}$ complexes.

Other objects and advantages of the invention will be apparent to those of skill in the art from the detailed description that follows.

BRIEF DESCRIPTION OF THE DRAWINGS

FIG. 11 provides exemplary structures that are known to interact with human serum albumin.

FIG. 23 displays the pGd, pCa and pZn values for various complexes of the invention.

DETAILED DESCRIPTION OF THE INVENTION

1. Introduction

Figure 1:
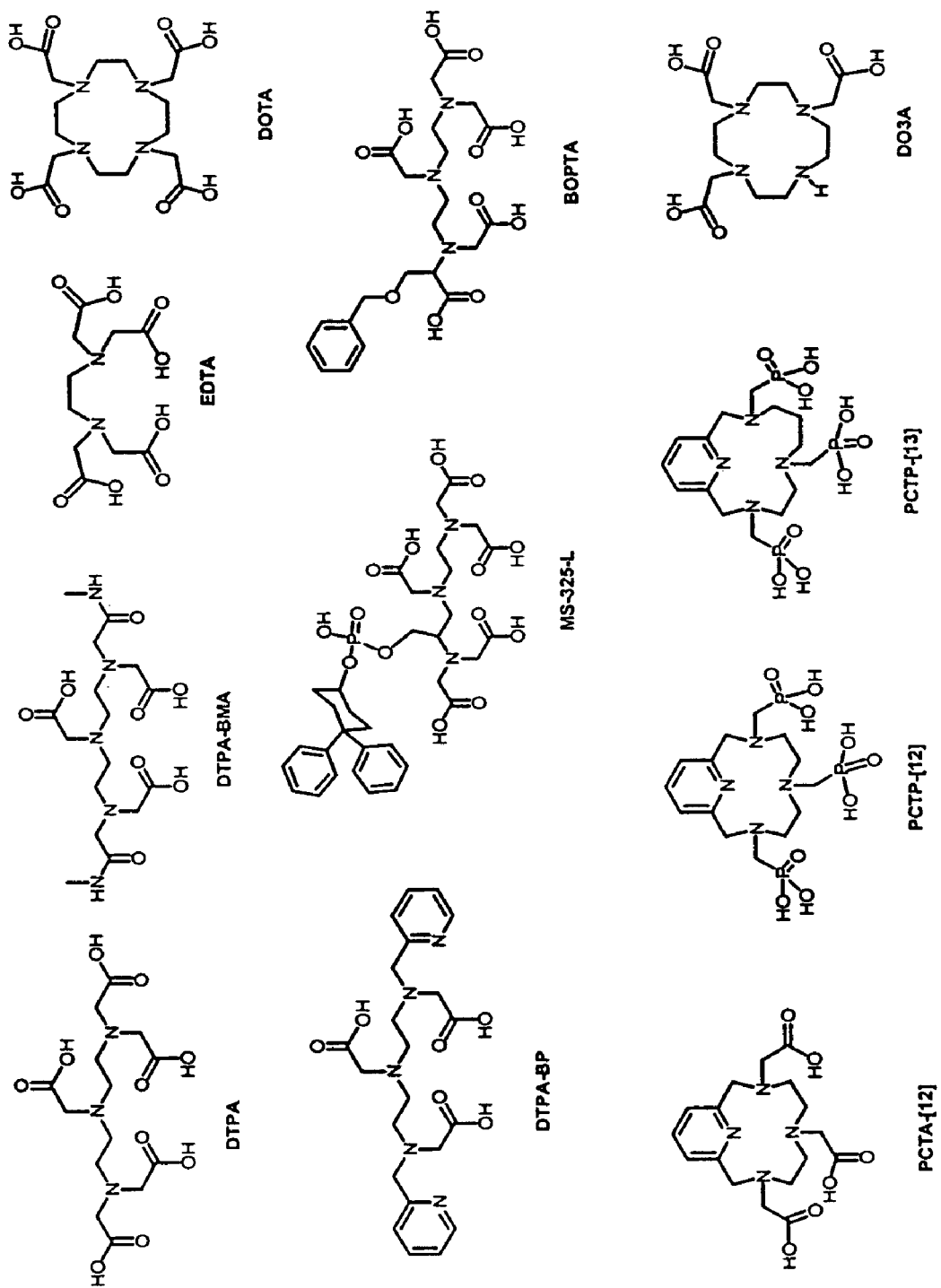
FIG. 1 is a collection of poly(amino-carboxylate) ligands used for chelating Gd(III).

The present invention provides chelating agents that are useful for many purposes including, but not limited to, contrast agents for imaging modalities (e.g., MRI, CT), metal ion decorporation (e.g., iron, actinides), and the like. The chelating agents are also of use for binding radioisotopes utilized in nuclear medicine, gamma camera scintigraphy, and other medical applications. There is also provided an array of metal complexes formed between the chelates of the invention and many metal ions. The chelating agents form surprisingly stable, highly water-soluble complexes with metal ions.

1.1 Definitions

The term, "pGd," as used herein is $-\log_{10}[Gd^{III}]_{free}$ at pH=7.4, and pre-equilibrium concentrations of [L]=10 μM, [Gd$^{III}$]=1 μM.

"HOPO," as used herein refers to hydroxypyridonate.

The term "HOPY," refers to hydroxypyrimidinone.

The term "TAM," refers to dihydroxyterephthalamide.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitrites, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

"Non-covalent protein binding groups" are moieties that interact with an intact or denatured polypeptide in an associative manner. The interaction may be either reversible or irreversible in a biological milieu. The incorporation of a "non-covalent protein binding group" into a chelating agent or complex of the invention provides the agent or complex with the ability to interact with a polypeptide in a non-covalent manner. Exemplary non-covalent interactions include hydrophobic-hydrophobic and electrostatic interactions. Exemplary "non-covalent protein binding groups" include anionic groups, e.g., phosphate, thiophosphate, phosphonate, carboxylate, boronate, sulfate, sulfone, thiosulfate, and thiosulfonate.

As used herein, "linking member" refers to a covalent chemical bond that includes at least one heteroatom. Exemplary linking members include —C(O)NH—, —C(O)O—, —NH—, —S—, —O—, and the like.

The term "targeting group" is intended to mean a moiety that is: (1) able to actively direct the entity to which it is attached (e.g., contrast agent) to a target region, e.g., a tumor; or (2) is preferentially passively absorbed by or entrained within a target tissue, for example a tumor. The targeting group can be a small molecule, which is intended to include both non-peptides and peptides. The targeting group can also be a macromolecule, which includes, but is not limited to, saccharides, lectins, receptors, ligand for receptors, proteins such as BSA, antibodies, poly(ethers), dendrimers, poly (amino acids) and so forth.

The term "cleavable group" is intended to mean a moiety that allows for release of the chelate from the rest of the conjugate by cleaving a bond linking the chelate (or chelate linker arm construct) to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable sites, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and hetero-bifunctional) spacer arms are commercially available from suppliers such as Pierce.

The symbol ~~, whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1) where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R"', —OC(O)R', —C(O)R', —CO$_2$R', —CONR'R—, —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "heteroatom" is meant to include oxygen (O), nitrogen (N), sulfur (S) and silicon (Si).

A "MRI signal generating moiety" is a species that affects T1 or T2 of water molecules in a sample or subject undergoing a MRI experiment.

The broken line as a component of a chemical structure implies that the position of the bond may be varied, such as within a ring structure, or that the bond may be either present or absent, such that the principles of chemical valency are obeyed.

Chelating Agents as MRI Contrast Agents

The image intensity in MRI, largely composed of the NMR signal of water protons ($^1$H), is the result of a complex interplay of numerous factors. These include the longitudinal (T$_1$) and transverse (T$_2$) proton relaxation times, proton density of the imaged tissues and instrumental parameters (such as magnetic field strength) (Aime, S. B. et al., *Coord. Chem. Rev.* 1999, 185-6, 321). Contrast agents (complexes of paramagnetic ions) decrease the relaxation times of nearby water protons by dipolar interactions, resulting in enhanced signal intensity of the tissue containing the agent (Lauffer, R. B., *Chem. Rev.* 1987, 87, 901). The high magnetic moment and relatively long electronic relaxation time of Gd(III) make it ideally suited as the active component in MRI contrast agents (Banci, L. B. et al., *C. Nuclear and Electronic Relaxation*; VCH: Weinheim, 1991). Images that are acquired with the aid of a Gd(III) contrast agent are preferably visualized as "Ti-weighted images" since the percentage change in 1/T$_1$, in tissue is much greater than that in 1/T$_2$ (Caravan, P. E. et al., *Chem. Rev.* 1999, 99, 2293).

In one aspect, the present invention relates to novel MRI contrast agents and compositions of novel MRI contrasting agents with faster water exchange rates (i.e. with $\tau_m$ and $\tau_r$ preferably in the low ns regime) and desirable in vivo persistence. These novel agents facilitate diagnosis of physiological abnormalities in specific regions of the body over longer time periods than are currently possible.

Although the discussion below focuses on gadolinium as a representative paramagnetic ion that is coordinated by the chelating agents of the invention, it will be apparent to those of skill in the art that the chelating agents of the invention are appropriate for complexing many metal ions. Thus, it is within the scope of the present invention to utilize ions of, e.g., transition metals, and lanthanides other than gadolinium. Exemplary metal ions include the ions of Dy, Fe, Mn, Pu, and U.

For a metal chelate to be useful as a contrast enhancing agent in MRI, the agent must satisfy several requirements. Broadly stated the three most important requirements are stability, relaxivity and water solubility, each of which must high values. The inventors have recognized that ligand systems that have only oxygen donor atoms provide complexes of Gd(III) that exhibit excellent stability, have high relaxivity and are highly water soluble. Each of the essential characteristics of a useful complex between Gd(III) and a ligand with only oxygen donor atoms is discussed below.

Water Solubility

As with most diagnostic agents, it is desired that a MRI contrast enhancing agent be as highly water soluble as possible. The water solubility of MRI contrast agents is of particular importance because the agents are administered in multigram dosages to the subject of the imaging experiment. A highly water-soluble agent requires a lower injection volume for administration. Lower injection volume correlates with ease of agent administration and decreased patient discomfort.

The inventors have recognized that for a complex of Gd(III) with a ligand having only oxygen donor atoms to be a promising candidate for a MRI contrast agent, the complex preferably has a water solubility of at least about 15 mM and, more preferably, at least about 20 mM. The present invention provides complexes between Gd(III) and ligands with only oxygen donors that meet and/or exceed this requirement. The invention provides Gd(III) complexes as described above, having water solubilities of from about 50 mM to about 300 mM and, preferably from about 100 mM to about 1 M.

In contrast to the compounds of the present invention, the compounds known in the art are relatively water insoluble. For example, TREN-MOE-3,2-HOPO has a water solubility at pH 7.4 of about 1 mM. In contrast, a compound of the present invention such as the Gd(III) complex of TREN-HOPY has a relaxivity of at least about 100 mM. Moreover, the present invention provides poly(ether) conjugates of homopodal and heteropodal ligands having water solubilities that are dramatically improved over compounds reported to date. Exemplary solubilities of compounds of the invention and known compounds are compared below in Table 1.

TABLE 1

| Complex | Water Solubility (pH 7, 25° C.) |
| --- | --- |
| Gd-TREN-HOPO (7) | 0.1 mM |
| Gd-TREN-HOPO-MOE | 1 mM |
| Gd-TRENGly-HOPO (7A) | 0.24 mM ($\epsilon$ = 21,000 lmol$^{-1}$cm$^{-1}$) |
| Gd-TREN-HOPY | 100 mM |
| Gd-TREN-bisHOPO-(TAM-Me) | <3 mM |
| Gd-SerTREN-HOPO | 15 mM |
| Gd-TREN-bisHOPO-(TAM-PEG5000) (47) | 300 mM* |
| Gd-TREN-bis(HOPO-Bn)-(TAM-PEG550) (55) | 26.8 mM* ($\epsilon$ = 17,443 lmol$^{-1}$cm$^{-1}$) |
| Gd-TREN-bisHOPO-(TAM-PEG450) (48) | 48.3 mM* ($\epsilon$ = 17,620 lmol$^{-1}$cm$^{-1}$) |
| Gd-TREN-bisHOPO- | 20.1 mM* ($\epsilon$ = 17,641 lmol$^{-1}$cm$^{-1}$) |

HOPO = 1-Me-3,2-HOPO or 6-Me-3,2-HOPO
*minimum solubility in H$_2$O (0.01 M HEPES).

Relaxivity

Figure 2:
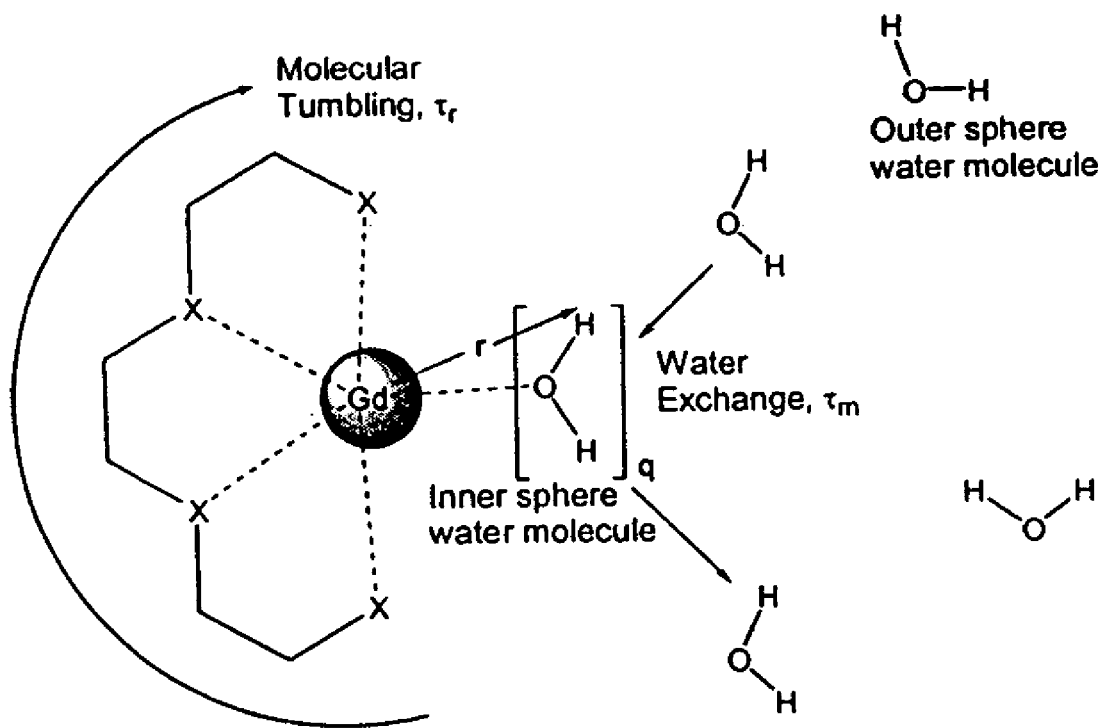
FIG. 2 is a diagram of a Gd(III) complex showing inner and outer-sphere water molecules, and the parameters that affect inner-sphere relaxivity.

The potency of a MRI contrast agent is generally given in terms of the magnitude of its relaxivity. The relaxivity, $r_1$, of a MRI contrast agent, as used herein, refers to the amount of increase in $1/T_1$ signal intensity that occurs per millimolar of Gd(III). When considering the interactions of water molecules with the contrast agent on the atomic scale, the relaxivity can be sub-divided into inner sphere and outer sphere contributions (FIG. 2) (Lauffer, R. B., *Chem. Rev.* 1987, 87, 901).

Figure 3:
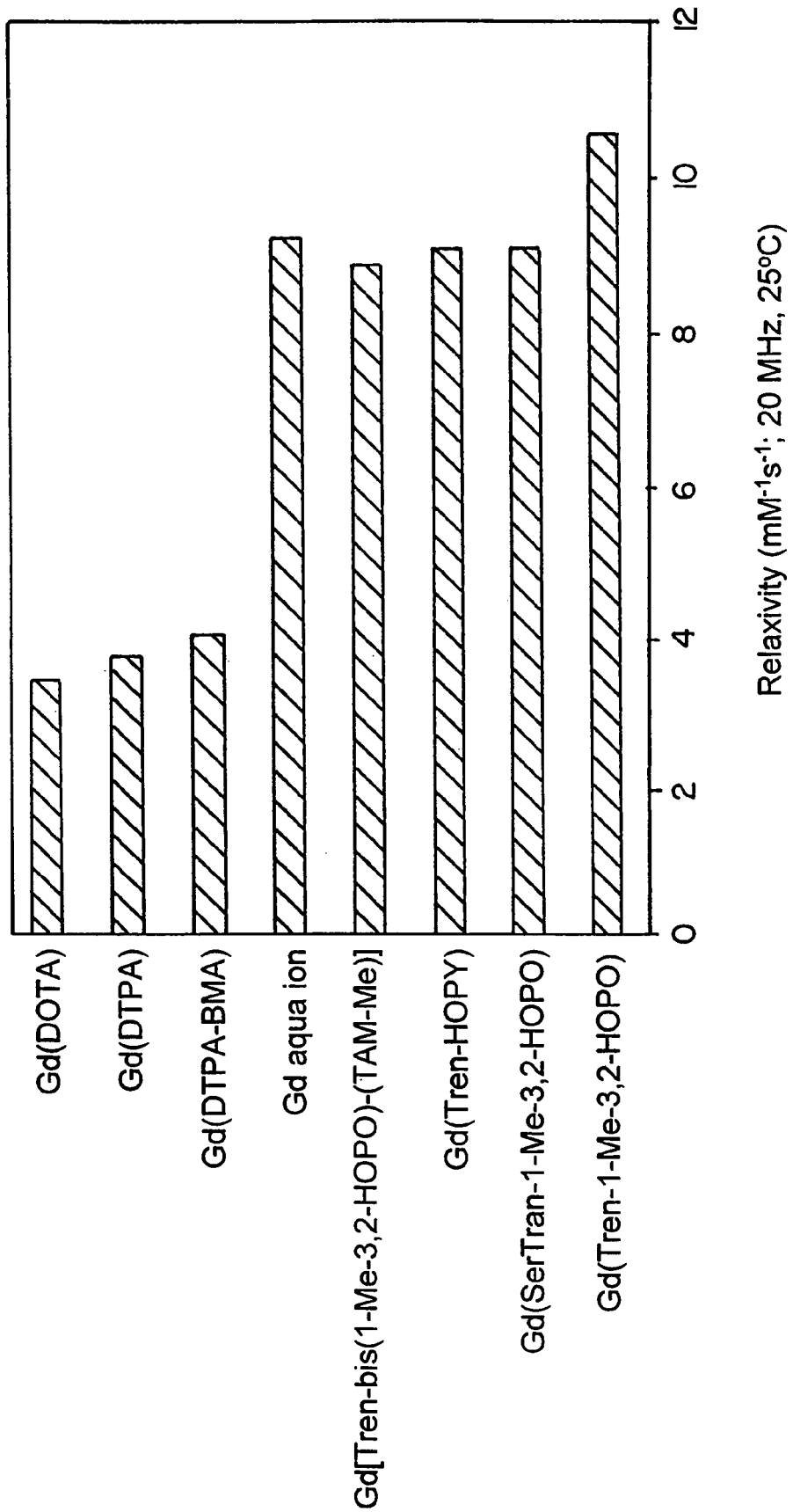
FIG. 3 is a graphical presentation comparing relaxivity data for compounds of the invention and Gd(III)-polyaminocarboxylates.

A mechanism underlying the enhanced relaxivity of the complexes of the invention is the near ideal time-scale of the water exchange kinetics of the complexes. The inventors have recognized that for a complex formed between a Gd(III) ion and a ligand with only oxygen donor atoms to be a candidate MR imaging agent candidate, the metal ion of the complex preferably has a water exchange rate of at least about $10 \times 10^6$ sec$^{-1}$ (FIG. 3).

While the clinically approved gadolinium(III) chelates are all octadentate with one coordinated water molecule (q=1) (Caravan, P. E. et al., *Chem. Rev.* 1999, 99, 2293), hexadentate tripodal hydroxypyridonate complexes such as TREN-1-Me-HOPO form stable, di-aquo complexes with Gd$^{3+}$ (q=2) (Xu, J. et al., *J. Am. Chem. Soc.* 1995, 117, 7245; Johnson, A. R. et al., *Inorg. Chem.* 2000, 39, 2652-2660). The relaxivity of the complexes of the invention is typically at least two-fold greater than that of agents based upon the polyaminocarboxylate motif (FIG. 3).

Figure 4:
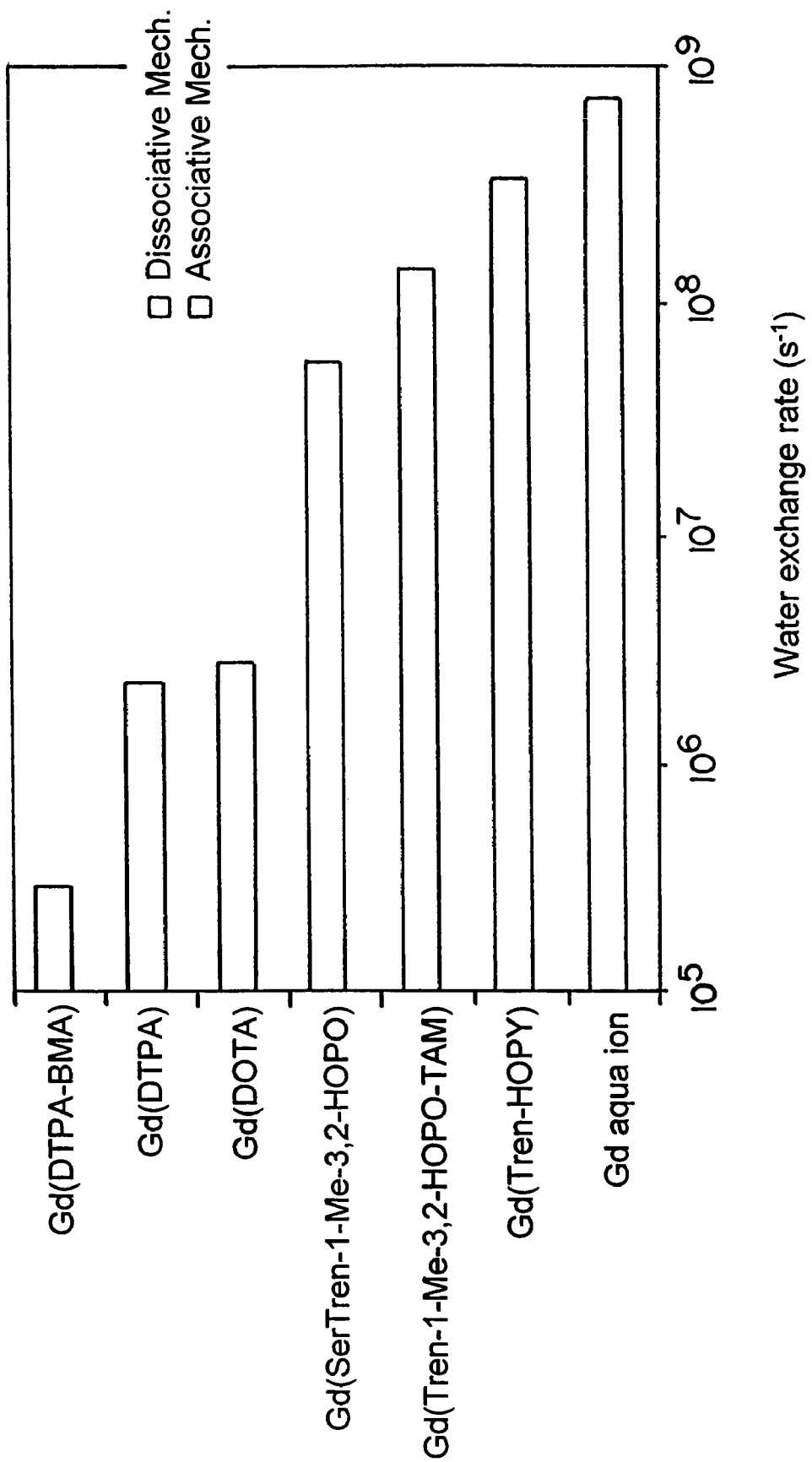
FIG. 4 is a graphical presentation comparing water exchange rates for compounds of the invention and Gd(III)-polyaminocarboxylates.

For example, the relaxivity ($r_1$) of TREN-1-Me-HOPO at 37° C. and 20 MHz is 10.5 mM$^{-1}$s$^{-1}$, some 2.5 times that of [Gd(DTPA)(H$_2$O)]. This is partly due to the higher number of coordinated water molecules (q=2) as well as the increased molecular weight (which results in a longer rotational correlation time, $\tau_r$). Another factor that enhances the relaxivity of the complexes of the invention relative to the polyaminocarboxylates is the nearly ideal time-scale of the water exchange kinetics of the present complexes (FIG. 4). Another advantageous feature of TREN-1-Me-HOPO for clinical applications is its neutrality, which reduces osmolality effects in vivo, therefore lessening the discomfort of patients upon its intravenous administration (Lauffer, R. B., *Chem. Rev.* 1987, 87, 901).

The relaxivity in water of the complexes of the invention is preferably greater than about 5 mM$^{-1}$s$^{-1}$, more preferably greater than about 6 mM$^{-1}$s$^{-1}$. A presently preferred range of relaxivities of compounds of the invention is from about 6 mM$^{-1}$s$^{-1}$ to about 15 mM$^{-1}$s$^{-1}$.

Stability

Since free Gd(III) is toxic it must be bound by a multidentate ligand to form a complex of high stability before it can be safely administered to patients. Several groups have investigated the relationship between the chemical properties of Gd(III) complexes and their toxicity (Cacheris, W. P. Q. et al., *Magn. Reson. Imag.* 1990, 8, 467; Wedeking, P. K. et al., *Magn. Reson. Imag.* 1991, 10, 641; Pattagunta, N. R. G. et al., *Invest. Radiol.* 1996, 10, 619; Pattagunta, N. R. G. et al., *Invest. Radiol.* 1996, 12, 739; Kumar, K. T. et al., *Inorg Chem.* 1995, 34, 6472). The toxicity is due to the exchange of Gd$^{3+}$ with physiological cations such as Zn(II), Cu(II), and Ca(II)—the free ligand and Gd(III) ion are significantly more harmful than the intact complex (Lauffer, R. B., *Chem. Rev.* 1987, 87, 901).

Similar to other MRI contrast agents, a complex between Gd(III) and a ligand with only oxygen donor atoms must be acceptably stable and non-toxic. The inventors have recognized that a complex between Gd(III) and an oxygen donor ligand will preferably form an aqueous solution that has a pGd of at least about 18 when the aqueous solution is pH about 7.4 and includes about 10 μM of ligand and about 1 μM of Gd. See, Equation 4, infra.

Figure 5:
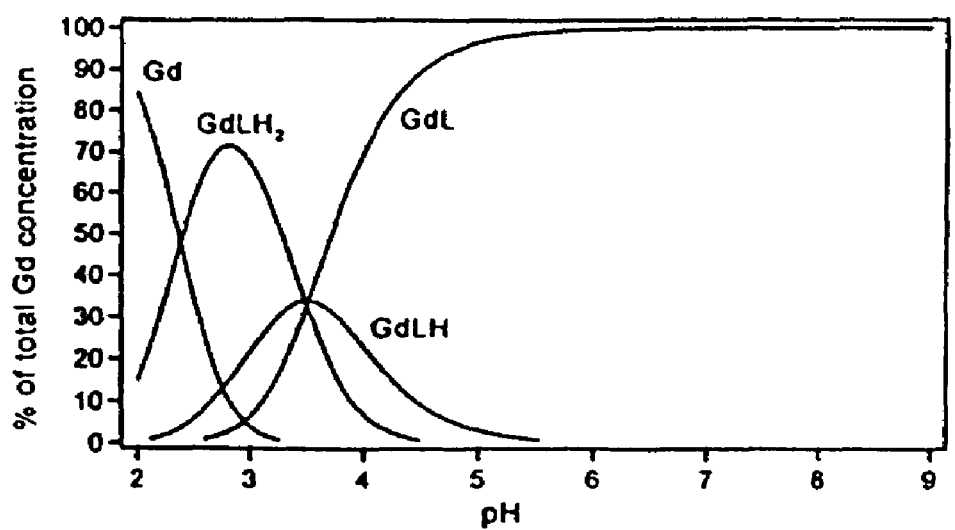
FIG. 5 is a species distribution diagram for the $Gd^{3+}$/TREN-1-Me-HOPO system, calculated for 1 μM Gd and 10 μM ligand. The ligand is represented as "L" in the diagram.
Figure 6:
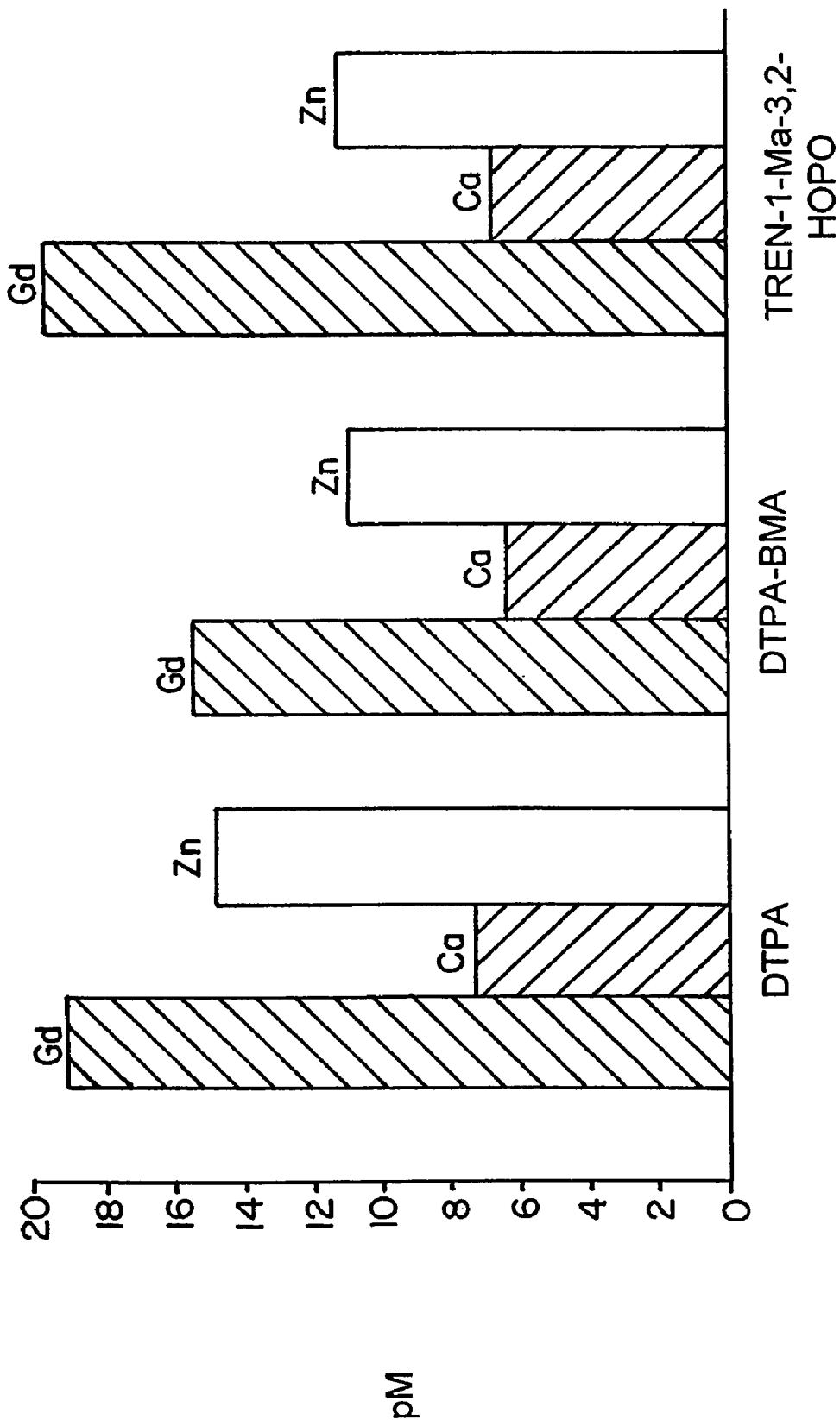
FIG. 6 is a graphical display of the selectivity of TREN-1-Me-HOPO for $Gd^{3+}$ over $Ca^{2+}$ and $Zn^{2+}$ as compared with DTPA and DTPA-BMA.

The speciation of an exemplary complex of the invention, Gd(III)-TREN-1-Me-HOPO in water is unchanged over the pH range 5.5-10 (FIG. 5), indicating that at physiological pH the ligand remains deprotonated and the complex remains intact. TREN-1-Me-HOPO is also highly thermodynamically stable (pGd=20.3) and is of very low toxicity. In comparison with DTPA, DTPA-BMA, and DOTA, TREN-1-Me-HOPO exhibits enhanced selectivity (FIG. 6) for Gd$^{3+}$ over the physiological metal ions Ca$^{2+}$ and Zn$^{2+}$ (Xu, J. et al., *J. Am. Chem. Soc.* 1995, 117, 7245), which indicates that the dissociation of TREN-1-Me-HOPO is minimal in vivo. The low toxicity of TREN-1-Me-HOPO to mice is also of pre-clinical importance (Xu, J. et al., *J. Med. Chem.* 1995, 38, 2606-2614; Raymond, K. N. et al., U.S. Pat. No. 5,892,029 (1999)).

Complexes

In a first aspect, the present invention provides a complex between a gadolinium (III) ion and an organic ligand comprising only oxygen donor atoms coordinating the gadolinium (III) ion. The complexed gadolinium ion has a water exchange rate of at least about $10 \times 10^6$ sec$^{-1}$. The solubility in water of the complex is at least about 15, preferably, at least about 20 mM.

In an exemplary embodiment, the present invention provides a complex between a gadolinium (III) ion and an organic ligand. The ligand includes a structure according to Formula I:

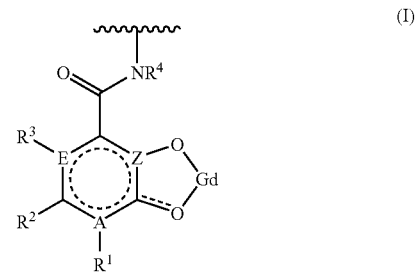

in which, the symbols $R^1$, $R^2$, and $R^3$ are independently selected from a linking member, an aryl group substituent, H, substituted or unsubstituted alkyl, substituted or unsubstituted aryl, substituted or unsubstituted heteroalkyl, hydroxy, carboxy, amide, ester, and amino groups, with the proviso that when A is nitrogen, $R^1$ is other than amino, and with the further proviso that when E is nitrogen, $R^3$ is not present. The symbol $R^4$ is a linking member, alkyl group substituent, H, substituted or unsubstituted alkyl, substituted or unsubstituted heteroalkyl, substituted or unsubstituted aryl, hydroxy, carboxy, amide, or an ester group. A, E and Z are independently selected from carbon and nitrogen. The gadolinium complex has a solubility in water of at least about 15 mM, more preferably, at least about 20 mM.

In another exemplary embodiment, the moiety according to Formula I has the structure:

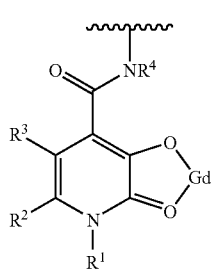

(Ia)

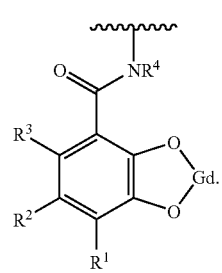

(Ic)

in which the symbols $R^1$ and $R^4$ represent members independently selected from a linking member, H, substituted or unsubstituted alkyl, substituted or unsubstituted aryl, substituted or unsubstituted heteroalkyl, hydroxy, carboxy, amide, or an ester groups. $R^2$ and $R^3$ are independently selected from a linking member, an aryl substituent, H, substituted or unsubstituted alkyl, substituted or unsubstituted aryl, substituted or unsubstituted heteroalkyl, hydroxy, carboxy, amide, ester, or an amino group.

In yet another embodiment according to Formula Ia, $R^1$ and $R^2$ are independently $C_1$-$C_4$ substituted or unsubstituted alkyl, e.g., methyl. In a further embodiment, $R^1$ and $R^2$ are independently selected from methyl and H; and $R^3$ and $R^4$ are H. In yet another embodiment, $R^1$ is selected from substituted or unsubstituted aryl and substituted or unsubstituted (alkyl) aryl; and $R^2$ is substituted or unsubstituted $C_1$-$C_4$ alkyl.

In another exemplary embodiment, the moiety according to Formula I has the structure:

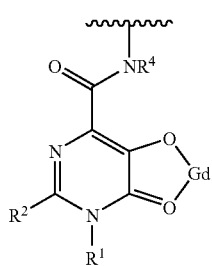

(Ib)

in which $R^1$ and $R^4$ are independently selected from a linking member, H, substituted or unsubstituted alkyl, substituted or unsubstituted aryl, substituted or unsubstituted heteroalkyl, hydroxy, carboxy, amide, and ester groups. The symbol $R^2$ represents a linking member, an aryl group substituent, H, substituted or unsubstituted alkyl, substituted or unsubstituted aryl, substituted or unsubstituted heteroalkyl, hydroxy, carboxy, amide, ester, and amino groups.

In another embodiment wherein the structure according to Formula I has the structure set forth above, the symbols $R^1$, $R^2$ and $R^4$ represent members independently selected from H and substituted or unsubstituted $C_1$-$C_4$ alkyl. In a further embodiment, at least one of $R^1$ and $R^2$ is methyl.

In yet a further exemplary embodiment, the structure according to Formula I is:

The identities of the radicals $R^1$—$R^4$ are substantially as discussed above for Formula I.

In another exemplary embodiment, the invention provides a complex in which the structure according to Formula I is:

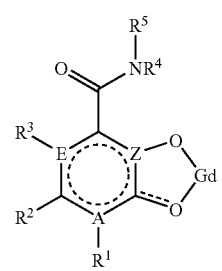

(Id)

wherein $R^5$ is substituted or unsubstituted alkyl, substituted or unsubstituted heteroalkyl, or substituted or unsubstituted aryl. $R^5$ is optionally substituted with one or more organic ligands that are also complexed to the gadolinium (III) ion. The identity of the remaining radicals is substantially as discussed above for Formula I. $R^5$ is exemplary of a moiety referred to herein as a "scaffold." The scaffold is the backbone that tethers together two or more chelating units to form the ligands of the invention. The scaffold is optionally further substituted with a reactive functional group. The functional groups can be used to attach the ligand to another species, e.g., a targeting moiety, polymer, etc.

A further exemplary complex of the invention has a structure according to Formula II:

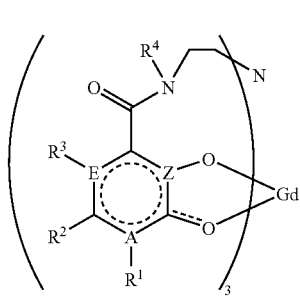

(II)

wherein each $R^1$, $R^2$, $R^3$ and $R^4$; and each A, E and Z for each of the three ring systems is independently selected, and the identity of the radicals is as set forth above for Formula I. Thus, for example, a first $R^1$ on a first chelating ring structure may be methyl; a second $R^1$, which is located on a second ring is ethyl; and a third $R^1$, which is located on a third ring may be benzyl.

In yet a further exemplary embodiment, the invention provides a complex wherein the structure according to Formula II is:

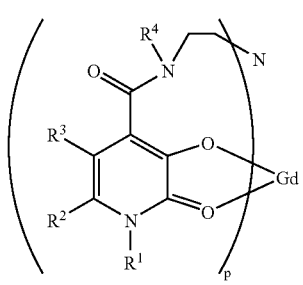

(IIa)

The symbol p represents an integer from 1 to 3.

In yet another exemplary embodiment, the invention provides a complex in which the structure according to Formula II is:

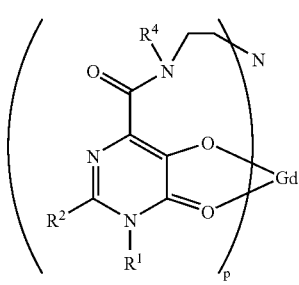

(IIb)

In Formulae Ia and IIb, when p is less than three the valency of the nitrogen outside of the parentheses is satisfied by its substitution with a substituted or unsubstituted alkyl or substituted or unsubstituted heteroalkyl group. The preferred substituents for the alkyl or heteroalkyl group is a chelating moiety having a structure different than that within the parentheses. When p is greater than one, each of the radicals on each of the p rings is independently selected. The identities of the substituents are as described for Formula II.

In a still further exemplary embodiment, the invention provides a complex in which the structure according to Formula II is:

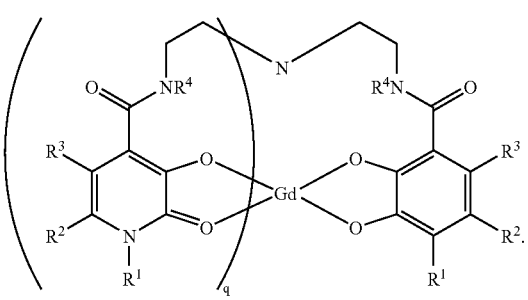

(IIc)

The identity of each of the substituents is substantially similar to those set forth above for Formula II. In a further embodiment according to Formula IIc, $R^1$ is methyl or substituted or unsubstituted benzyl. When the benzyl is substituted, in an exemplary embodiment, it is substituted with an alkoxy group. In yet another embodiment, at least one member selected from $R^1$ and $R^2$ is substituted or unsubstituted $C_1$-$C_4$ alkyl, e.g., as methyl. In another embodiment, at least one $R^1$ is selected from methyl and polyether. The symbol q represents an integer from 1 to 2.

In yet another embodiment, the invention provides a complex wherein the structure according to Formula II is:

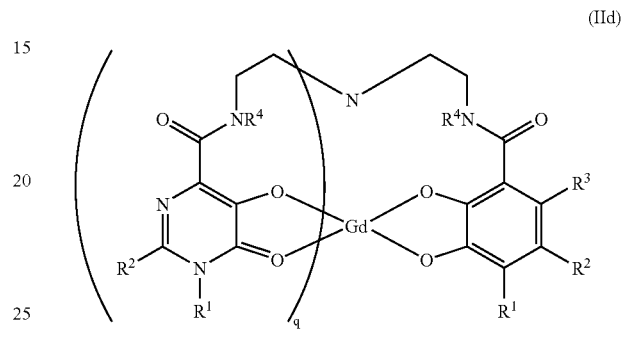

(IId)

in which the radicals are each independently selected and their identities are substantially as discussed above. The symbol q represents an integer from 1 to 2.

In Formulae IIc and IId, when q is less than three, the valency of the nitrogen outside of the parentheses is satisfied by its substitution with a substituted or unsubstituted alkyl or substituted or unsubstituted heteroalkyl group. The preferred substituents for the alkyl or heteroalkyl group is a chelating moiety having a structure different than that within the parentheses. When q is greater than one, each of the radicals on each of the p rings is independently selected. The identities of the substituents are as described for Formula II.

Synthesis

The invention provides methods for preparing oxygen donor ligands having the have the desirable properties discussed herein. The synthesis of homopodal ligands of the invention is exemplified by the synthesis of Gd(TREN-1-Me-HOPO)(H$_2$O)$_2$] (tris[(3-hydroxy-1-methyl-2-oxo-1,2-didehydropyridine-4-carboxamido)ethyl]amine), which is the first member of a series of heterocyclic (pyridonate) oxygen donor complexes having characteristics which are desirable in an MRI agent (Xu, J. et al., *J. Am. Chem. Soc.* 1995, 117, 7245). The synthesis of TREN-1-Me-HOPO is shown in Scheme 1.

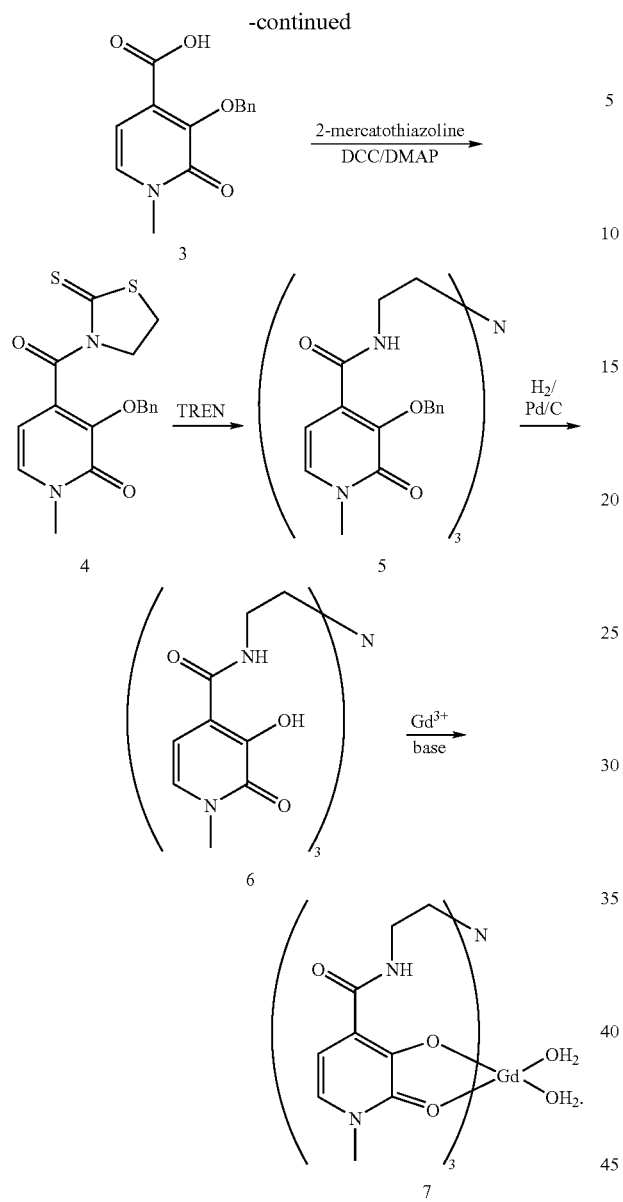

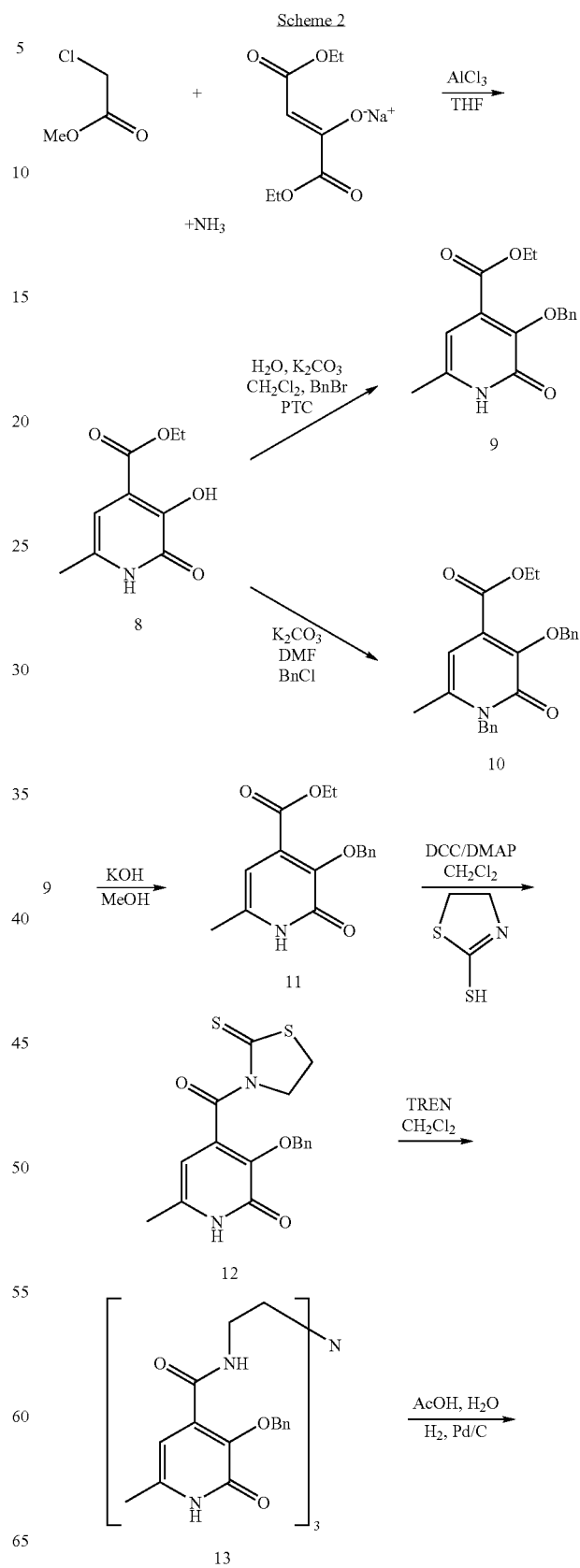

The endocyclic nitrogen of the pyridinone unit is readily functionalized by methods such as that set forth in Scheme 2:

Scheme 2

In Scheme 1, N-methyl-hydroxypyridinone precursor 1 is carboxylated to form the corresponding acid 2. The hydroxyl group of the acid is protected as the benzyl adduct 3, which is converted to the corresponding thiazolide 4. The thiazolide is combined with the TREN backbone, forming 5, which is deprotected by catalytic hydrogenation to afford 6. The gadolinium complex 7, is formed by combining the ligand with a source of gadolinium ion in the presence of a base.

Those of skill in the art will understand that the method set forth above is general for the preparation of ligands based upon other backbone motifs. Moreover, the method is useful for preparing ligands in which the chelating units within a ligand have a structure other than the parent HOPO chelating unit. Furthermore, the N-methyl precursor is readily replaced with its unsubstituted analogue, or by analogues that are N-substituted with a moiety other than a methyl group, such as a substituted or unsubstituted alkyl, substituted or unsubstituted heteroalkyl or a substituted or unsubstituted aryl moiety.

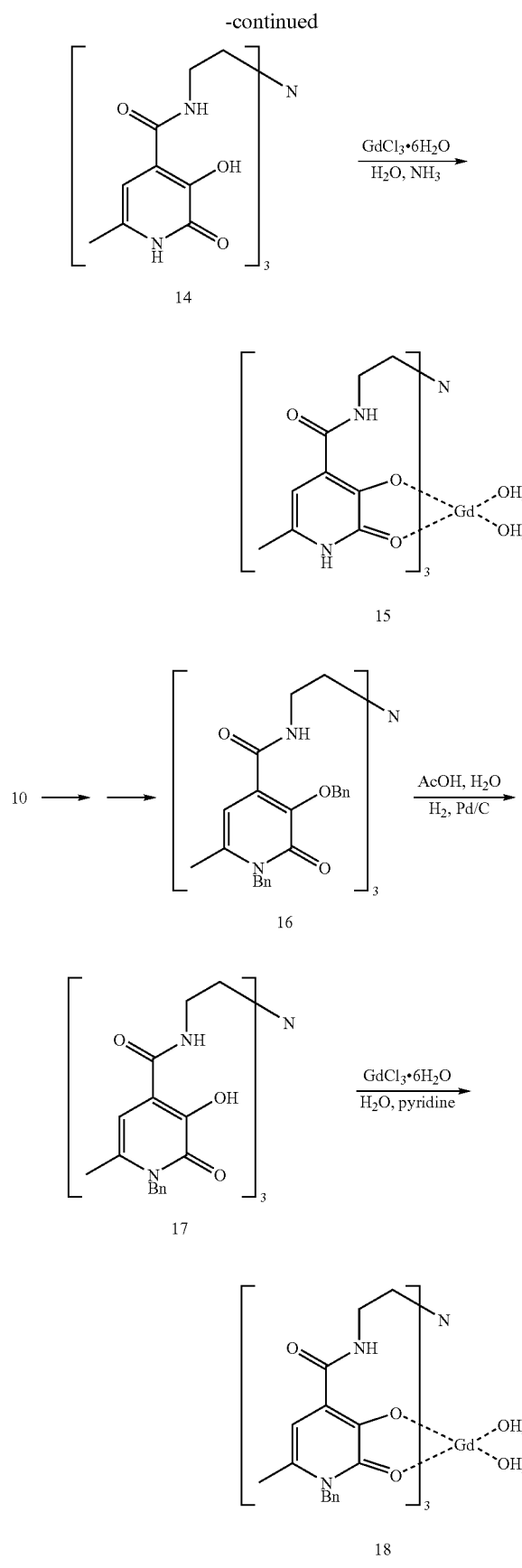

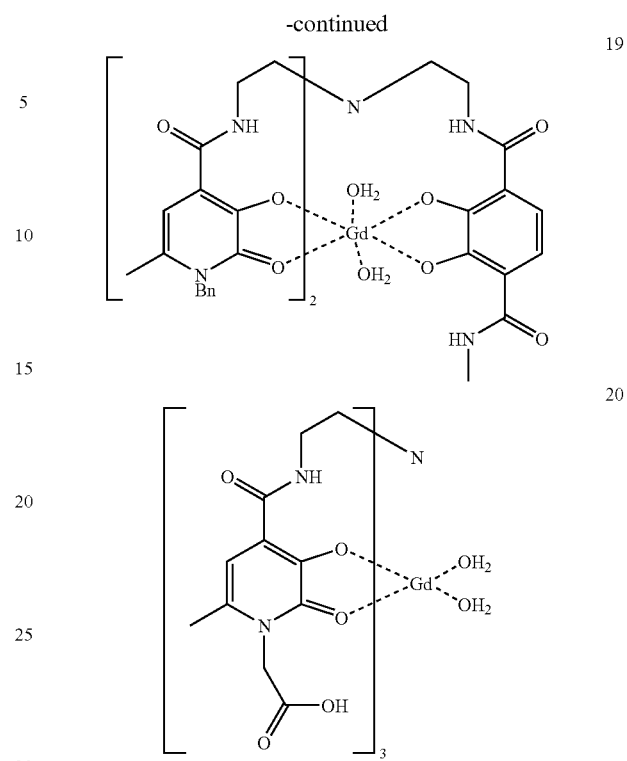

The protected hydroxypyridinone carboxylic acid ester 8 is a versatile intermediate for the preparation of variously substituted chelating units. Thus, in one route, 8 is benzylated at each available site, affording compound 10. In an alternate route, the endocyclic amine is left unbenzylated, providing compound 9.

The ester of compound 9 is hydrolyzed to the corresponding carboxylic acid 11, which is converted to thiazolide 12. The thiazolide is conjugated with the amine backbone to yield 13, which is subsequently debenzylated to compound 14. The Gd(III) complex 15 is formed by standard methods.

Similarly, compound 10 is coupled with the amine backbone, debenzylated to yield the hydroxyl moiety and gadolinium chelate 18 is formed. The route also provides for forming heteropodal ligands, such as 19, and ligands in which the endocyclic nitrogen is functionalized with groups other than benzyl, e.g., 20. [Gd(TREN-MOE-HOPO)(H$_2$O)$_2$] is a representative embodiment of a ligand that is N-substituted with a moiety other than a methyl group, the ligand of the invention includes a HOPO chelating moiety, which is functionalized at the endocyclic nitrogen of the pyridinone moiety with a linker or other group, e.g., (Johnson, A. R. et al., *Inorg. Chem.* 2000, 39, 2652-2660). The MOE derivative is more than 10-times more water soluble than the parent complex. Moreover, the stability of [Gd(TREN-MOE-HOPO)(H$_2$O)$_2$] was similar to that of the parent methyl derivative (pGd=19.8).

Ligands Incorporating Terephthalamides

In addition to the methods provided herein for functionalizing the scaffold and the pyridine nitrogen of the chelates of the invention, there is provided an additional method of functionalizing the chelates for subsequent attachment to another species or to obtain desirable properties. The method exploits free amide functionality of a TAM moiety attached to the scaffold. The TAM moiety can be functionalized either prior to or following its conjugation with the scaffold. A route to an exemplary compound of the invention, combining HOPO and TAM chelating moieties with a TREN backbone is shown in Scheme 3.

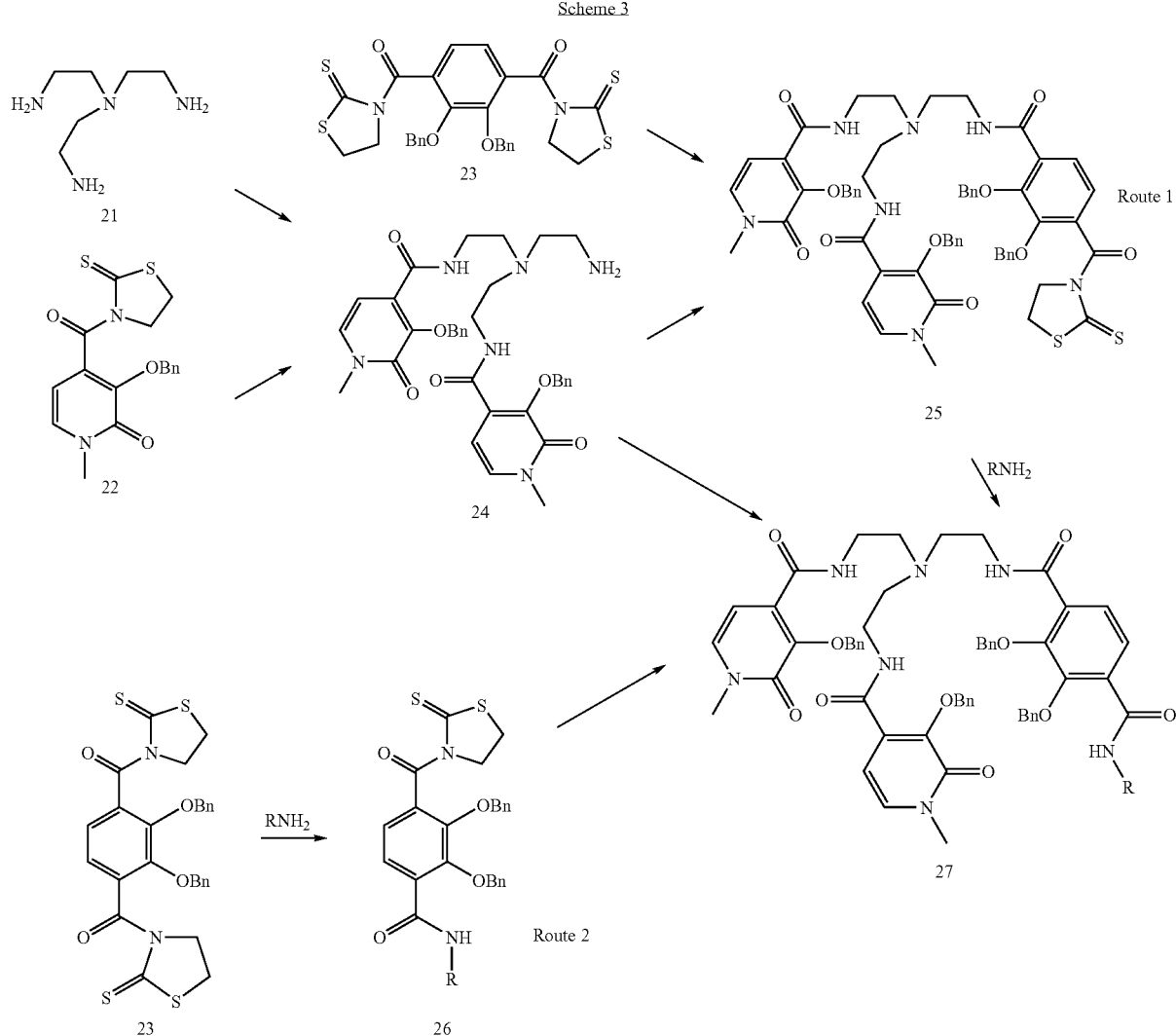

Scheme 3

In Scheme 3, TREN backbone 21 is contacted with protected thiazolide 22 to produce disubstituted TREN 24 with a single free primary amine group. Compound 24 is contacted with the protected di-thiazolide TAM derivative 23, yielding activated heteropodal ligand 25 which can be subsequently reacted with an amine to form the functionalized heteropodal ligand 27.

In an alternative route, the protected di-thiazolide 23 is functionalized with an amine, producing amide 26, prior to its reaction with the disubstituted TREN derivative 24, producing heteropodal ligand 27.

TREN-HOPO-TAM compounds of the invention are readily synthesized using either of the routes of Scheme 3. The use of benzyl (Bn) protecting groups on TAM is generally preferable to the methyl groups previously reported (Cohen, S. M. et al., *Inorg. Chem.* 2000, 39, 4339), since the deprotection conditions are less severe, making the method amenable to use with a greater range of primary amines ($RNH_2$). Optimization of the reaction conditions for a particular amine ($RNH_2$) is well within the abilities of one of skill in the art.

Other examples of mixed ligands are set forth below:

$R_1$ and/or $R_2$ =

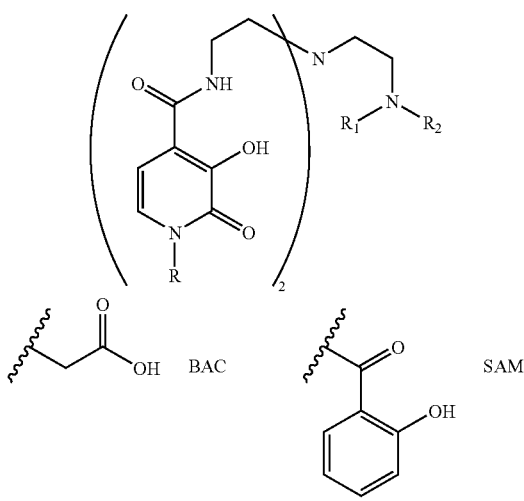

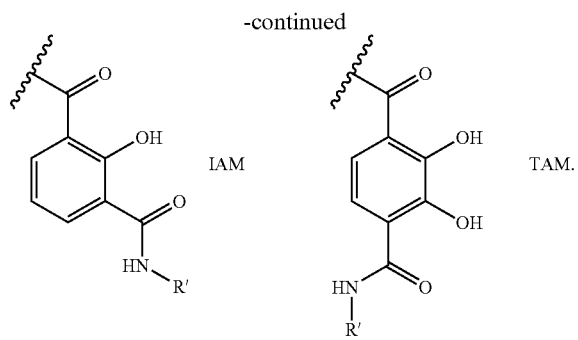

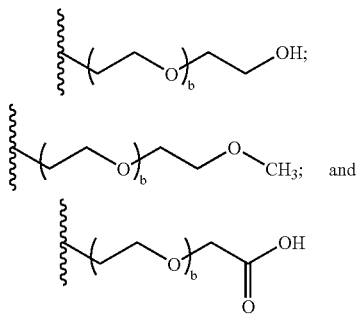

See, for example, Cohen, S. M. et al., *Inorg. Chem.* 39: 5747 (2000). The groups labeled R and R' are typically H, a substituted or unsubstituted alkyl, or substituted or unsubstituted heteroalkyl group. In an exemplary embodiment, R and/or R' are groups that include an ether or a reactive functional group.

In yet another exemplary embodiment, the invention provides a compound according to Formula I, wherein at least one of $R^1$, $R^2$, $R^3$ and $R^4$ is a linker arm, including a reactive functional group that allows the compound to be tethered to another species. Alternatively, at least one of $R^1$, $R^2$, $R^3$ and $R^4$ is a moiety that alters a property, e.g., water solubility, molecular weight, rotational correlation time, complex stability, etc., of the parent compound to which it is affixed.

In a representative embodiment, at least one of $R^1$, $R^2$, $R^3$ and $R^4$ has the structure:

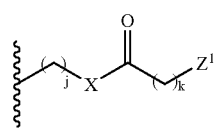

wherein $Z^1$ is a member selected from H, $CH_2$, $OR^{10}$, $SR^{10}$, $NHR^{10}$, $OCOR^{11}$, $OC(O)NHR^{11}$, $NHC(O)OR^{10}$, $OS(O)_2OR^{10}$, and $C(O)R^{11}$. The symbol $R^{10}$ represents H, substituted or unsubstituted alkyl, or substituted or unsubstituted heteroalkyl. $R^{11}$ is a member selected from H, $OR^{12}$, $NR^{12}NH_2$, SH, $C(O)R_2$, $NR^{12}H$ substituted or unsubstituted alkyl and substituted or unsubstituted heteroalkyl. $R^{12}$ is a member selected from H, substituted or unsubstituted alkyl and substituted or unsubstituted alkyl. The symbol X represents a member selected from $CH_2$, O, S and $NR^{13}$, wherein $R^{13}$ is a member selected from H, substituted or unsubstituted alkyl and substituted or unsubstituted heteroalkyl; and the symbols j an k represent members independently selected from the group consisting of integers from 1 to 20. Other linking moieties useful with the compounds of the invention will be apparent to those of skill in the art.

In another exemplary embodiment, at least one of $R^1$, $R^2$, $R^3$ and $R^4$ is an ether or a polyether, preferably a member selected from ethylene glycol, and ethylene glycol oligomers, having a molecular weight of from about 60 daltons to about 10,000 daltons, and more preferably of from about 100 daltons to about 1,000 daltons.

Representative polyether-based substituents include, but are not limited to, the following structures:

in which b is preferably a number from 1 to 100, inclusive. Other functionalized polyethers are known to those of skill in the art, and many are commercially available from, for example, Shearwater Polymers, Inc. (Alabama).

In a preferred embodiment, the linker includes a reactive functional group for conjugating the compound to another molecule or to a surface. Representative useful reactive groups are discussed in greater detail in succeeding sections. Additional information on useful reactive groups is known to those of skill in the art. See, for example, Hermanson, BIOCONJUGATE TECHNIQUES, Academic Press, San Diego, 1996.

In yet another exemplary embodiment, the moiety attached to at least one of $R^1$, $R^2$, $R^3$ and $R^4$ combines characteristics of one or more of the above-recited groups. For example, one preferred linker group combines both the attributes of a polyether and a reactive group:

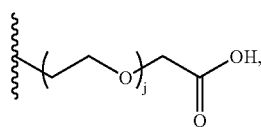

in which j is an integer between 1 and 100, inclusive. Other "bifunctional" linker groups include, but are not limited to, moieties such as sugars (e.g., polyol with reactive hydroxyl), amino acids, amino alcohols, carboxy alcohols, amino thiols, and the like.

The linkers of use in the compounds of the invention can also include a cleaveable group. In an exemplary embodiment, the cleaveable group is interposed between the signal-generating moiety, i.e., the complex, and a targeting agent or macromolecular backbone.

Synthesis and Properties of 6-Carboxamido-2,3-methyl-5,4-hydroxypyrimidinone Ligands The invention also provides complexes based upon a new heterocyclic ligand system, hydrogen bond stabilized, bidentate oxo-hydroxy donor ligands. In an exemplary embodiment, the new heterocyclic ligand system utilizes the pyrimidinone analogue of the TREN-HOPO class of ligands, TREN-HOPY (HOPY=6-carboxamido-2,3-methyl-5,4-hydroxypyrimidinone). The pKa of TREN-HOPY is 6.37, close to that of TREN-1-Me-HOPO (6.12), indicating that the HOPY subunit is slightly more basic. However, the pGd of [Gd(TREN-HOPY)(H$_2$O)$_2$] is an acceptable 18.0. Of equal importance, the selectivity of Gd(III)TREN-HOPY over physiological cations Ca(II) and Zn(II) is similar to that of TREN-1-Me-HOPO.

The water solubility of [Gd(TREN-HOPY)(H$_2$O)$_2$] is greater than 0.1 M, which is much higher than that of the other HOPOs and is an unexpected feature of this complex. The relaxivity of [Gd(TREN-HOPY)(H$_2$O)$_2$] in water at 20 MHz, 25° C. and pH 7.2 is 9.0 mM$^{-1}$s$^{-1}$, comparable to [Gd(TREN-HOPO)(H$_2$O)$_2$] and significantly higher than commercial MRI agents. The short water residence time of 2 ns, at 298 K, is comparable to members of the HOPO and heteropodand series and indicates that the relaxivity of the HOPY complexes is not limited by slow water exchange kinetics. The rotational correlation time of [Gd(TREN-HOPY)(H$_2$O)$_2$] is about 50% higher than that for the DOTA and DTPA Gd(III) complexes.

In a preferred embodiment, the relaxivity of a chelate such as [Gd(TREN-HOPY)(H$_2$O)$_2$] in the presence of endogenous anions is essentially constant, generally indicating that the integrity of the coordination sphere is maintained and the two water molecules are not displaced.

The relaxivity of [Gd(TREN-HOPY)(H$_2$O)$_2$] in serum, at 298 K, is significantly higher (ca. 35% at 20 MHz) than in pure water due to a weak interaction (Ka ca. 100 M$^{-1}$) of the complex with HSA (resulting in a higher τ$_r$) These highly desirable properties make [Gd(TREN-HOPY)(H$_2$O)$_2$] a promising candidate for the preparation of macromolecular MRI agents with enhanced relaxivity.

Synthesis of Compounds with the HOPY Motif

Syntheses of compounds with the HOPY motif have been previously reported (Culbertson, T. P., *J. Heterocyclic Chem.*, 16:1423 (1979); Golankiewicz, K.; Wyrzykiewicz, E., *Roc. Chem. Ann. Soc. Chim. Pol.*, 47:1965 (1973); Budesinsky et al., *J. Coll. Czec. Chem. Comm.*, 27:2550 (1963)), albeit as unexpected products in the study of other heterocyclic systems. Difficulties with reproducibility, (Budesinsky et al., *J. Coll. Czec. Chem. Comm.*, 27:2550 (1963)) preparative scale-up, (Golankiewicz, K.; Wyrzykiewicz, E., *Roc. Chem. Ann. Soc. Chim. Pol.*, 47:1965 (1973)) or substrate specificity (which precluded the development of a general synthesis), (Culbertson, T. P., *J. Heterocyclic Chem.*, 16:1423 (1979); Golankiewicz, K.; Wyrzykiewicz, E., *Roc. Chem. Ann. Soc. Chim. Pol.*, 47:1965 (1973)) highlights the need for a new synthetic route.

In the present invention, synthesis of the desired class of functionalized HOPYs is achieved by modifying and extending the 5,4-hydroxypyrimidinone synthesis of Davoll and Laney, (Davoll, J.; Laney, D. H., *J. Chem. Soc.*, 2124 (1956)) where 28 was reported (Scheme 4).

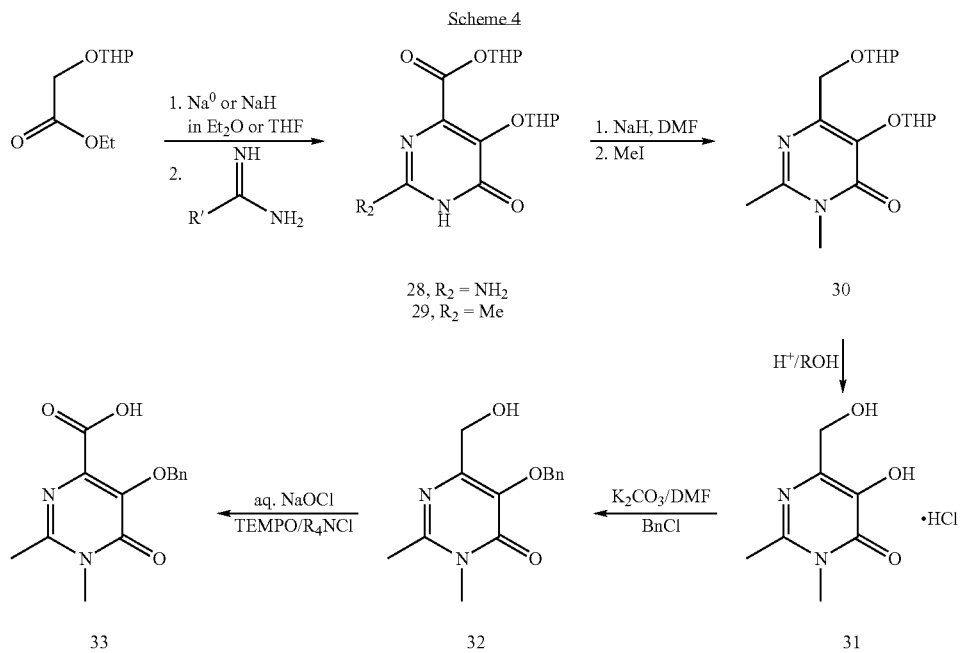

Scheme 4

The self-condensation of tetrahydropyran protected ethyl glycolate (Davoll, J.; Laney, D. H., *J. Chem. Soc.*, 2124 (1956)) provides the corresponding β-ketoester, which is combined in situ with acetamidine in ethanol to afford 28. The $^1$H and $^{13}$C NMR spectra of 28 indicates that it is an equal mixture of two diastereomers, resulting from chirality at the two THP acetal carbons. Methylation of 28 with NaH/MeI/DMF (Jonak et al., *J. Org. Chem.*, 35: 2512 (1970)) gives 30 as a thick oil of >90% purity. Deprotection of 30 (4M HCl dioxane/2-propanol) provides pure 31 HCl, alleviating the necessity to further purify 31, the oily precursor. Re-protection of the 5-hydroxy group (BnCl/K$_2$CO$_3$/DMF) gave 32.

Compound 32 is a useful intermediate in the preparation of multidentate HOPY-containing ligands where the electronic and structural influences of an amide group are not desired.

Oxidation of 32 using bleach with TEMPO catalyst under phase transfer conditions (Anelli et al., *J. Org. Chem.*, 52:2559 (1987)) provided analytically pure 33 after careful acidification of the crude reaction extracts. In an exemplary embodiment, the present invention provides a synthetic route of HOPY-containing chelates, which does not require chromatography in preparing the key ligand precursor, HOPY carboxylic acid, 33.

A second preparation of 33 was also developed as outlined in Scheme 5.

29

Scheme 5

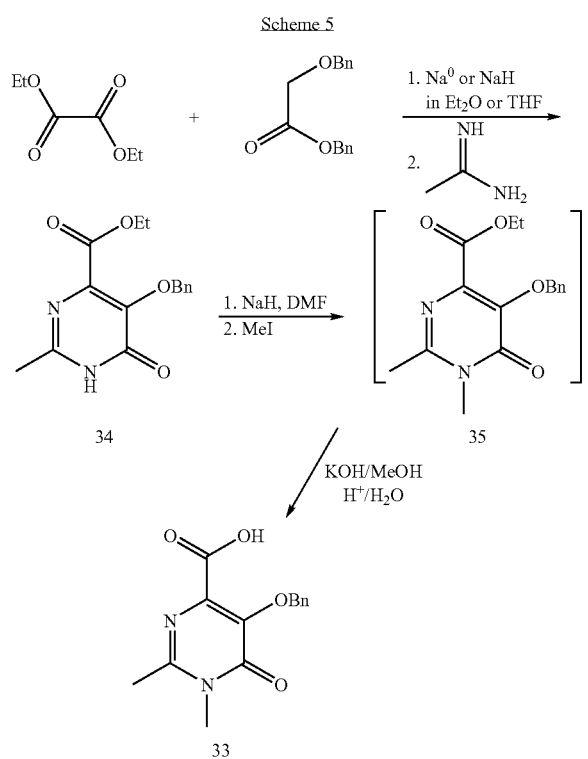

The Claisen condensation product of ethyl oxalate and 2-benzyloxy benzyl acetate was reacted with acetamidine in ethanol to provide 34. N-Methylation was performed by the previously described method (MeI/NaH/DMF) and provided the $N^3$ alkylated isomer 35, which, after hydrolysis gave the HOPY acid 33.

In another exemplary embodiment (Scheme 6), 37 (and then 38) was prepared from 36 (from Scheme 5).

Scheme 6

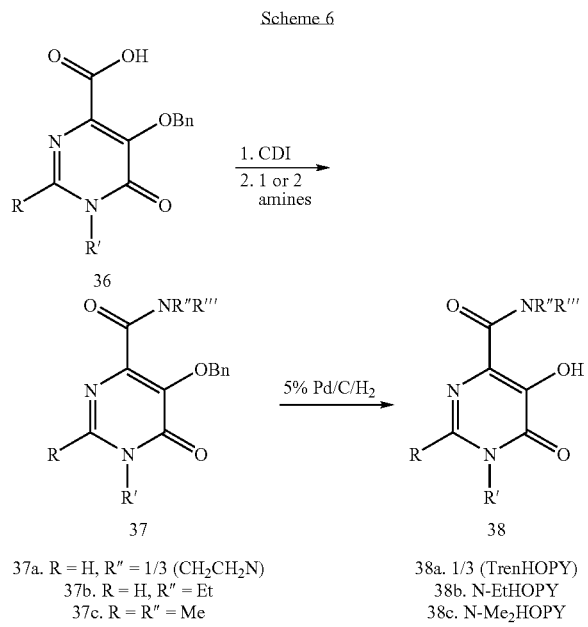

37a. R = H, R″ = 1/3 (CH$_2$CH$_2$N)
37b. R = H, R″ = Et
37c. R = R″ = Me 38a. 1/3 (TrenHOPY)
38b. N-EtHOPY
38c. N-Me$_2$HOPY

30

Conversion of 36 into an activated ester with CDI and in situ reaction with the appropriate amines, gave 37a-c in 70-90% yield (Scheme 6). Deprotection of the benzyl protecting group and recrystallization afforded the free ligands 38 which were obtained as analytically pure white solids. TrenHOPY, 38a, N-EtHOPY, 38b, and N-Me$_2$HOPY, 38c, were prepared in this manner.

According to the invention, a ligand can include only HOPY chelating moieties attached to a selected scaffold. Alternatively, the HOPY subunits are combined with HOPO and/or TAM chelating units on a selected backbone to provide an array of mixed ligands. Moreover, similar to the HOPO subunits, the HOPY subunits are optionally derivatized with one or more linker arms or reactive functional groups.

Scaffolds

Throughout the instant specification, the complexes of the invention are exemplified by embodiments in which one or more heterocyclic complexing group is attached to a linear, polyfunctional scaffold, forming a chelating agent with the correct geometry to complex a metal ion. Generally, scaffolds of use in the complexes and chelating agents of the invention are exemplified by the use of TREN. The focus on the TREN scaffold is for clarity of illustration only and should not be interpreted as limiting the scope of the invention to a genus of chelating agents and complexes having a TREN backbone. Those of skill in the art will appreciate that a wide array of scaffold structures can be used as scaffold moieties in the compounds of the invention. For example, scaffolds of use in the present invention can be linear, cyclic, saturated or unsaturated species. Some exemplary scaffold moieties are set forth below:

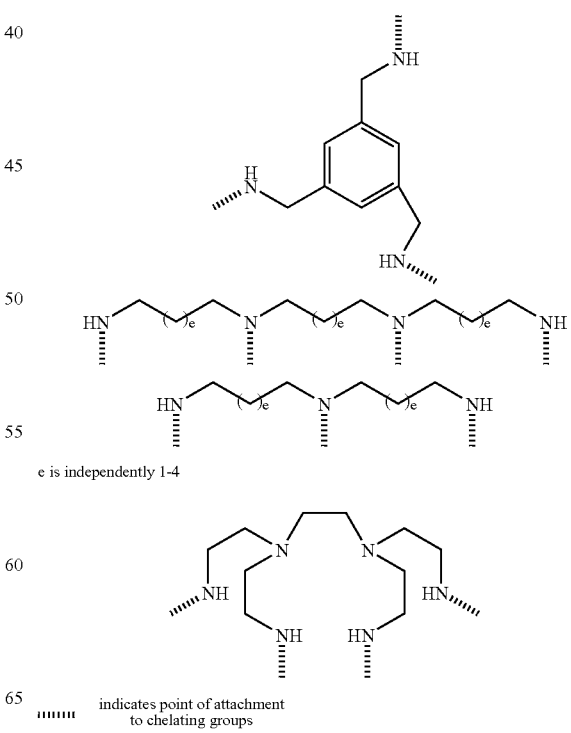

e is independently 1-4

||||||| indicates point of attachment to chelating groups

-continued

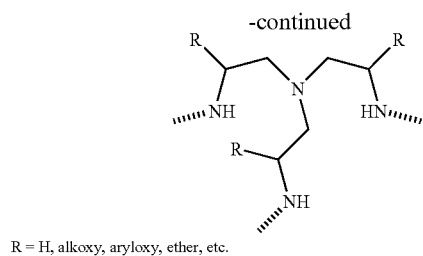

R = H, alkoxy, aryloxy, ether, etc.

Additionally, it is within the scope of the present invention to utilize scaffolds that are functionalized with moieties that are available for interaction with a group on another molecule. Thus, the scaffolds can include reactive functional groups, infra, in addition to those that are used to form the link between the scaffold and the chelating heterocyclic rings.

Functionalization of the TREN Scaffold

In another exemplary embodiment, the water solubility of the complexes of the invention is enhanced by the functionalization of the scaffold with an appropriate group. Thus, synthetic methodologies were developed to enhance the solubility of TREN-1-Me-HOPO by the functionalization of the TREN cap to form homochiral tris(2-hydroxymethyl)-TREN-1-Me-HOPO (Hajela, S. B. et al., *J. Am. Chem. Soc.* 2000, 122, 11228).

Figure 7:
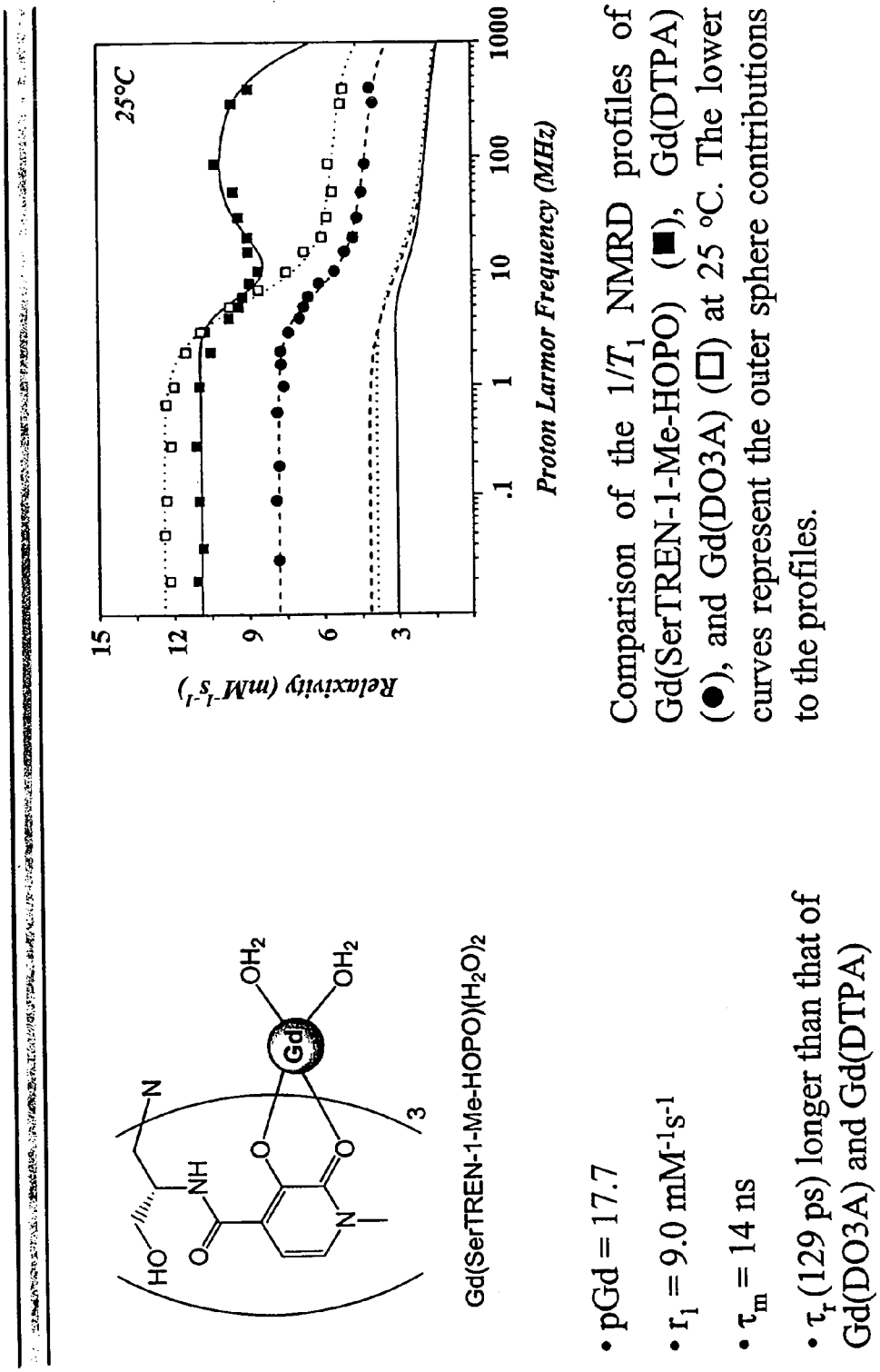
FIG. 7 displays the structure of a representative Gd(III)-HOPO chelate and provides a graphical comparison the the NMRD profile of this compound with those of representative Gd(III)-polyaminocarboxylates.

In an exemplary embodiment, the invention provides a Gd(III) complex of [Gd(SerTREN-1-Me-HOPO)(H$_2$O)$_2$] (FIG. 7). The complex has a solubility in water of ca. 15 mM (25° C., pH 7), a proton relaxivity (r$_1$) of 9.0 mM$^{-1}$s$^{-1}$ (at 25° C., 20 MHz), which is significantly higher than those of the current mono-aquo MRI contrast agents. Of importance, the water residence lifetime ($\tau_m$) is extremely short (14 ns) and is at least two orders of magnitude higher than commercial MRI agents; this water exchange rate is close to optimal for slowly rotating MRI contrast agents. Since the Gd(III) cation is 8-coordinate in the ground state, an associative mechanism is expected to account for the water exchange mechanism (Helm, L. et al., *Coord. Chem. Rev.* 1999, 187, 151). The fast water exchange observed is attributed to the small difference in energy between the eight- and nine-coordinate states. Thus, unlike derivatives of DOTA and DTPA, the relaxivity of derivatives of TREN-1-Me-HOPO are not limited by slow water exchange.

Figure 8:
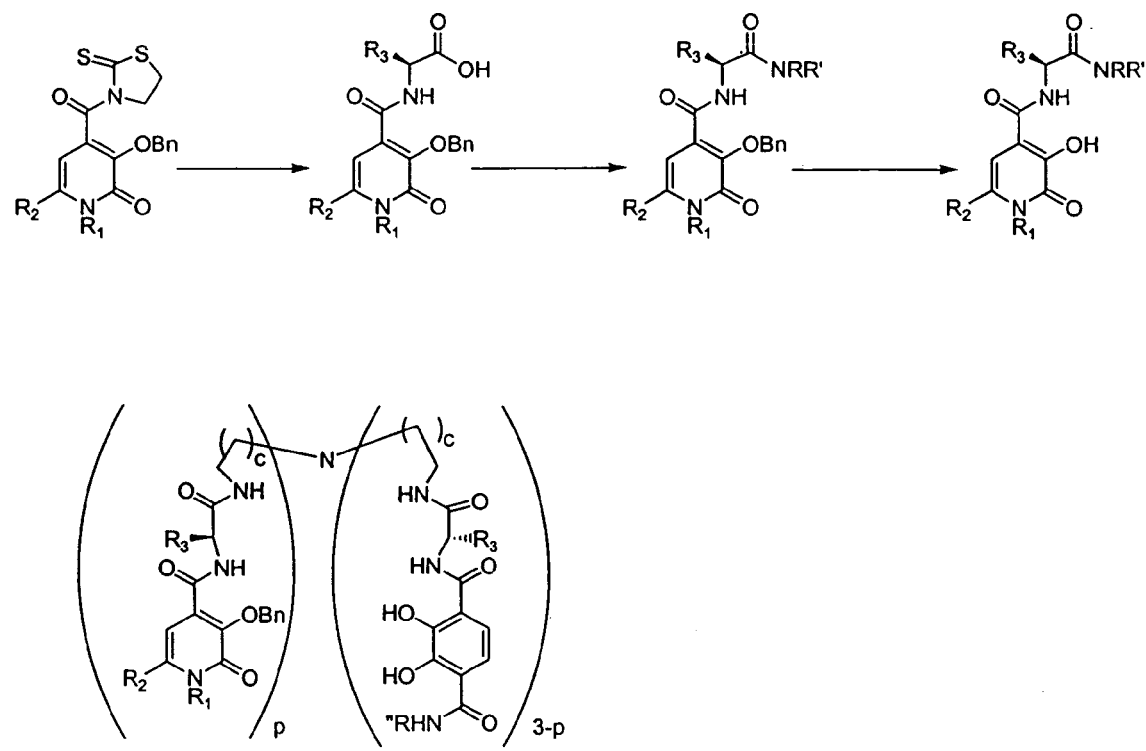
FIG. 8 is an exemplary synthetic route to compounds of the invention having derivatized scaffolds with alkylene moieties of different lengths.

As illustrated in FIG. 8, the substituent on the scaffold can be substantially any group including, but not limited to, reactive functional groups, substituted or unsubstituted alkyl, substituted or unsubstituted heteroalkyl or substituted or unsubstituted aryl groups.

In yet another exemplary embodiment, the ligand backbone includes an ether or poly(ether), preferably an ethylene glycol oligomer. A synthetic scheme to an exemplary ether derivatized backbone is set forth in Scheme 7:

Scheme 7

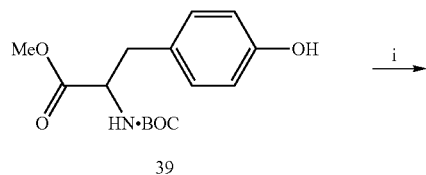

39

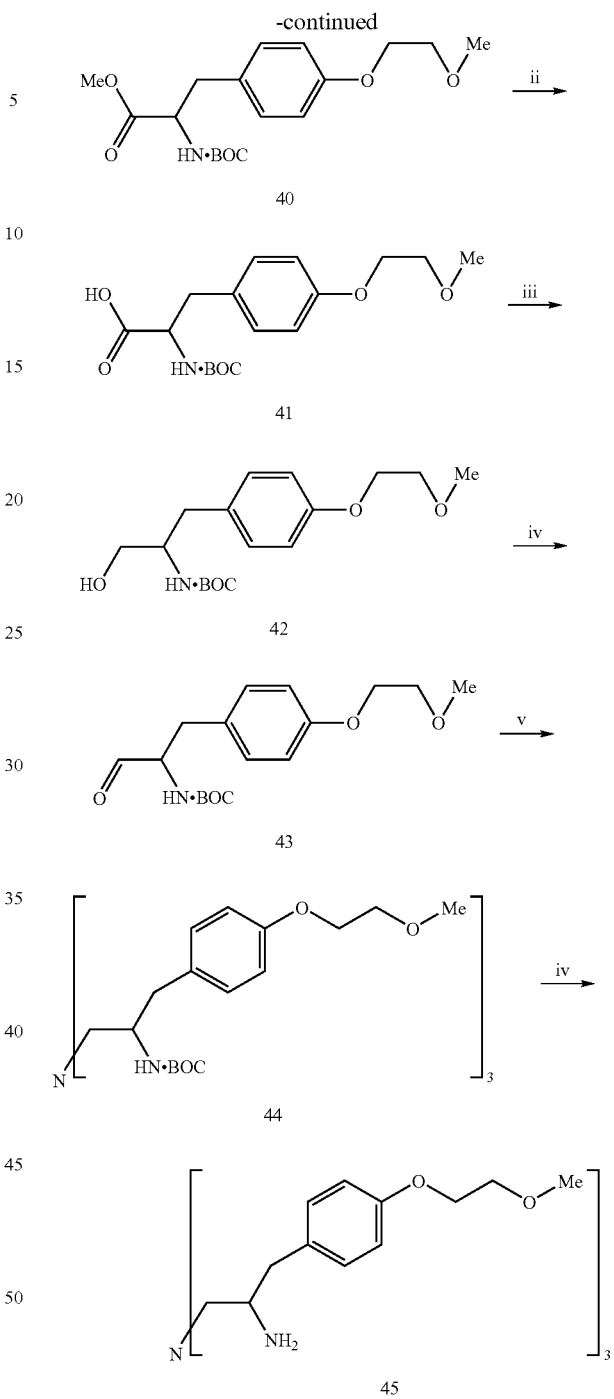

i) PEG-Cl, ii) KOH, iii) BH$_3$, iv) NaOCl, v) NaBH(OAc)$_3$, NH$_4$OAc, iv) HCl In Scheme 7, protected tyrosine derivative 39 is alkylated at the phenolic oxygen using an alkylene glycol halide, forming ether 40. The ester moiety of 40 is hydrolyzed, providing acid 41, the carbonyl moiety of which is reduced to CH$_2$, affording 42. The hydroxyl moiety of compound 42 is oxidized to the corresponding aldehydes by the action of NaOCl, providing 43. Trimer 44 is prepared by forming a Schiff base, which is subsequently reduced to the corresponding amine. Removal of the Boc protecting groups yields the amine scaffold 45.

Those of skill in the art will appreciate that the route set forth above can be practiced with substantially any substrate, including, but not limited to amino acids with side chains (e.g., cysteine, glutamic acid, lysine, serine, etc.), as well as other non-amino acid species.

Reactive Functional Groups

As discussed above, the complexes of the invention are tethered to other species by means of bonds formed between a reactive functional group on the ligand or a linker attached to the ligand, and a reactive functional group of complementary reactivity on the other species. For clarity of illustration the succeeding discussion focuses on the conjugation of representative ligands and complexes of the invention to polymers, including poly(ethers) and dendrimers, and to targeting agents for blood pool imaging. The focus exemplifies selected embodiments of the invention from which, others are readily inferred by one of skill in the art. No limitation of the invention is implied, by focusing the discussion on the representative embodiments.

Exemplary ligands and complexes of the invention bear a reactive functional group, which is generally located on the scaffold or on a substituted or unsubstituted alkyl or heteroalkyl chain attached to the scaffold or a chelating moiety, allowing their facile attachment to another species. A convenient location for the reactive group is the terminal position of the chain.

Reactive groups and classes of reactions useful in practicing the present invention are generally those that are well known in the art of bioconjugate chemistry. Currently favored classes of reactions available with reactive ligand analogues are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Exemplary reaction types include the reaction of carboxyl groups and various derivatives thereof including, but not limited to, N-hydroxysuccinimide esters, N— hydroxybenzotriazole esters, acid halides, acyl imidazoles, thioesters, p-nitrophenyl esters, alkyl, alkenyl, alkynyl and aromatic esters. Hydroxyl groups can be converted to esters, ethers, aldehydes, etc. Haloalkyl groups are converted to new species by reaction with, for example, an amine, a carboxylate anion, thiol anion, carbanion, or an alkoxide ion. Dienophile (e.g., maleimide) groups participate in Diels-Alder. Aldehyde or ketone groups can be converted to imines, hydrazones, semicarbazones or oximes, or via such mechanisms as Grignard addition or alkyllithium addition. Sulfonyl halides react readily with amines, for example, to form sulfonamides. Amine or sulfhydryl groups are, for example, acylated, alkylated or oxidized. Alkenes, can be converted to an array of new species using cycloadditions, acylation, Michael addition, etc. Epoxides react readily with amines and hydroxyl compounds.

Exemplary combinations of reactive functional groups found on a ligand of the invention and on a targeting moiety (or polymer or linker) are set forth in Table 2.

TABLE 2

| Chemical Functionality 1 | Chemical Functionality 2 | Linkage |
|---|---|---|
| Hydroxy | Carboxy | Ester |
|  | Hydroxy | Carbonate |
|  | Amine | Carbamate |
|  | $SO_3$ | Sulfate |
|  | $PO_3$ | Phosphate |
|  | Carboxy | Acyloxyalkyl |
|  | Ketone | Ketal |
|  | Aldehyde | Acetal |
|  | Hydroxy | Anhydride |
| Mercapto | Mercapto | Disulfide |
|  | Carboxy | Acyloxyalkyl Thioether |
|  | Carboxy | Thioester |
|  | Carboxy | Amino amide |
|  | Mercapto | Thioester |
|  | Carboxy | Acyloxyalkyl ester |
|  | Carboxy | Acyloxyalkyl amide |
|  | Amino | Acyloxyalkoxy carbonyl |
|  | Carboxy | Anhydride |
|  | Carboxy | N-acylamide |
|  | Hydroxy | Ester |
|  | Hydroxy | Hydroxymethyl ketone ester |
|  | Hydroxy | Alkoxycarbonyl oxyalkyl |
| Amino | Carboxy | Acyloxyalkylamine |
|  | Carboxy | Acyloxyalkylamide |
|  | Amino | Urea |
|  | Carboxy | Amide |
|  | Carboxy | Acyloxyalkoxycarbonyl |
|  | Amide | N-Mannich base |
|  | Carboxy | Acyloxyalkyl carbamate |
| Phosphate oxygen ester | Hydroxy | Phosphate |
|  | Amine | Phosphoramidate |
|  | Mercapto | Thiophosphate ester |
| Ketone | Carboxy | Enol ester |
| Sulfonamide | Carboxy | Acyloxyalkyl sulfonamide |
|  | Ester | N-sulfonyl-imidate |

One skilled in the art will readily appreciate that many of these linkages may be produced in a variety of ways and using a variety of conditions. For the preparation of esters, see, e.g., March supra at 1157; for thioesters, see, March, supra at 362-363, 491, 720-722, 829, 941, and 1172; for carbonates, see, March, supra at 346-347; for carbamates, see, March, supra at 1156-57; for amides, see, March supra at 1152; for ureas and thioureas, see, March supra at 1174; for acetals and ketals, see, Greene et al. supra 178-210 and March supra at 1146; for acyloxyalkyl derivatives, see, PRODRUGS: TOPICAL AND OCULAR DRUG DELIVERY, K. B. Sloan, ed., Marcel Dekker, Inc., New York, 1992; for enol esters, see, March supra at 1160; for N-sulfonylimidates, see, Bundgaard et al., J. Med. Chem., 31:2066 (1988); for anhydrides, see, March supra at 355-56, 636-37, 990-91, and 11 54; for N— acylamides, see, March supra at 379; for N-Mannich bases, see, March supra at 800-02, and 828; for hydroxymethyl ketone esters, see, Petracek et al. Annals NYAcad. Sci., 507:353-54 (1987); for disulfides, see, March supra at 1160; and for phosphonate esters and phosphonamidates.

The reactive functional groups can be chosen such that they do not participate in, or interfere with, the reactions necessary to assemble the reactive ligand analogue. Alternatively, a reactive functional group can be protected from participating in the reaction by the presence of a protecting group. Those of skill in the art will understand how to protect a particular functional group from interfering with a chosen set of reaction conditions. For examples of useful protecting groups, see Greene et al., PROTECTIVE GROUPS IN ORGANIC SYNTHESIS, John Wiley & Sons, New York, 1991.

Generally, prior to forming the linkage between the ligand and the targeting (or other) agent, and optionally, the linker group, at least one of the chemical functionalities will be activated. One skilled in the art will appreciate that a variety of chemical functionalities, including hydroxy, amino, and carboxy groups, can be activated using a variety of standard methods and conditions. For example, a hydroxyl group of the ligand (or targeting agent) can be activated through treatment with phosgene to form the corresponding chloroformate, or p-nitrophenylchloroformate to form the corresponding carbonate.

In an exemplary embodiment, the invention makes use of a targeting agent that includes a carboxyl functionality. Carboxyl groups may be activated by, for example, conversion to the corresponding acyl halide or active ester. This reaction may be performed under a variety of conditions as illustrated in March, supra pp. 388-89. In an exemplary embodiment, the acyl halide is prepared through the reaction of the carboxyl-containing group with oxalyl chloride. The activated agent is combined with a ligand or ligand-linker arm combination to form a conjugate of the invention. Those of skill in the art will appreciate that the use of carboxyl-containing targeting agents is merely illustrative, and that agents having many other functional groups can be conjugated to the ligands of the invention.

Macromolecular Complexes

In an exemplary embodiment, the invention provides a Gd(III) complex of the invention that is macromolecular, i.e., MW>1000 D. In one embodiment, a macromolecular complex of the invention is formed by covalently conjugating a complex to a macromolecule via a reactive functional group. In another embodiment, the macromolecular complex is formed by a non-covalent interaction between a complex and a macromolecule, e.g., a serum protein.

In the following discussion, the invention is described by reference to poly(ethylene glycol) adducts of homopodal and heteropodal ligands and chelates. Those of skill in the art will appreciate that the focus on poly(ethylene glycol) adducts is for clarity of illustration and does not limit the scope of the invention. Thus, the invention provides macromolecular complexes that include components derived from biomolecules and synthetic molecules. Exemplary biomolecules include polypeptides (e.g., antibodies, enzymes, receptors, antigens); polysaccharides (e.g., starches, inulin, dextran); lectins, non-peptide antigens and the like. Exemplary synthetic polymers include poly(acrylic acid), poly(lysine), poly(glutamic acid), poly(ethylene imine), etc.

Covalent Conjugation

Selection of an appropriate reactive functional group on a complex of the invention to form a desired macromolecular species is well within the abilities of one of skill in the art. Exemplary reactive functional groups of use in forming the covalent conjugates of the invention are discussed above. It is well within the abilities of one of skill to select and prepare a ligand of the invention having an appropriate reactive functional group of complementary reactivity to a reactive group on its conjugation partner.

In one embodiment, the bond formed between reactive functional groups of the macromolecule and that of the complex attaches the ligand to the macromolecule essentially irreversibly via a "stable bond" between the components. A "stable bond", as used herein, is a bond, which maintains its chemical integrity over a wide range of conditions (e.g., amide, carbamate, carbon-carbon, ether, etc.). In another embodiment, the macromolecule and the complex are linked by a "cleaveable bond". A "cleaveable bond", as used herein, is a bond that undergoes scission under selected conditions. Cleaveable bonds include, but are not limited to, disulfide, imine, carbonate and ester bonds. As discussed in the preceding sections, the reactive functional group can be located at one or more positions of the scaffold and/or one or more positions on the chelating ring structures.

Macromolecular Conjugates

The present invention also provides conjugates between the chelating agents and complexes of the invention and linear, branched and cyclic polymers, e.g., polysaccharides, poly(amino acids), cyclodextrins, synthetic polymers, etc.

Macromolecular Complexes with Increased Relaxivity

A promising route to the optimization of proton relaxivity involves increasing the rotational correlation time, $\tau_r$, by increasing the molecular weight of the complex, resulting in slower rotation of the molecule in solution. This has been achieved in a number of ways. Several groups have investigated polymer-based contrast agents in which a DTPA chelate is attached to a polymer such as polylysine, poly(ethylene glycol) or polydextran (Dresser, T. R. et al., *J. Magn. Reson. Imaging* 1994, 4, 467; Toth, E. H. et al., *Chem. Eur. J.* 1999, 5, 1202; Corot, C. S. et al., *D. Acta Radiologica* 1997, 38, 91). Improved (but modest) relaxivities are typically observed for these polymeric agents, reflecting the fast local motions within the polymer chain and the slow water exchange due to the poly(amino-carboxylate) chelate used. Such systems are being investigated for blood pool imaging, particularly as intravascular MRI contrast agents for myocardial perfusion (Casali, C. J. et al., *Acad. Radiol.* 1998, 5, S214).

Polysaccharides

The present invention provides conjugates between oxygen donor ligands and saccharides, e.g., polysaccharides. In an exemplary embodiment, the invention provides a conjugate between an oxygen donor chelate and inulin. Inulin is a naturally occurring polysaccharide which has been previously investigated as a carrier for Gd(III) chelates (using DTPA and DOTA derivatives) (Rongved, P. K., *J. Carbohydr. Res.* 1991, 214, 315; Corsi, D. M. V. E. et al., *Chem. Eur. J.* 2001, 7, 64). The attachment of 37 [Gd(DO3ASQ)] (SQ=squarate) units to a 25 chain length inulin polymer was recently reported (Corsi, D. M. V. E. et al., *Chem. Eur. J.* 2001, 7, 64). This resulted in a ca. nine-fold increase in $\tau_r$ (735 ps) which resulted in a relaxivity of 20.3 mM$^{-1}$ s$^{-1}$ (at 20 MHz and 37° C.). As with most derivatives of DTPA and DOTA, higher relaxivity was limited by a very slow $\tau_m$ (260 ns in this case).

The structure of inulin can be described as a mixture of linear β-(2→1)-linked α-D-fructofuranosyl chains with a α-D-glucopyranosyl unit at the terminal end. Inulin is commercially available in a variety of molecular weights and the degree of polymerization varies from 10 to 30, resulting in a molecular weight distribution of 1500 to 5000 Da. The high hydrophilicity, pH stability, low solution viscosity and biocompatability of inulin should ensure that the conjugated-MRI agent has favorable pharmacological properties.

In an exemplary embodiment, the inulin is attached to a TREN-HOPO scaffold. The bond is formed using an activated intermediate of a carboxylic acid derivative that is attached to the endocyclic nitrogen of a HOPY moiety. Other modes of conjugation are well within the skill of those of skill in the art. For example, similar molecules are readily synthesized using HOPO-TAM moieties in which the amide moiety of the TAM moiety is activated, and subsequently conjugated to inulin.

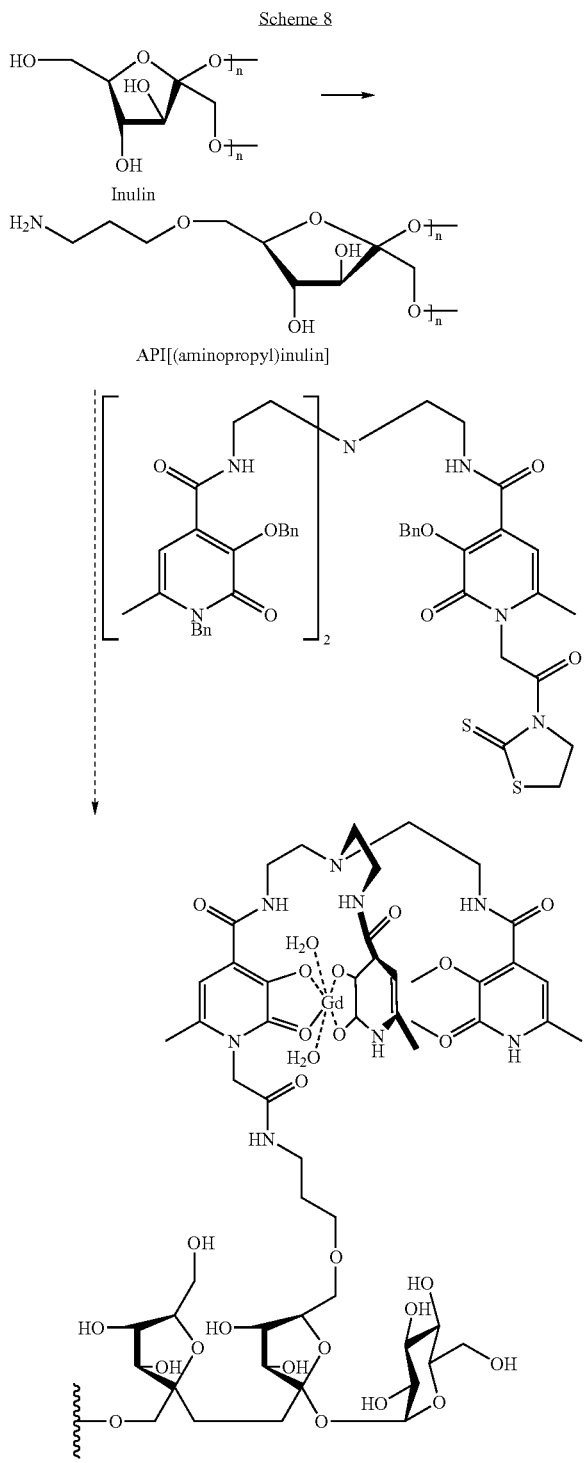

An exemplary synthetic scheme to attach TREN-6-Me-HOPO to the backbone of inulin is shown in Scheme 8. The flexibility of the polymer chain allows for the preparation of derivatives that have high degrees of substitution, facilitating a higher rigidity in the Gd(III) complex.

Also included in the present invention is a method of preparing a chelating agent having a polymeric backbone and at least one functionality to which a chelating ligand of the invention is bonded. Examples of suitable polymers include, but are not limited to, poly(styrene-divinylbenzene), agarose (manufactured by Bio-Rad Corp., Richmond, Calif., under the name "Affi-Gel"), and polyacrylamide. Those of skill in the art will appreciate that the method of the invention is not limited by the identity of the backbone species, and that numerous amine-, hydroxyl- and sulfhydryl-containing compounds are useful as backbones in practicing the method of the invention.

Dendrimer-Based Agents

In another aspect, the present invention provides a metal chelate as set forth above, which is attached to a dendrimer via a reactive functional group. Similar to the polymeric group discussed above, the dendrimer has at least two reactive functional groups. In one embodiment, one or more fully assembled ligand is attached to the dendrimer. Alternatively, the the chelate is formed directly on the dendrimer.

In contrast to linear polymers, dendrimers have a relatively rigid structure and the overall tumbling of the molecule contributes significantly to the rotational correlation time of the Gd—H vector. The high monodispersity, minimal shape variation and uniform surface chemistry of Gd(III) chelate dendrimers are also key features important in their potential application as MRI agents (Krause, W. et al., *Top. Curr. Chem.* 2000, 210, 261). Although the rotational correlation time increases with higher generation dendrimers, the increase in proton relaxivity eventually reaches a plateau, an effect which is attributed to the slow water exchange ($\tau_m$) inherent to the Gd(III) DTPA- and DOTA-based systems (Toth, E. et al., *Chem. Eur. J.* 1996, 2, 1607). Hence, the reported relaxivity values for dendrimer conjugates range from 11 to 36 $mM^{-1}s^{-1}$ per Gd(III) center, depending on the nature of the chelate and the dendrimer structure (Dong, Q. H. et al., *Invest. Radiol.* 1998, 33, 699; Wiener, E. C. B. et al., *Magn. Reson. Med.* 1994, 31, 1; Adam, G. et al., *Magn. Reson. Imaging* 1994, 4, 462; Margerum, L. D. et al., *J. Alloys Compd.* 1997, 249, 185; Bryant, L. H. et al., In *Proceedings of the 6th International Society of Magnetic Resonance in Medicine Conference*: Sydney, Australia, 1998).

Gd(III)-chelate-dendrimer conjugates have enhanced relaxivity due to their spherical rigid structure (which results in a slower $\tau_r$). According to the Enhanced Permeation and Retention Effect, high generation dendrimers of high molecular weight should be preferentially uptaken by tumor cells (Narayanan, V. V. et al., *Macromolecules* 2000, 33, 3944; Wiener, E. C. et al., *J. Am. Chem. Soc.* 1996, 118, 7774; Maeda, H. et al., *J. Controlled Release* 2000, 75, 271; Malik, N. et al., *J. Controlled Release* 2000, 65, 133). Previous work has shown, however, that the solubility of the macromolecular complex depends both on the properties of the Gd chelate and on the dendrimer itself (Cohen, S. M. et al., *Chem. Eur. J.* 2000, 6, 2). The highly water-soluble PAMAM dendrimers have yielded insoluble compounds upon functionalization with hydrophobic 1-Me-HOPO.

In an exemplary embodiment, a water-soluble and bio-adapted polyester (polypropionate) class of dendrimer contrast agents has been designed to provide favorable pharmacokinetic properties. See, for example, Ihre, H. et al., *Macromolecules* 1998, 31, 4061; Ihre, H. et al., *J. Am. Chem. Soc.* 1996, 118, 6388; Anders, H., Ihre, H., Patent WO/9900440 (Sweden)). In an exemplary embodiment, the termini of the dendrimers are conjugated to an oxygen donor ligand of the invention, e.g., TREN-1-Me-HOPO-TAM. The dendrimers are readily functionalized with thiaz-activated oxygen donor ligands, such as activated TREN-1-Me-HOPO-TAM ligands before complexation with $Gd^{3+}$ (Dong, Q. H. et al., *Invest. Radiol.* 1998, 33, 699).

Chelating Agents Containing PEG Functionalization

In another embodiment, the invention provides a complex, which includes a structure according to Formula I in which at least one of $R^1$, $R^2$, $R^3$, and $R^4$ comprise a moiety derived from poly(ethyleneglycol). In an exemplary embodiment, the invention provides derivatives of TREN-1-Me-3,2-HOPO-TAM, such as Gd-TREN-bis-(1-Me-HOPO)-(TAM-PEG-2000) (46); and Gd-TREN-bis-(1-Me-HOPO)-(TAM-PEG-5000) (47). A complex having a PEG of average molecular weight 450 was also prepared.

Figure 9:
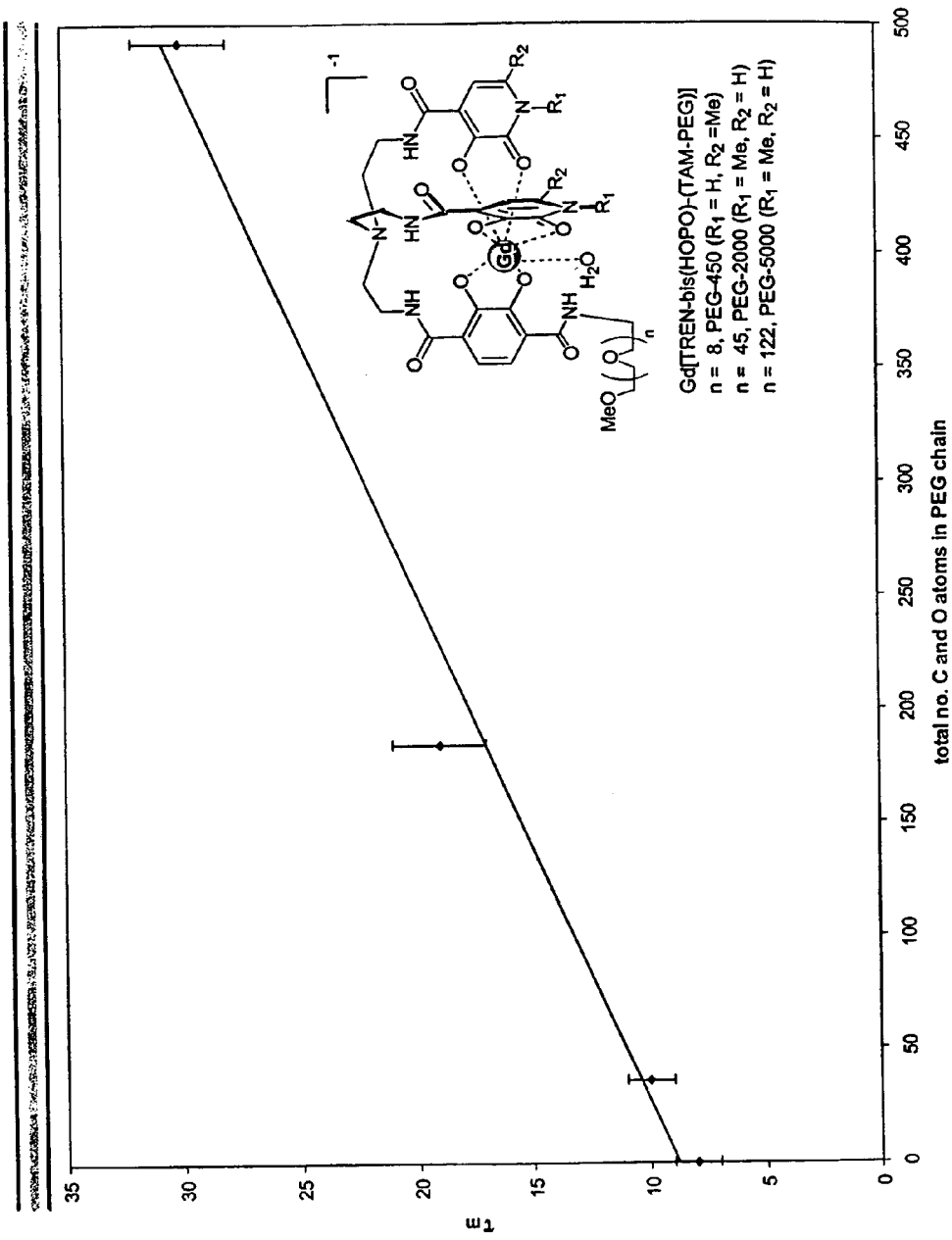
FIG. 9 is a graphical representation of the variation in $\tau_m$ with PEG length.

In the exemplary compounds above, PEG moieties of average molecular weights 2000 and 5000, respectively, were attached to the amide of the TAM moiety of a TREN-bis-(1-Me-HOPO)-(TAM). Both complexes were of high solubility in $H_2O$, allowing the water residence lifetime ($\tau_m$) to be determined by a variable temperature 17O NMR study of the transverse relaxation rate of $H_2^{17}O$. Significantly, there is an increase in $\tau_m$ as the PEG chain is lengthened, with values of approximately 8±1, 10±1, 19±2 and 31±2 ns for TREN-1-Me-3,2-HOPO-TAM, Gd-TREN-bis-(1-Me-HOPO)-(TAM-PEG-450) (48), Gd-TREN-bis-(1-Me-HOPO)-(TAM-PEG-2000) (46), Gd-TREN-bis-(1-Me-HOPO)-(TAM-PEG-5000) (47), respectively (FIG. 9). These values span a range that is considered optimal for achieving maximum values of proton relaxivity. The optimal value for $\tau_m$ depends on several variables, especially the field strength of the MRI scanner instrument. Thus the incorporation of PEG chains into HOPO-TAM ligands provides a method for the optimization of a MRI contrast agent to a particular field strength.

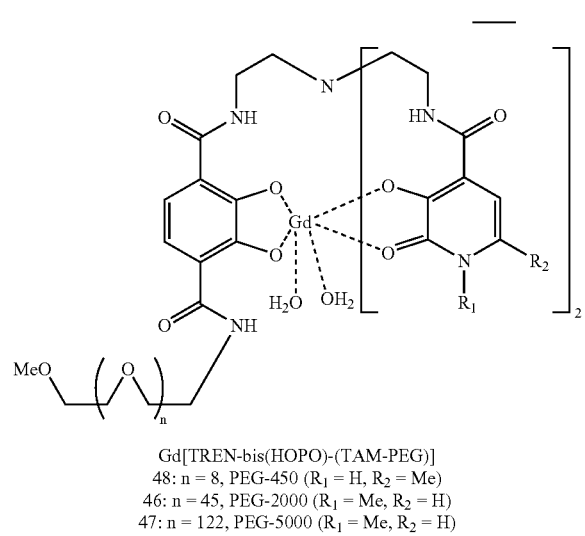

Gd[TREN-bis(HOPO)-(TAM-PEG)]
48: n = 8, PEG-450 ($R_1$ = H, $R_2$ = Me)
46: n = 45, PEG-2000 ($R_1$ = Me, $R_2$ = H)
47: n = 122, PEG-5000 ($R_1$ = Me, $R_2$ = H)

Figure 10:
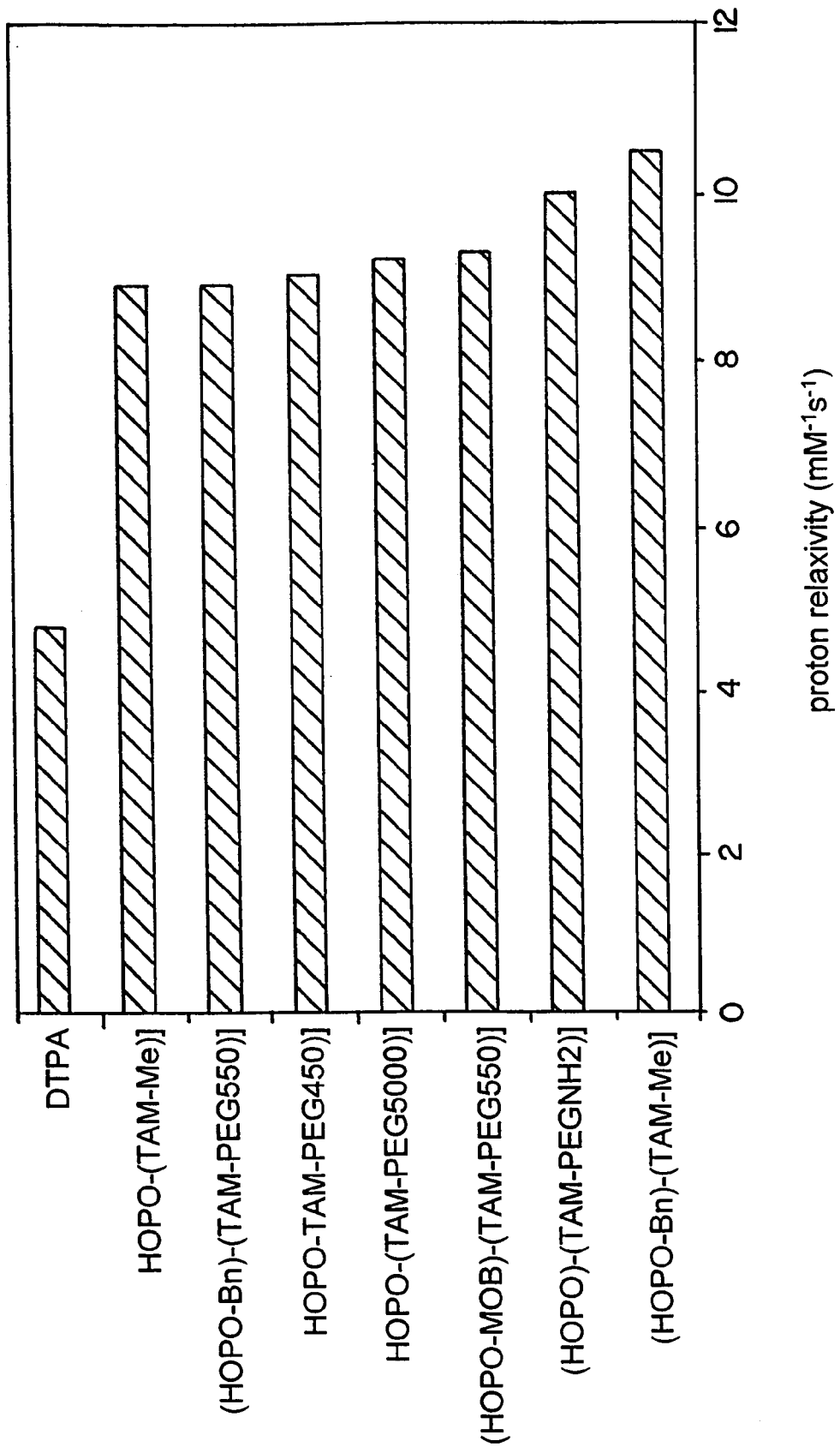
FIG. 10 is a graphical display of the relaxivities of various complexes of the invention.

In addition to systematically altering the $\tau_m$, the method of the invention provides for the optimization of additional parameters relevant to a MRI contrast agent. For example, the relaxivity of the core complexes is enhanced by their substitution with PEG (FIG. 10).

As will be apparent to those of skill in the art, the present invention provides compounds in which the PEG moiety is conjugated to positions other than the amide of a TAM group of a TREN-bis-(1-Me-HOPO)-(TAM). For example, the PEG moiety may be tethered to the endocyclic nitrogen or another position of the pyridinone moiety, another chelating moiety, the scaffold, or a combination of these positions.

Polyethylene glycol (PEG) is used in biotechnology and biomedical applications. The use of this agent has been reviewed (POLY(ETHYLENE GLYCOL) CHEMISTRY: BIOTECHNICAL AND BIOMEDICAL APPLICATIONS, J. M. Harris, Ed., Plenum Press, New York, 1992). Modification of enzymes (Chiu et al., *J. Bioconjugate Chem.*, 4: 290-295 (1993)), RGD peptides (Braatz et al., *Bioconjugate Chem.*, 4: 262-267 (1993)), liposomes (Zalipsky, S. *Bioconjugate Chem.*, 4: 296-299 (1993)), and CD4-IgG glycoprotein (Chamow et al., *Bioconjugate Chem.*, 4: 133-140 (1993)) are some of the recent advances in the use of polyethylene glycol. Surfaces treated with PEG have been shown to resist protein deposition and have improved resistance to thrombogenicity when coated on blood contacting biomaterials (Merrill, "Poly(ethylene oxide) and Blood Contact: A Chronicle of One Laboratory," in POLY(ETHYLENE GLYCOL) CHEMISTRY: BIOTECHNICAL AND BIOMEDICAL APPLICATIONS, Harris, Ed., Plenum Press, New York, (1992), pp. 199-220).

Many routes are available for attaching a chelate of the invention onto a polymeric or oligomeric species. See, for example, Dunn, R. L., et al., Eds. POLYMERIC DRUGS AND DRUG DELIVERY SYSTEMS, ACS Symposium Series Vol. 469, American Chemical Society, Washington, D.C. 1991; Herren et al., *J. Colloid and Interfacial Science* 115: 46-55 (1987); Nashabeh et al., *J. Chromatography* 559: 367-383 (1991); Balachandar et al., *Langmuir* 6: 1621-1627 (1990); and Burns et al., *Biomaterials* 19: 423-440 (1998).

Many activated derivatives of poly(ethyleneglycol) are available commercially and in the literature. It is well within the abilities of one of skill to choose, and synthesize if necessary, an appropriate activated PEG derivative with which to prepare a substrate useful in the present invention. See, Abuchowski et al. *Cancer Biochem. Biophys.*, 7:175-186 (1984); Abuchowski et al., *J. Biol. Chem.*, 252: 3582-3586 (1977); Jackson et al., *Anal. Biochem.*, 165: 114-127 (1987); Koide et al., *Biochem Biophys. Res. Commun.*, 111: 659-667 (1983)), tresylate (Nilsson et al., *Methods Enzymol.*, 104: 56-69 (1984); Delgado et al., *Biotechnol. Appl. Biochem.*, 12: 119-128 (1990)); N-hydroxysuccinimide derived active esters (Buckmann et al., *Makromol. Chem.*, 182: 1379-1384 (1981); Joppich et al., *Makromol. Chem.*, 180: 1381-1384 (1979); Abuchowski et al., *Cancer Biochem. Biophys.*, 7: 175-186 (1984); Katreet al. *Proc. Natl. Acad. Sci. U.S.A.*, 84: 1487-1491 (1987); Kitamura et al., *Cancer Res.*, 51: 4310-4315 (1991); Boccu et al., *Z. Naturforsch.*, 38C: 94-99 (1983), carbonates (Zalipsky et al., POLY(ETHYLENE GLYCOL) CHEMISTRY: BIOTECHNICAL AND BIOMEDICAL APPLICATIONS, Harris, Ed., Plenum Press, New York, 1992, pp. 347-370; Zalipsky et al., *Biotechnol. Appl. Biochem.*, 15: 100-114 (1992); Veronese et al., *Appl. Biochem. Biotech.*, 11: 141-152 (1985)), imidazolyl formates (Beauchamp et al., *Anal. Biochem.*, 131: 25-33 (1983); Berger et al., *Blood*, 71: 1641-1647 (1988)), 4-dithiopyridines (Woghiren et al., *Bioconjugate Chem.*, 4: 314-318 (1993)), isocyanates (Byun et al., *ASAIO Journal*, M649-M-653 (1992)) and epoxides (U.S. Pat. No. 4,806,595, issued to Noishiki et al., (1989). Other linking groups include the urethane linkage between amino groups and activated PEG. See, Veronese, et al., *Appl. Biochem. Biotechnol.*, 11: 141-152 (1985).

The PEG group is preferred for two reasons. First, the high water-solubility associated with PEG chains increases the rather low solubility of the parent complexes. Second, although it has been previously found that rapid internal motions within a PEG chain result in only a modest increase in $\tau_r$(Toth, E. et al., *Magn. Reson. Chem.* 1998, 36, S125), it has also been demonstrated that PEG chains can bind to HSA across a wide pH range (Azegami, S. T. et al., *Langmuir* 1999, 15, 940). The value of relaxivity observed for the HSA complex is considerably higher than any other relaxivities (per $Gd^{III}$ center) reported to date, reflecting an optimized water exchange rate and a slow rotational correlation time. Therefore, this non-covalent interaction to effect an increase in $\tau_r$ and relaxivity has been exploited in the present invention.

Biospecific Contrast Agents

The development of MRI agents with higher tissue/organ specificity is seen as a large part of the future of magnetic resonance imaging (Caravan, P. E. et al., *Chem. Rev.* 1999, 99, 2293). Methods of enhancing the specificity of agents include, but are not limited to, attaching the signal generating portion of the agent (e.g., an oxygen donor ligand complex with Gd(III)) to a species that actively directs the conjugate to a selected tissue. Exemplary active agents are antibodies and ligands for biologically relevant receptors. Another approach to improving the biodistribution of an agent relies on preparing an agent that interacts passively (non-specifically) with a biologically relevant species, e.g., a serum protein. Yet another strategy exploits the enhanced permeability and uptake mechanism in which a damaged or diseased tissue preferentially uptakes a macromolecular agent.

In an exemplary embodiment, the present invention provides an agent that binds to serum proteins in vivo, thus, affording a blood pool contrast enhancing agent. A second advantage accrues from the interaction between the oxygen donor-metal complexes of the invention and a serum protein; the rotational correlation time of the complex increases, leading to an increase in the relaxivity of the complex (Lauffer, R. B., *Magn. Reson. Med.* 1991, 22, 339).

In vivo binding to a macromolecule allows the Gd(III) complex to take on a rotational correlation time that is similar to that of the macromolecule, leading to a dramatic increase in relaxivity. Additionally, the binding causes an increased concentration and retention of the Gd(III) complex in the localized region of the biomolecule. Furthermore, the relaxivity of the bound complex is much greater than that of the unbound complex, which leads to a high target-to-background ratio.

The complex MS-325 forms a noncovalent adduct with the blood protein human serum albumin (HSA) (Parmalee, D. J. W. et al., *Invest. Radiol.* 1997, 32, 741; Lauffer, R. B. P. et al., *Radiology* 1998, 207, 529). The relaxivity of the resulting HSA adduct is 42.0 $mM^{-1}s^{-1}$, which is nearly seven times greater than the in vitro relaxivity of the free complex in water (6.6 $mM^{-1}s^{-1}$). MS-325 is currently in phase II and phase III clinical trials for imaging the cardiovascular system. Complexes have also been designed to target other macromolecules. For example, Gd-BOPTA was designed to target hepatocytes in order to facilitate hepatobiliary imaging (Cavanga, F. M. et al., *Invest. Radiol.* 1997, 32, 780). This MRI contrast agent has a relaxivity of 4.4 $mM^{-1}s^{-1}$ in water, 6.9 $mM^{-1}s^{-1}$ in rat plasma and 30 $mM^{-1}s^{-1}$ in rat hepatocytes.

Despite the success of second-generation contrast agents such as MS-325 and Gd-BOPTA, there still remains a considerable difference between relaxivities that have been achieved and the maximum relaxivities that are theoretically possible. The primary reason for this is the slow water exchange rates at the Gd(III) center. Optimal water residence times ($\tau_m$) have been estimated to be a few tens of nanoseconds (Aime, S. B. et al., *Chem. Soc. Rev.* 1998, 27, 19), with the exact value depending on several variables, including the magnetic field strength of the MRI scanner. The water residence lifetimes of commercial contrast agents are typically 100-1000 ns, which is far slower than optimal. Although this will not limit the relaxivity of small, fast-tumbling molecules to a great extent, the effect becomes much more significant for molecules of long rotational correlation time (Toth, E. H. et al., *Chem. Eur. J.* 1999, 5, 1202). All macromolecular contrast agents in use or under development incorporate the same basic DTPA, DTPA-BMA or DOTA chelate, resulting in slow water exchange and relatively modest proton relaxivities.

The present invention provides slowly tumbling Gd(III) complexes with faster water exchange rates (i.e. with $\tau_m$ and $\tau_r$ preferably in the low ns regime). The invention also provides MRI contrast agents with desirable in vivo persistence, which facilitate diagnosis of physiological abnormalities in specific regions of the body over longer periods than currently possible. In the process of optimizing biomolecule affinity, $\tau_r$, and $\tau_m$, other essential characteristics (such as stability and water-solubility) have not be worsened. Therefore, the new MRI contrast agents, which are the subject of this invention, contain the requisite structural features that result in images with better morphological and functional information (Comblin, V. et al., *Coord. Chem. Rev.* 1999, 185-186, 451).

In an exemplary embodiment, the complexes of the invention include the covalent attachment of substituents to the oxygen donor ligand core, which facilitate non-covalent interactions with endogenous biomolecules. Along with greater specificity in diagnosis, the binding of a slowly rotating macromolecule to the contrast agent allows for longer rotational correlation times in vivo, which could dramatically increase the relaxivity.

Blood Pool MRI Contrast Agents

The present invention is exemplified by reference to blood pool contrast agents. The residence of the complexes of the invention in the blood pool is influenced by a number of structural features. For example, the molecular size (weight) of the complexes of the invention is readily increased to a value that prevents their rapid elimination by glomerular filtration. The increase in molecule size can be achieved by attaching a macromolecular moiety to the ligand. Alternatively, an array of ligands may be attached to a macromolecular carrier, such as a poly(peptide), poly(saccharide), or a dendrimer or other synthetic polymer. In general it is preferred that the resulting construct is biocompatible, substantially non-immunogenic, water-soluble and has an acceptable relaxivity. When the ligands (or complexes) of the invention are attached to a macromolecular species, the attachment can be through a stable linkage or a linkage that is cleaved under biologically relevant conditions. Cleaveable linkages include a cleaveable group as discussed herein. Strategies for preparing biodegradable contrast agents are known in the art. See, for example, U.S. Pat. No. 6,312,664.

Another strategy for enhancing the blood pool residence time of a chelate of the invention relies on the non-covalent, reversible interaction between the chelate and a component of the blood, for example, a protein.

Human serum albumin (HSA) is an attractive target for blood pool imaging as it constitutes 4.5% of plasma and is the most abundant protein in serum. Binding of the MRI contrast agent to HSA serves three purposes. First, it targets the complex to the blood pool allowing selective enhancement of arteries and veins during MR angiographic evaluations. Second, protein binding slows down the molecular tumbling time of the complex and should provide a 5- to 10-fold increase in relaxation enhancement as compared to the parent complex (Caravan, P. et al., *Inorg. Chem.* 2001, 40, 2170). Finally, albumin binding increases the half-life of the drug in vivo, which allows the radiologist time to image multiple body regions and to employ pulse sequences which give high resolution images. However, HSA possesses numerous binding sites of different levels of hydrophobicity and hydrophilicity, hence, different affinities for small molecules (FIG. 11). The warfarin binding site (in subdomain IIA of HSA) is one such cavity and a recent study (Zaton, A. M. L. V., J. P. *Chem.-Bio. Int.* 2000, 124, 1) has shown that 4-hydroxycoumarin (CMN)

has a very high affinity for this site in comparison with structural analogues and uracils (pyrimidine derivatives). The synthetic scheme the attachment of CMN to TREN-6-Me-HOPO is shown in Scheme 9.

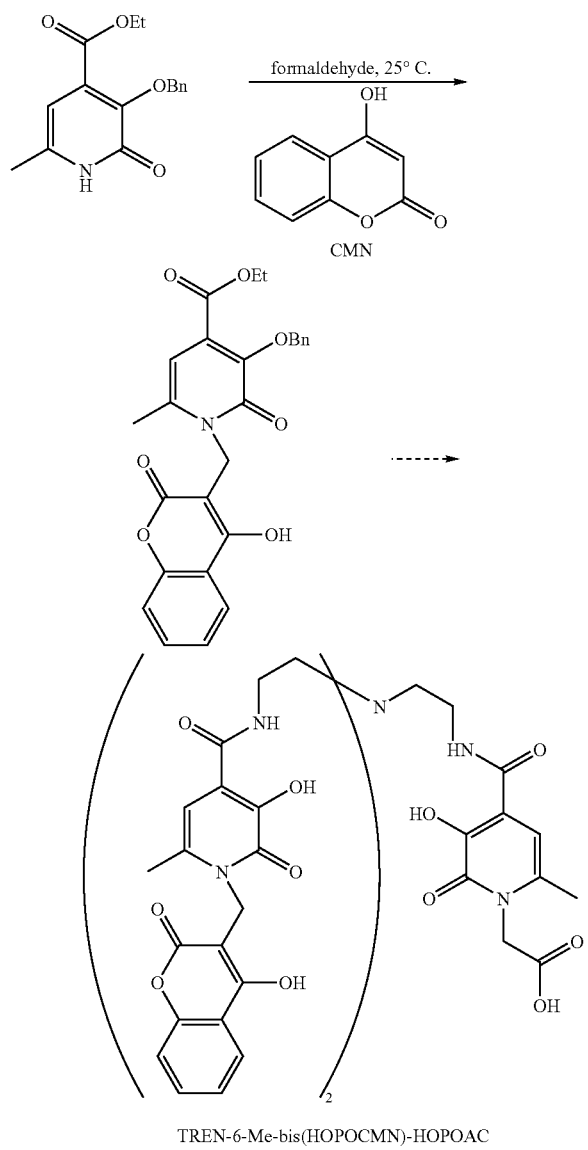

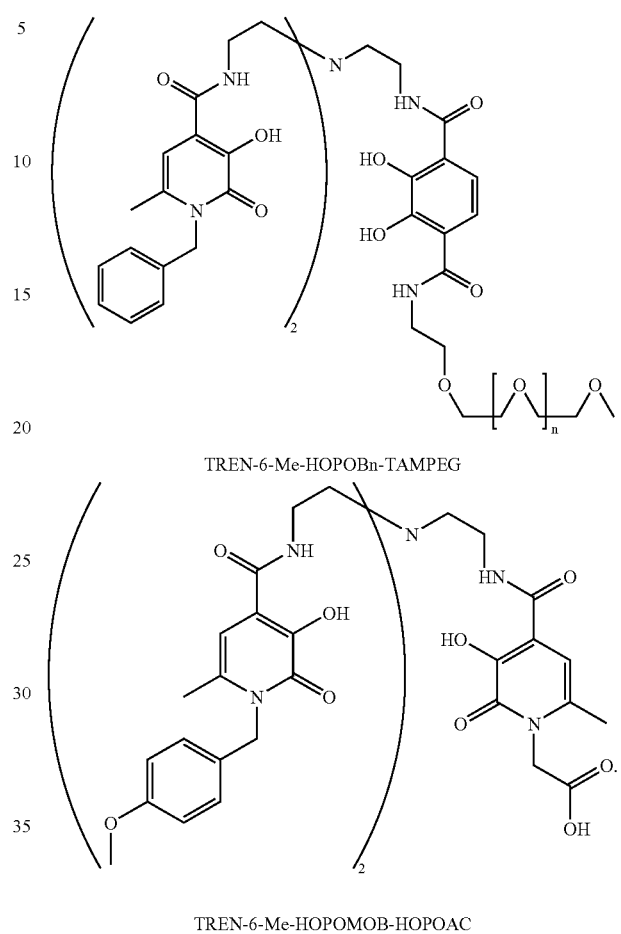

TREN-6-Me-HOPOBn-TAMPEG

TREN-6-Me-HOPOMOB-HOPOAC

TREN-6-Me-bis(HOPOCMN)-HOPOAC

In Scheme 9, the protected HOPO derivative is combined with hydroxy-coumarin in the presence of formaldehyde to form the protected coumarin-HOPO adduct. The adduct is subsequently reacted with an amine backbone as discussed herein and, optionally, with another chelating moiety, such as a HOPO substituted on the endocyclic nitrogen with an acetic acid residue. The benzyl protecting groups are optionally removed after the synthesis of the ligand is complete.

Figure 12:
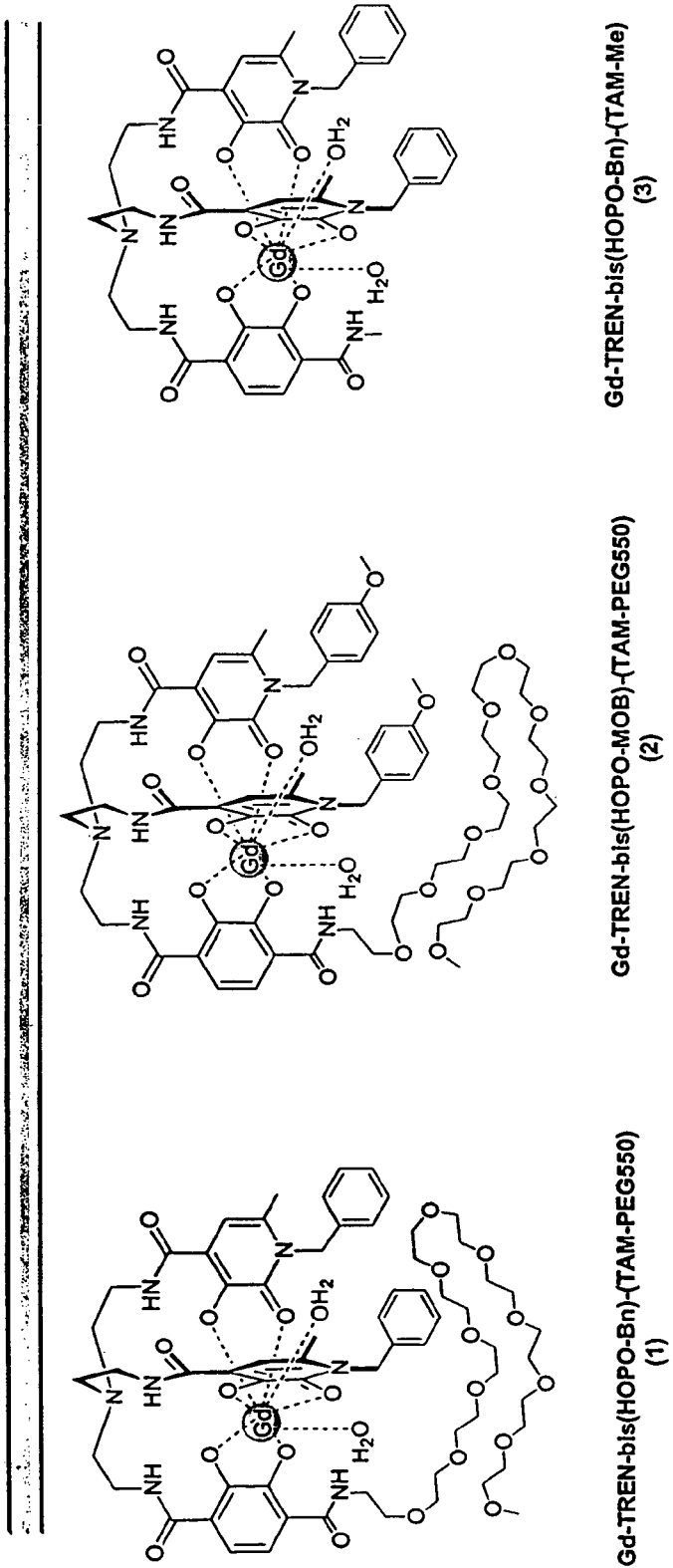
FIG. 12 displays structures of exemplary protein binding chelates of the invention.
Figure 13:
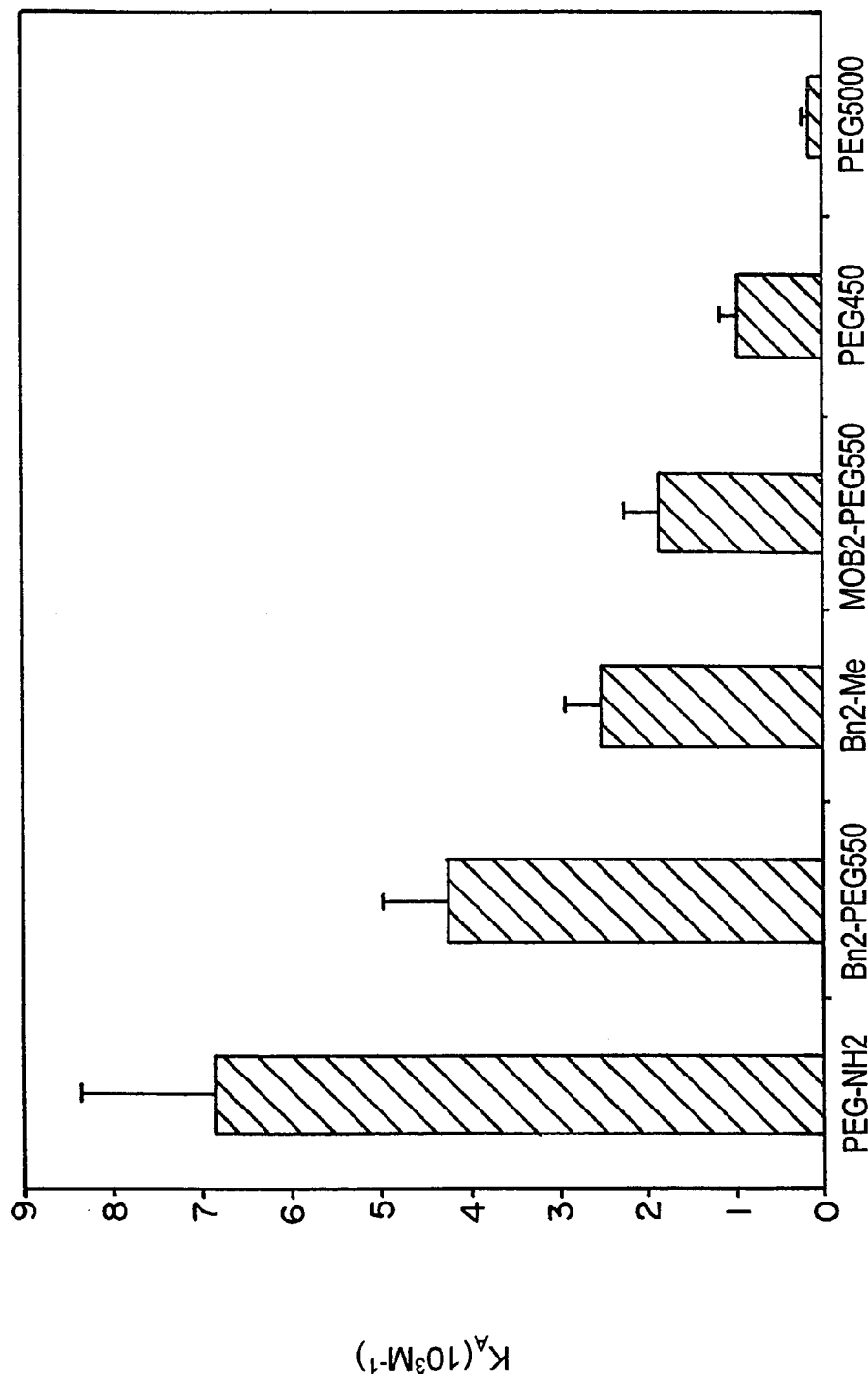
FIG. 13 is a graphical representation of the variation in the affinity of complexes of the invention for human serum albumin as the hydrophobicity/hydrophilicity of the complex is varied indicating that the invention provides a method to systematically vary the degree and strength of binding of a complex to a serum protein.
Figure 14:
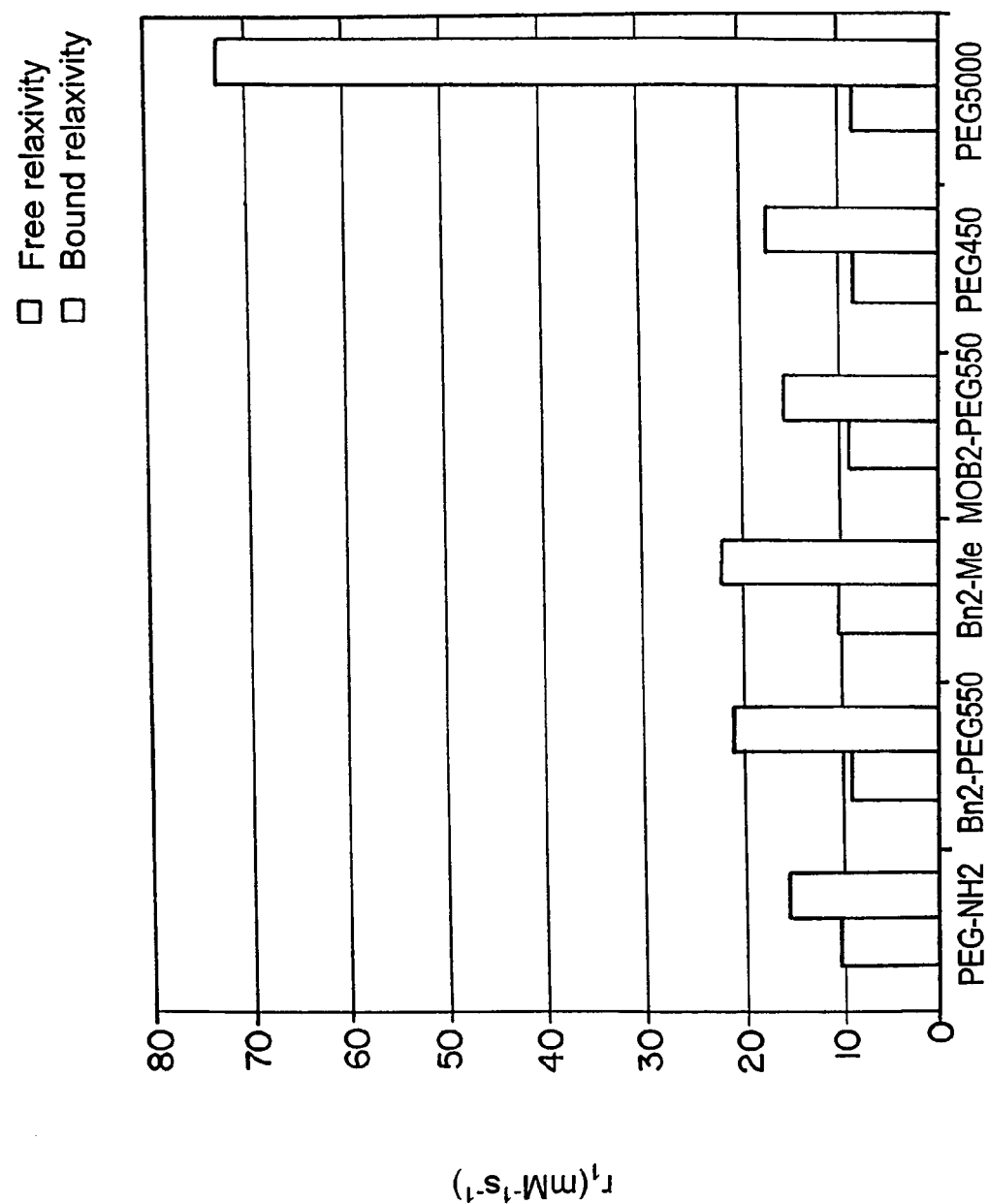
FIG. 14 is a graphical representation of the variation in the relatxation of complexes of the invention bound to human serum albumin as the hydrophobicity/hydrophilicity of the complex is varied indicating that the invention provides a method to systematically vary the relaxivity of the complex based on the degree and strength of binding of a complex to a serum protein.
Figure 15:
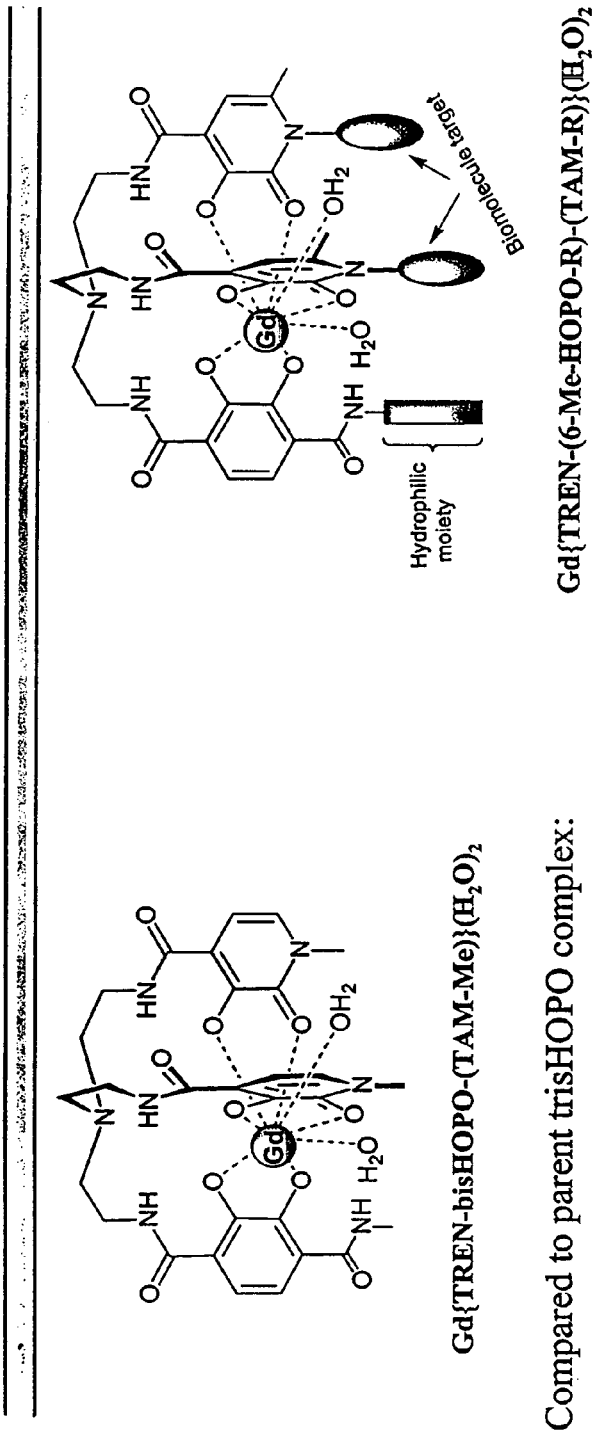
FIG. 15 displays structures of motifs of protein binding complexes of the invention.

Other exemplary HSA-binding ligands of the invention include a hydrophilic moiety and a hydrophobic group, e.g., a benzyl group (FIG. 12). In one embodiment, the hydrophilic group is PEG. In another representative embodiment, the hydrophilic group is a species such as a carboxylic acid. Presently preferred hydrophobic moieties include substituted or unsubstituted benzyl groups. Representative ligands according to this motif include:

It has been found that the affinity of the complex for HSA is modulated by varying the structure of the PEG substituent (FIG. 13). Complex binding to HSA enhances the relaxivity of the complex (FIG. 14). The hydrophobic and hydrophilic moieties may be attached to the same or different chelating subunits (FIG. 15).

Attachment of benzyl (Bn) or para-methoxy-benzyl (MOB) groups to the pyridine nitrogen of the 6-Me-HOPO scaffold is readily accomplished according to Scheme 10.

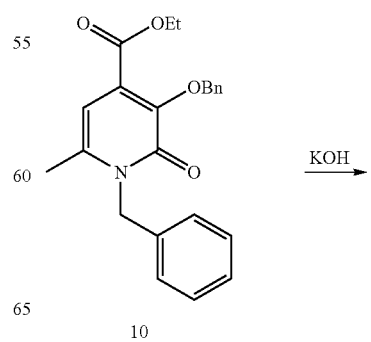

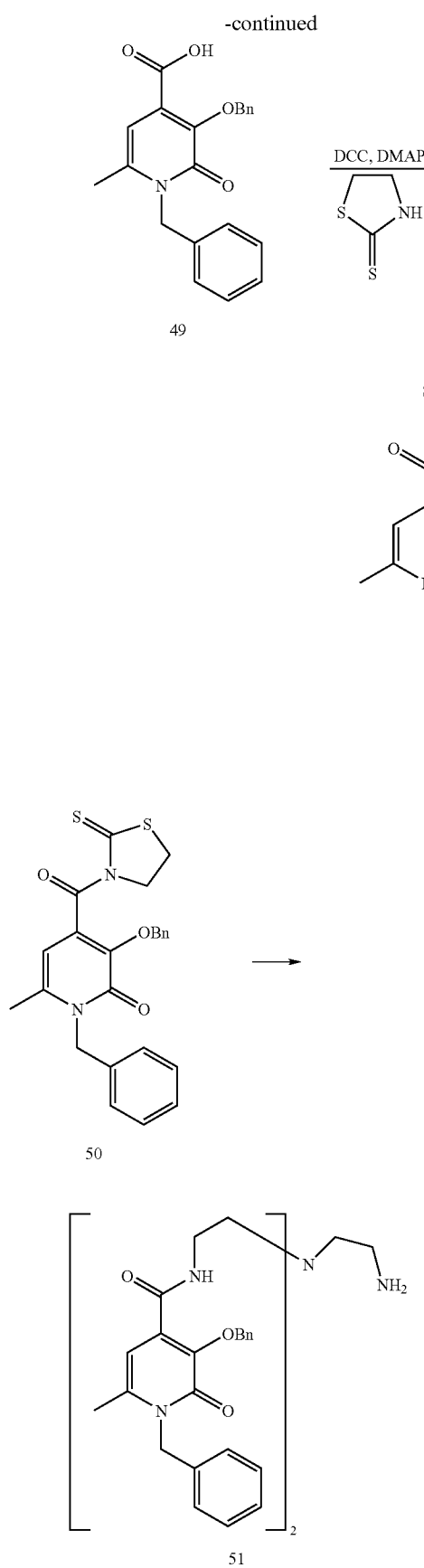
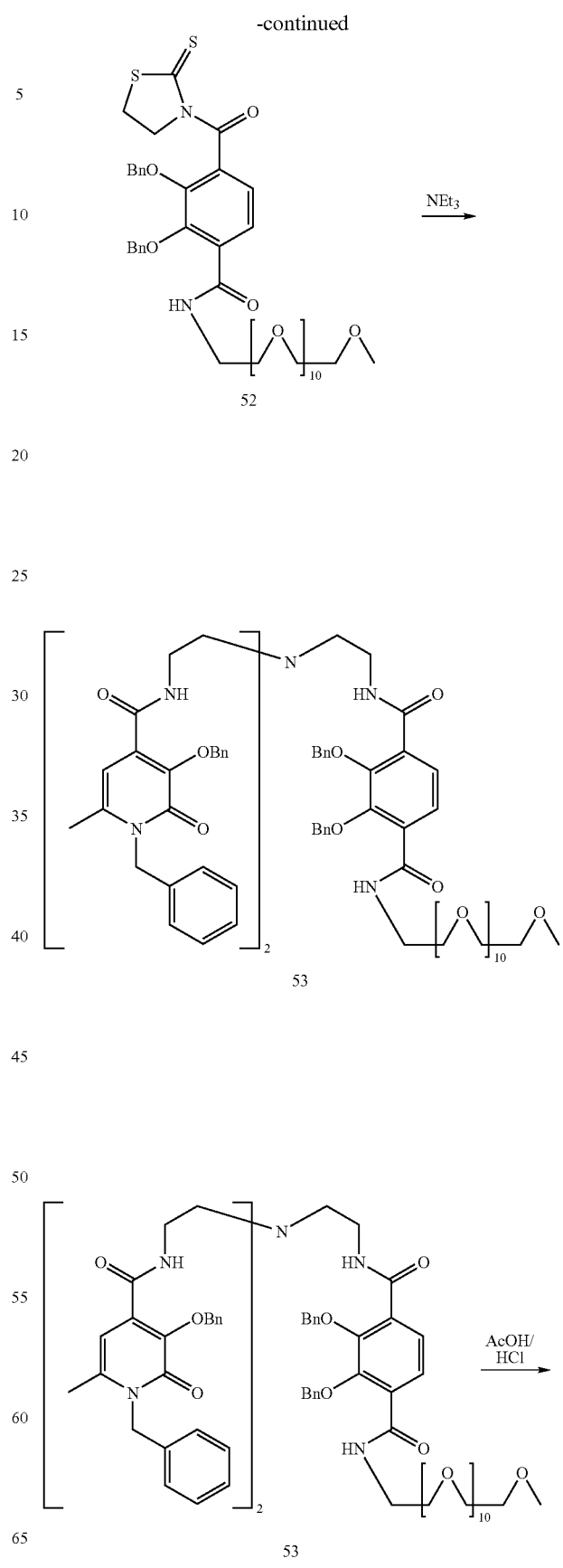

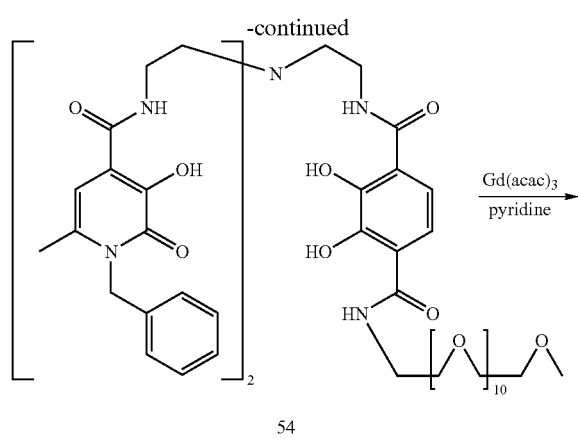

54

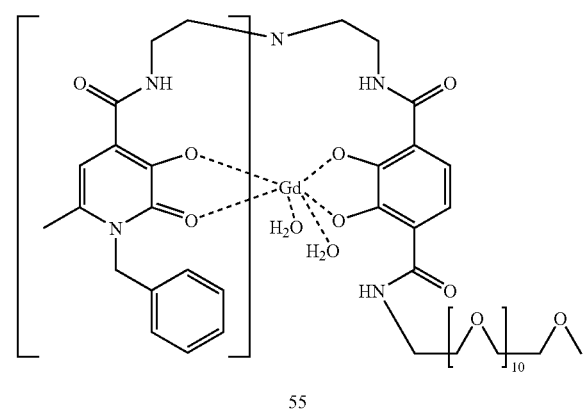

55

In Scheme 10, the ethyl ester (10) is hydrolyzed to the corresponding acid 49, which is converted to thiazolide 50. Two thiazolide units are coupled to the TREN backbone, affording a ligand having a free amine group 51 to which is coupled a protected PEG-TAM derivative 52. The resulting heteropodal ligand 53 is debenzylated, liberating the phenolic hydroxl moieties of the TAM subunit. The resulting compound 54 is metallated to provide Gd(III) chelate 55.

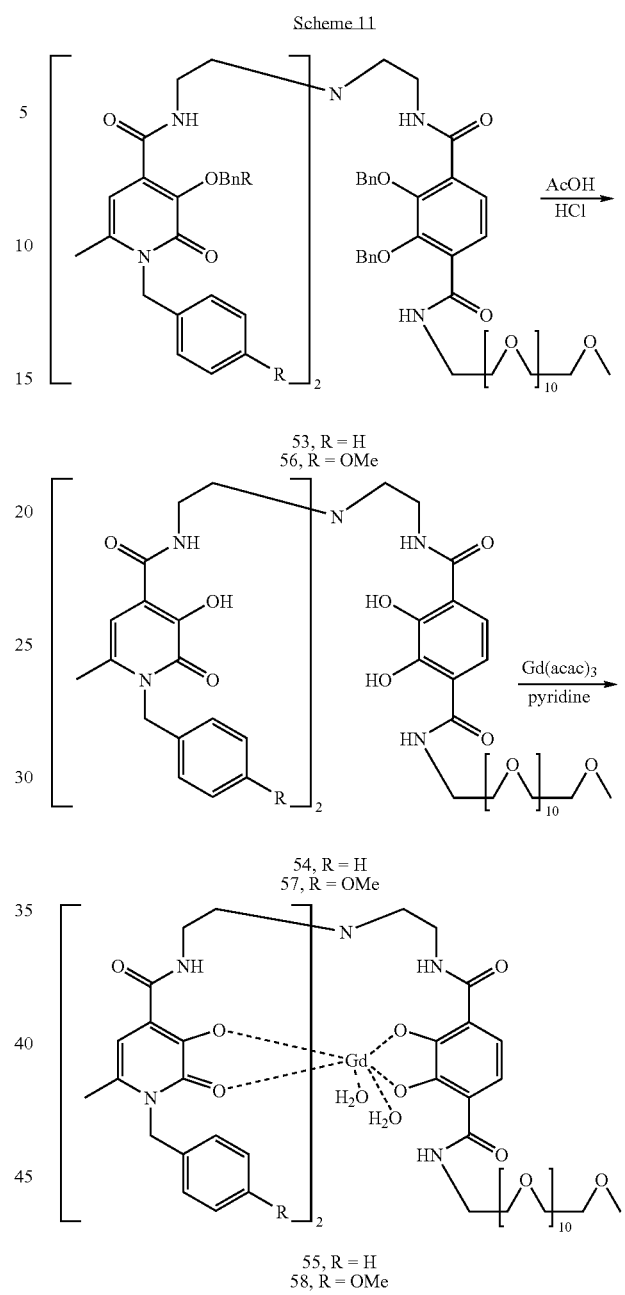

As shown in Scheme 11, the method of Scheme 10 is equally applicable to the preparation of oxygen donor ligands in which the benzyl group is substituted.

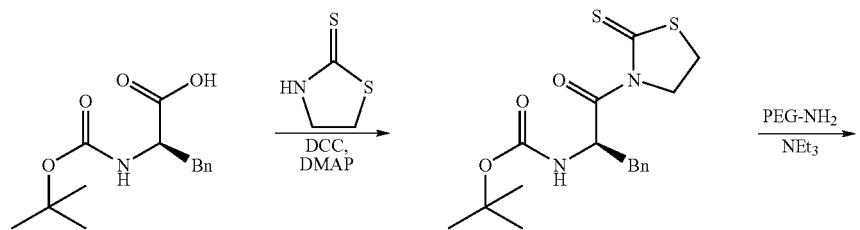

-continued

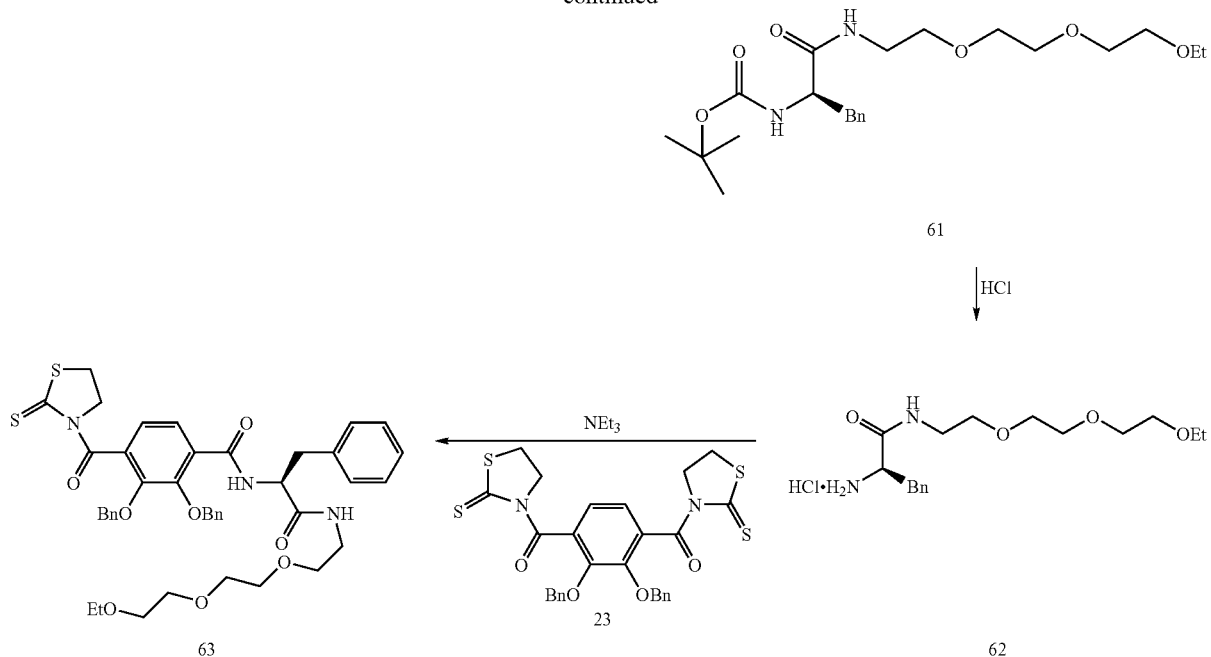

Scheme 12 sets forth the synthesis of thiaz-TAM-(L)Phen-TRI, which is used to form oxygen donor ligands of the invention. Thus, N-protected phenylalanine 59 is activated as the thiazolide 60, which is coupled to an amino-PEG, affording PEGylated phenylalanine 61. The BOC protecting group is then cleaved yielding the amine 62. Compound 62 is coupled to di-thiaz-TAM 23, to provide compound 63, having both hydrophobic and hydrophilic characteristics. Compound 63 is coupled to a ligand scaffold (such as 24) as discussed above.

The Gd complexes of the invention interact with HSA. It is within the scope of the invention to vary the substituents on the oxygen donor ligand to adjust the water solubility of the complex. Furthermore, the linker between the protein binding moiety and the Gd chelate can be adjusted to tune the degree of protein-ligand interaction.

Liver-Specific MRI Agents

The invention also provides complexes that are targeted to the liver and/or other components of the reticuloendothelial system. In an exemplary embodiment, the complex includes a hydrophobic moiety or other group known to be preferentially taken up by the liver or other components of the reticuloendothelial system. For example, a direct route to liver-specific MRI agents is to take advantage of the known biodistribution of cholesterol. Cholesterol is a biomolecule that is synthesized in the liver and metabolized in the liver and bile glands.

In an exemplary embodiment a cholesterol derivative, e.g., cholic acid (CHOL) is attached to the TREN-HOPO-TAM scaffold (Scheme 13). This attachment enables specific in vivo localization of the conjugated-MRI agent to tissue of the reticuloendothelial system (Anelli, P. L. et al., *Bioconj. Chem.* 1999, 10, 137; Anelli, P. L. et al., *Acta Radiologica* 1997, 38, 15) resulting in hepatobiliary contrast enhancement. The noncovalent binding of [Gd(TREN-HOPOAC-TAM-CHOL)(H$_2$O)$_2$]$^{-1}$ to hepatocytes also results in slower tumbling of the molecule resulting in a higher proton relaxivity. Cholic acid is non-toxic and is not expected to be cleaved from the MRI agent while in the liver (Anelli, P. L. et al., *Bioconj. Chem.* 1999, 10, 137; Anelli, P. L. et al., *Acta Radiologica* 1997, 38, 15).

Scheme 13

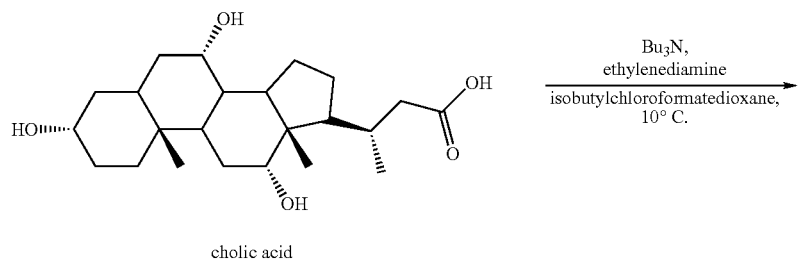

cholic acid

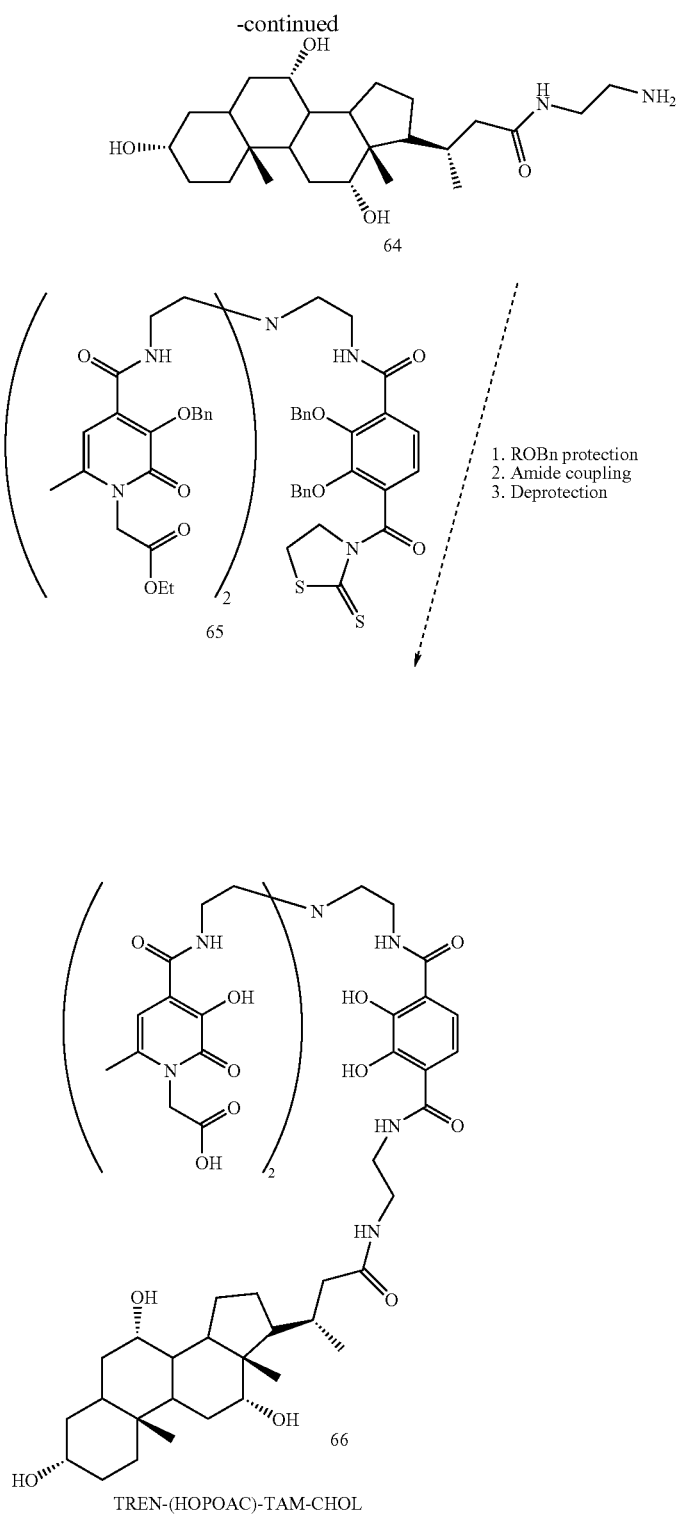

TREN-(HOPOAC)-TAM-CHOL

In Scheme 13, cholic acid is activated and converted to the ethylamine derivative 64 by treating the activated intermediate with ethylenediamine. Intermediate 64 is combined with an active thiazolide derivative of a ligand of the invention 65, to form the corresponding cholesterol derivatized ligand 66.

In another exemplary embodiment, the invention provides liver-selective complexes that include both a poly(ether) and a hydrophobic moiety, such as a cholesterol derivative. A representative synthetic route is provided in Scheme 14.

Scheme 14

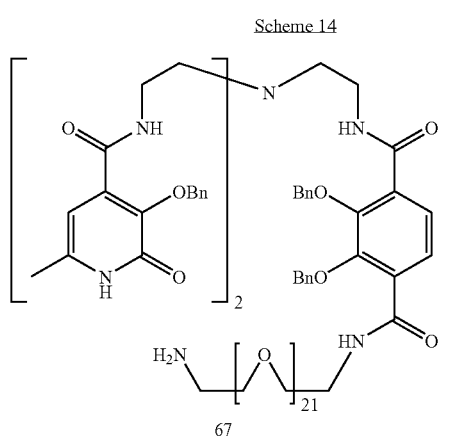

67

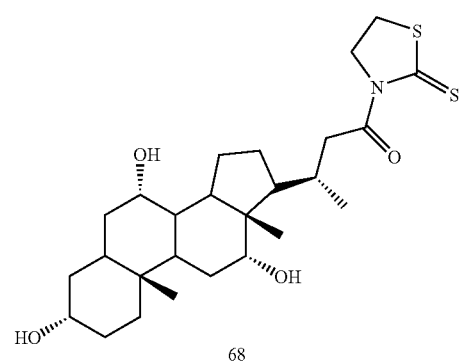

68

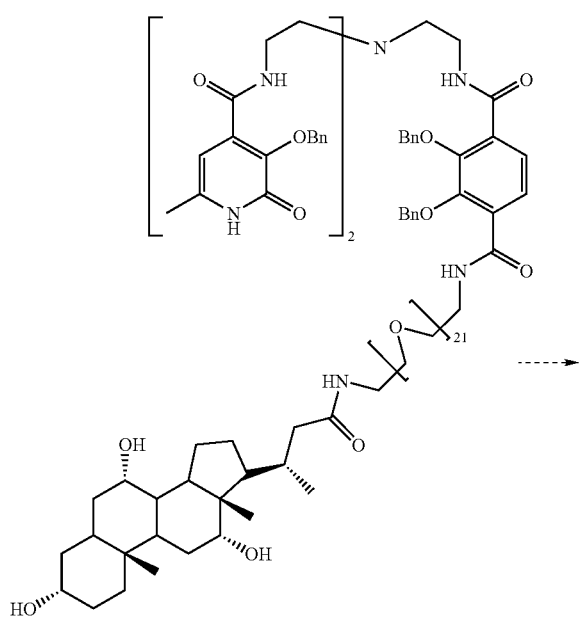

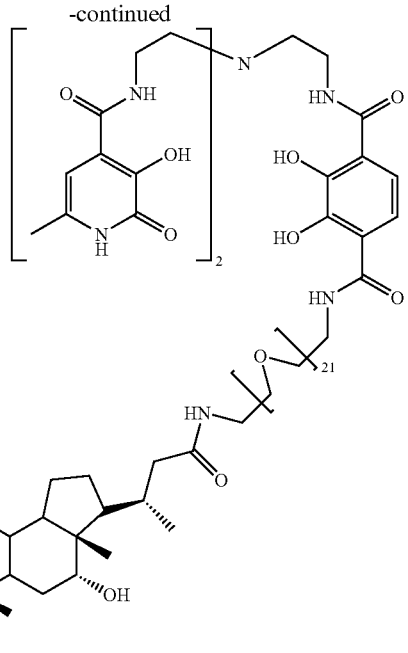

In Scheme 14 a ligand functionalized with a poly(ether) terminating with an active amine 67 is combined with activated cholesterol thiazolide 68 to provide the bifunctionalized ligand, bearing both a poly(ether) and a cholesterol moiety 69. Following the formation of the bifunctionalize ligand, the benzyl protecting groups are removed from the phenolic oxygens of the TAM moiety, affording ligand 70.

Tumor Selective Agents

The present invention also provides agents that are selective for tumors. In an exemplary embodiment, the invention provides a gadolinium chelate conjugated to a sapphyrin. Sapphyrins, which are expanded porphyrins, have been studied extensively for use in medicinal applications as anion binders and photosensitizers and have also been studied in cancer models to target tumors of pancreatic adenocarcinoma (constituting more than 75% of all pancreatic cancer). Therefore, the combination of pancreas specificity of porphyrins, (cheap and readily available for screening) and expanded porphyrins, and the fast water exchange rate of the chelates of the invention can be combined to give promising pancreas-selective and fast water exchanging Gd-TREN-HOPO-porphyrin agents.

Pancreatic cancer most often occurs in the form of pancreatic adenocarcinoma. Very recent and exciting research shows that a water-soluble derivative of sapphyrin accumulates specifically in human pancreatic adenocarcinoma when transplanted into and grown in mice (Ferucci. J. T. *Annals of Oncology* 10, Suppl. 4: S18 (1999)). In this study, thin cross-sections of tissue were analyzed by UV and resonance Raman spectroscopy for the sapphyrin, which was found to be present in the tumor in large quantities at all post-injection times. At the maximum tumor concentration, pancreatic tumor selectivity is hundreds of times greater than that for the liver, kidney or muscle tissues in the mouse model.

An exemplary synthesis of the compounds of the invention is set forth in Scheme 15.

Scheme 15
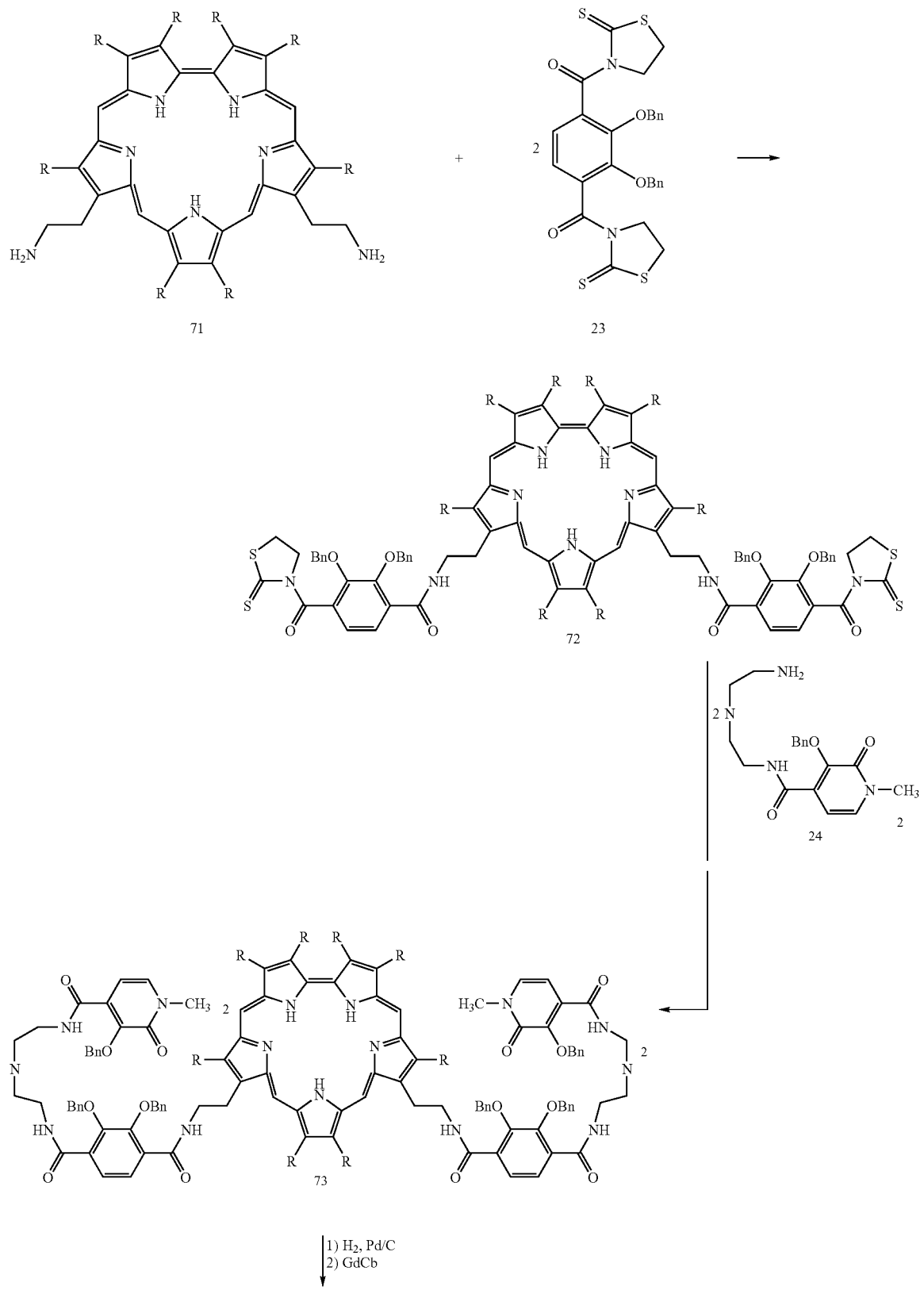

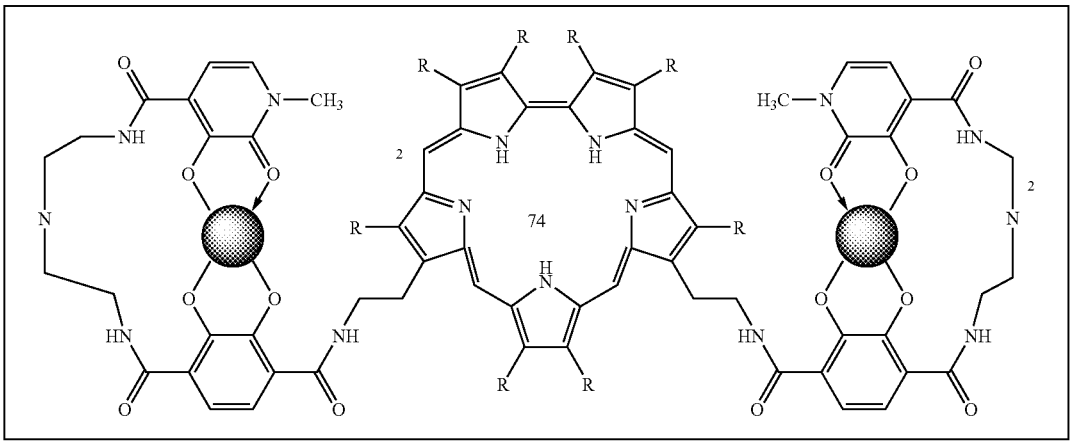

A C$_2$ symmetric sapphyrin is disubstituted with amine pendants. The addition of sapphyrin derivative 71 (R=Me) and two equivalents of 23 form a disubstituted derivative 72 which is then be treated with 2 eq. of 24 in known amine coupling to form 73, which preserves the integrity of the [TREN-HOPO-TAM] geometry. Ligand 73 is further deprotected and GdCl$_3$ is combined with 73 to form 74.

The present invention also provides water soluble sapphyrin-Gd(III) complexes. In an exemplary embodiment, the sapphyrin is derivatized with a polyethylene glycol moiety, to counter the lipophilicy of the sapphyrin. The PEG pendant of 75 can be tethered at the hydroxypyridinoate nitrogen as shown in Scheme 16. Chlorinated 76 is then added directly to 12 at the HOPO ring nitrogen forming monosubstituted 77. Derivative 77 can be further combined with 24 and be incorporated in the second step of Scheme 15.

Scheme 16

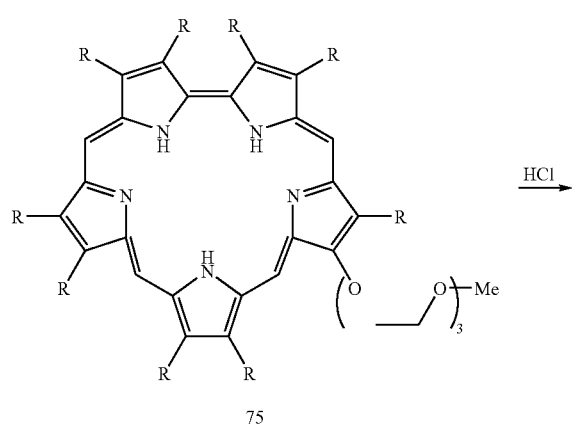

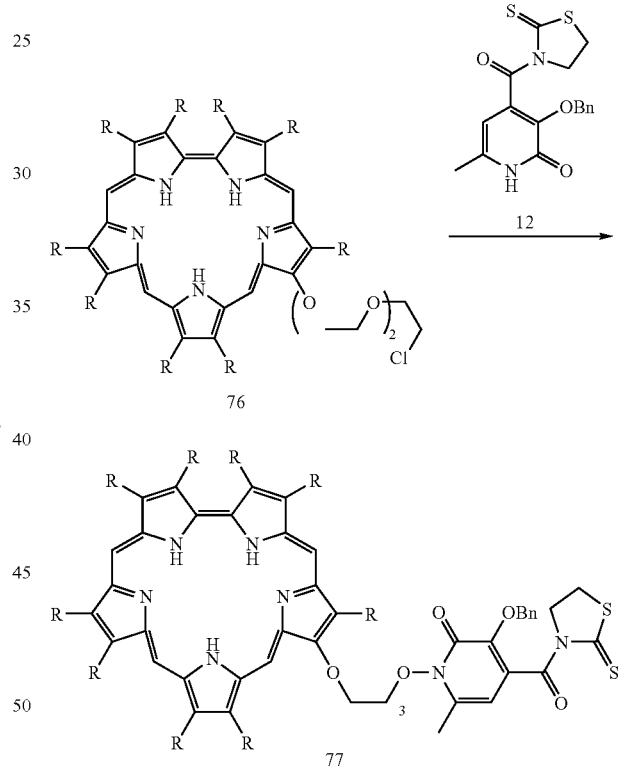

In another exemplary embodiment, the TREN is functionalized with PEG in a manner that is not detrimental to the stability of the complex. Thus, one or more of the three TREN arms is functionalized by Tf-protection of the amine nitrogen with the concomitant labilizing of the vicinal proton for substitution by sapphyrin with alcohol pendant arms (Scheme 17). An exemplary complex has a Gd to sapphyrin ratio of 4:1. In Scheme 17, TREN (commercially available) is protected, mono-iodinated and combined with 80. The resulting product is reduced to form 81. This tetra-TREN can be flexibly used to prepare compounds of the invention.

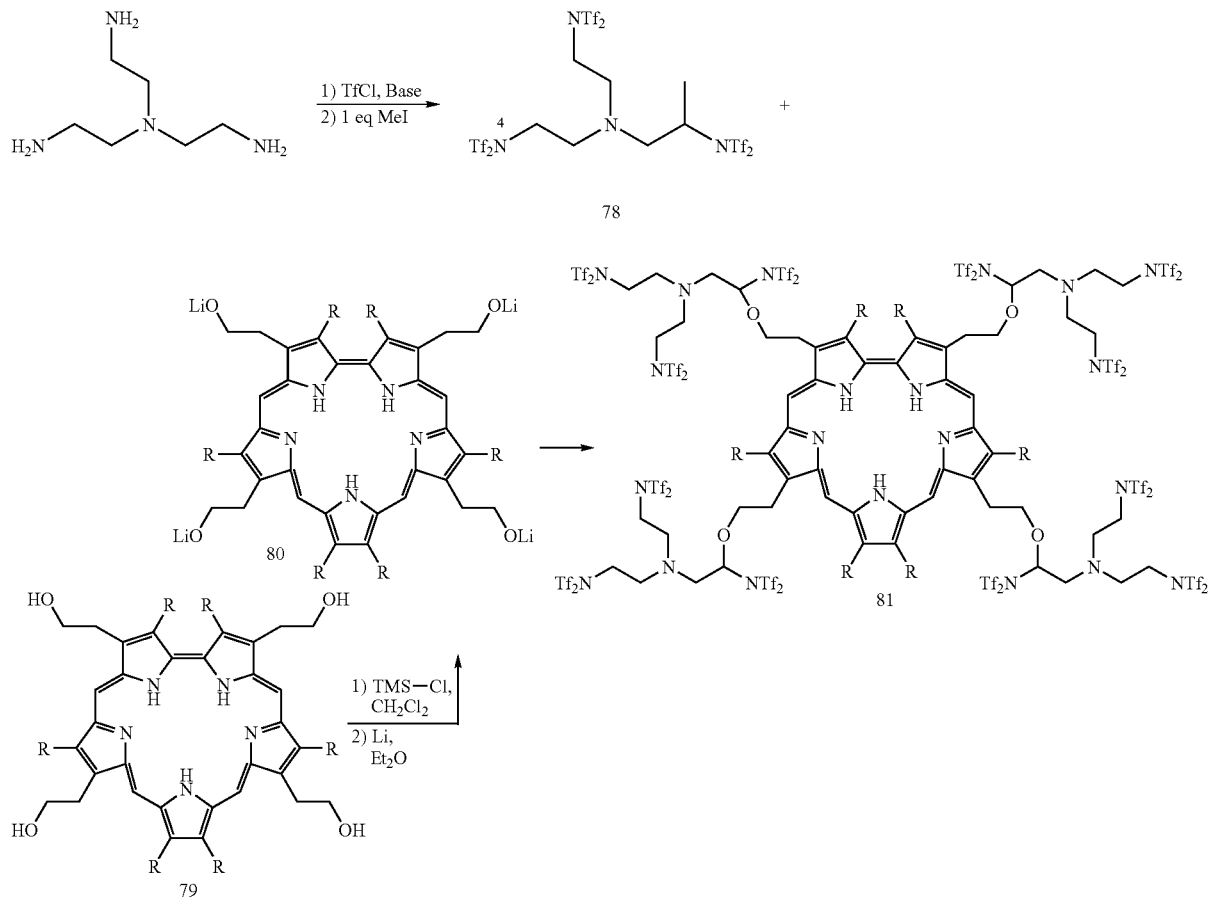

In a further exemplary embodiment, the compounds of the invention are further conjugated to quinacrine or secretin to further enhance pancreas affinity due to their individual molecular recognition, and pancreatic tumor selectivity. Firstly, quinacrine, 82, has an affinity for acidic phospholipids and the enzyme pancreatic phospholipase A2. The acridine group also serves as a fluorescent marker, providing a means of detecting the compound in tissues. Compound 82 which is commercially available can be Suzuki coupled with a borane functionalized propeneamine (commercially available) and then undergo amide coupling with 23 to yield the tethered quinacrine-TAM fragment (Scheme 18). 84 is utilized in place of 23 (Scheme 15, Step 1) in conjunction with tetra-TREN 81 in place of reagent 24 (0.25 eq.) to prepare a Gd multiconjugate.

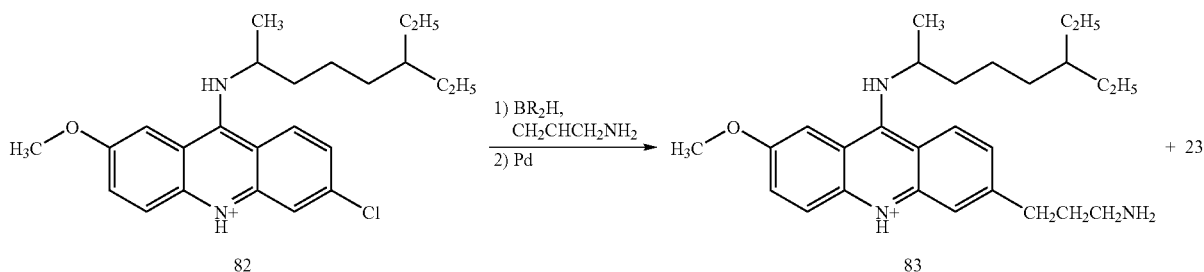

-continued

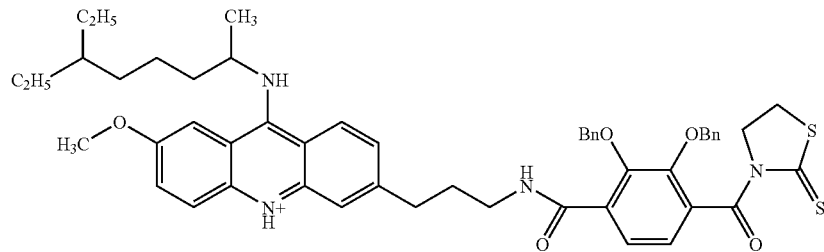

84

Secretin (commercially available) can also be conjugated at its N terminus. Secretin, a 27-amino acid polypeptide, is received in vivo on its carboxylate end at pancreatic parenchymal cells. The N-terminus may be selectively iodinated in reasonable yield prior to substitution at the 6-Me-HOPO nitrogen.

Compound Characterization

The present invention generally utilizes art-recognized methods to characterize the new ligands and their metal complexes. The following sections provide exemplary methods of characterizing the compounds of the invention. The methods set forth below are intended to illustrate useful techniques for characterizing the compositions of the invention, but should not be construed as limiting the methods of us in characterizing the compositions of the invention.

Methods of determining stability constants include, but are not limited to those set forth in, Johnson, A. R. et al., *Inorg. Chem.* 2000, 39, 2652-2660; and Cohen, S. M. X. et al., *Inorg. Chem.* 2000, 39, 5747.

The Bjerrum method can be used for metal complex stability measurements (pH titrations of ligand and metal+ligand). Competition titrations with DTPA can be performed to determine the stability of very stable complexes where direct pH titration methods are inappropriate. Spectrophotometric techniques can be used to monitor metal-ligand complexation reactions, which give rise to changes in the Vis/UV spectra relative to the parent metal and ligand species. With digitally-recording automated spectrophotometeric titrators, factor analysis of the Vis/UV spectra readily determined the species in solution, their individual spectra and the equilibrium constants which interrelate them.

Experimental Determination of Water Solubility

To attain neutral pH, a 0.01 M solution of buffer (HEPES, pKa 7.55) in 0.1 M KCl was made in its acidic form and neutralized to pH 7 with KOH. A dilute solution (of the metal complex) of known concentration was prepared and the UV-Vis spectrum acquired. The extinction coefficient ($\epsilon$) at the maximum absorbance (at wavelength typically 320-360 nm) was then calculated using Beer-Lambert's law. A saturated solution of the metal complex was then prepared and the UV-Vis spectrum acquired and the maximum absorbance (at wavelength typically 320-360 nm) recorded. In cases where the saturated solution produced extremely high absorbances, the saturated solution was diluted and then the spectrum recorded. Using the known $\epsilon$, the concentration of the saturated solution was then determined. This corresponds to the minimum solubility of the complex in $H_2O$ (pH 7, 25° C., 0.1 M). The solubility of the complexes were observed to increase at lower salt concentration. The spectra of the complexes at pH 7 are consistent with the known ML spectra observed from spectrophotometric solution thermodynamics studies of the metal-ligand complexation reactions and indicate the absence of free ligand (note: M=metal, L=ligand).

Typically, preliminary investigation of the minimum solubility of the complexes involves dissolving a known quantity of the complex in a precise volume of solvent. The visible disappearance of particulate matter, over time or instantaneous in some cases, is indicative of complete dissolution of the complex. Hence, a determination of the minimum solubility of the complexes is made before spectral studies are performed.

Ligand Protonation Constants

The protonation constants for chelates of the invention are readily determined by potentiometric titrations. These constants are defined by eq 2:

$$H_{n-1}L + H^+ \longleftrightarrow H_nL \quad K_n = \frac{[H_nL]}{[H_{n-1}L][H^+]}. \quad (2)$$

Gd(III), Zn(II) and Ca(II) Formation Constants

Data for the spectrophotometric determination of formation constants for the compounds of the invention (e.g., Tren-Me$_2$-5,4-HOPY) with gadolinium are generally collected over a pH range of 2-8.

The formation constants are defined by eq 3:

$$mM + lL + hH \longleftrightarrow M_mL_lH_h \quad \beta_{mlh} = \frac{[M_mL_lH_h]}{[M]^m[L]^l[H]^h} \quad (3)$$

The spectrophotometric data is refined using a model. For example, for Gd[TrenHOPY], the model includes four components: $LH_4^+$, GdL, GdLH$^+$ and GdLH$_2^{2+}$. This speciation is similar to the solution behavior of Tren-MOE-3,2-HOPO, although the parent complex, Gd(Tren-Me-3,2-HOPO), was not formerly reported as possessing a diprotonated species. (Johnson et al., *Inorg. Chem.*, 39:2652 (2000))

LogK$_{ML}$ values reflect the metal-ligand affinity for deprotonated ligand in the reaction, M+L$\rightleftharpoons$ML. The pM value is one way to make allowance for the competition for the ligand by protons in real solutions, and thus gives a more complete picture of the effectiveness of the ligand in chelating the metal.

The pGd values are defined by eq 4:

$$pGd = -\log[Gd]_{free} \text{ at pH 7.4 for } [Gd]=1 \text{ μM, } [L]=10 \text{ μM} \quad (4)$$

A pM value can be calculated for many conditions, but it is generally preferable to calculate it for conditions relevant to biological considerations.

Potentiometric titrations of the ligand and/or complex with zinc and calcium ions can also be performed. The potentiometric titrations provide a comparison to the high selectivity for Gd(III) afforded by the TrenHOPO system. (Xu et al., *J. Am. Chem. Soc.*, 117:7245 (1995))

In an exemplary assay, solutions of a 1:1 ratio of metal ion to ligand are titrated over a pH range of 2.4-11. Generally, low concentrations (0.25 mM) are used to avoid precipitation in the pH region of 5.5-6.5 for both the $Ca^{2+}$ and $Zn^{2+}$ systems.

Water Proton Relaxation

The efficacy of a paramagnetic complex as a possible MRI contrast agent depends on its ability to catalyze the nuclear magnetic relaxation rate of solvent protons (Lauffer, R. B., *Chem. Rev.*, 87, 901 (1987); Tweedle, M. F.; Kumar, K. *In Magnetic Resonance Imaging (MRI) Contrast Agents*; Clarke, M. I., Sadler, P. J., Eds.; Springer: Berlin, Germany, Vol. 2, p. 1 (1999); Koenig et al., *Prog. NMR Spectrosc.*, 22:487 (1990)). This property, which is measured in terms in relaxivity, $r_{1p}$, is defined as the enhancement of the water proton longitudinal relaxation rate induced by a 1 $mML^{-1}$ solution of the paramagnetic compound at a given temperature and magnetic field strength (Aime et al., *Chem. Soc. Rev.*, 27:19 (1998)). In the absence of specific interactions, the values of $r_{1p}$ in vitro and in blood serum are quite comparable and so analysis of the relaxation properties of a paramagnetic solute in water are of importance for predicting the behavior in vivo.

$^1$H and $^{17}$O NMR Relaxivity Studies

The proton relaxivity of the new Gd(III) complexes are generally assessed by art-recognized methods. See, for example, Aime, S. B. et al., *Acc. Chem. Res.* 1999, 32, 941; Aime, S. B. et al., *Coord. Chem. Rev.* 1999, 185-6, 321; Aime, S. B. et al., *Chem. Soc. Rev.* 1998, 27, 19; Aime, S. B. et al., *Magn. Reson. Chem.* 1998, 36, S200; Aime, S. B. et al., *J. Biol. Inorg. Chem.* 1997, 2, 470; Botta, M., *Eur. J. Inorg Chem.* 2000, 399).

In an exemplary assay, the longitudinal water proton relaxation rate at 20 MHz are measured (typically with a NMR spectrometer operating at 0.5 T) with a reproducibility of the $T_1$ data to ±0.5%. Equipment for the control of temperature (with an accuracy of ±0.1°C.) during these measurements are employed.

The mean residence water lifetime, $\tau_m$, is generally determined by measuring the transverse $^{17}$O NMR relaxation rate ($R_{2p}$) at various temperatures. The variable-temperature $^{17}$O NMR measurement is performed using spectrometers which operate at various magnetic field strengths (2.1 and 9.4 T are typically used) equipped with a 5 mm probe. A $D_2O$ external lock and solutions containing 2.6% of the $^{17}$O isotope are used. The observed transverse relaxation rates are calculated from the signal width at half-height. Details of the instrumentation, experimental methods, and data analysis are reported elsewhere and are incorporated by reference herein (Cohen, S. M. X. et al., *Inorg. Chem.* 2000, 39, 5747; Aime, S. B. et al., *J. Biol. Inorg. Chem.* 1997, 2, 470; Aime, S. B. et al., *Magn. Reson. Chem.* 1998, 36, S200).

The Gd(III) complexes of the HOPO and HOPY systems set forth herein are promising candidates for MRI contrast agents since they possess high thermodynamic stability and high relaxivity due to the presence of two coordinated water molecules characterized by a fast rate of. The relaxivity of the complexes of the invention, measured at 20 MHz, 25°C. and pH=7.2 is typically greater than 5.0 $Mm^{-1}s^{-1}$, with relaxivities of from at least about 9.0 $mM^{-1}s^{-1}$ to about 11 $mM^{-1}s^{-1}$ being readily obtained. The higher values are at least about two times higher than that of the currently used contrast agents based on polyaminocarboxylate.

NMRD Studies

Measuring the relaxation rates of an abundant nucleus in a large magnetic field range is called relaxometry. A relaxometry profile is a plot of nuclear magnetic relaxation rates, usually $1/T_1$, as a function of the Larmor frequency or the magnetic field on a logarithmic scale (see FIG. 7). This plot is also called a Nuclear Magnetic Relaxation Dispersion (NMRD) curve. Whereas the measurement of relaxation rates is a routine task at higher magnetic fields (>1 MHz proton Larmor frequency, 0.023 T), at lower fields the dramatic decrease in sensitivity sets a practical limit. NMRD profiles of paramagnetic solutions show, however, very often interesting features at frequencies below 1 MHz. This special experimental technique utilizes a fast cycling of the magnetic field with a field-cycling relaxometer (Caravan, P. E. et al., *Chem. Rev.* 1999, 99, 2293; Toth, E. et al *Top. Curr. Chem.* 2002, 221).

Nuclear magnetic resonance dispersion (NMRD) profiles can be used to determine the values of the parameters that contribute to the relaxivity of a Gd(III) complex (e.g. q and $\tau_r$) The methods involved measuring the magnetic field strength (Larmor frequency) dependence of the solvent proton longitudinal relaxation rate in the presence of a Gd(III) complex. The proton $1/T_1$ NMRD profiles were typically measured on a field-cycling relaxometer over a continuum of magnetic field strengths. The relaxometer generally operates under computer control with an absolute uncertainty in $1/T_1$ of ±1%. Details of the instrumentation and data acquisition procedure are reported elsewhere and are incorporated by reference herein. (Aime, S. B. et al., *J. Biol. Inorg. Chem.* 1997, 2, 470; Aime, S. B. et al., *Magn. Reson. Chem.* 1998, 36, S200; Cohen, S. M. X. et al., *Inorg. Chem.* 2000, 39, 5747).

Inner-Hydration Sphere Assessment

In an exemplary assay, the number of water molecules (q) bound to the metal ion is assessed by luminescence decay kinetics. In this method, the metal ions are directly excited with a powerful Nd-YAG laser and the decay rates are recorded. In general, the method relies upon the preparation of the terbium(III) complexes of the new ligands. Alternatively, the europopium (III) complexes of the new ligands are synthesized.

Accurate assessment of q is obtained by comparing the decay rates of the complex in $H_2O$ and $D_2O$ (which minimally quenches emission) are compared as the inner sphere water molecules quench the emission of the metal ion.

Variable Temperature $^{17}$O NMR

The NMRD profiles of complexes of the invention are in the fast exchange regime, a condition that precludes the assessment of the water exchange rate from the analysis of the magnetic field dependence of the proton relaxivities. The value of $\tau_M$, a crucial parameter for the evaluation of the efficiency of a contrast agent, can be independently obtained by a variable temperature, proton decoupled $^{17}$O NMR measurement of the water nuclear transverse relaxation rate ($R_2$) using a well-established (Powell et al., *J. Am. Chem. Soc.*, 118:9333 (1996); Aime et al., *Acc. Chem. Res.*, 32:941

(1999)) The $R_2$ values are dominated by the scalar relaxation mechanism which depends on $k_{ex}$ and its temperature dependence ($\Delta H_M$), the electronic relaxation rate and its temperature dependence ($\Delta^2$, $\tau_V$, $\Delta Hv$) and the hyperfine coupling constant A/h.

A standard value of $-3.8\times10^6$ rad s$^{-1}$ is used for the hyperfine coupling constant and the values obtained by the analysis of the NMRD profiles for electron relaxation ($\Delta^2$ and $\tau_V$). The data id fitted to the Swift-Connick equations.

Biomolecule Affinity Measurements

Biomolecule affinity measurements are generally measured by art-recognized methods. For example, the non-covalent interaction between HSA and the metal complexes containing hydrophobic groups have been thoroughly investigated using the well-established proton relaxation enhancement (PRE) method (Caravan, P. E. et al., *Chem. Rev.* 1999, 99, 2293) that allows both the binding parameters ($K_a$) and the relaxivity enhancement of the (Metal complex)-HSA adduct to be determined. In this method, the water proton relaxation rates of solutions containing the metal complex and increasing concentrations of the serum protein are measured.

An exemplary assay is performed with competitor probes (such as warfarin and ibuprofen), which elucidate the binding sites of the protein with which the MRI agents interact. The measurements are typically performed at pH 7.4 (in phosphate buffer) and 298 K, which are close to physiological conditions.

In HSA, there are often multiple non-identical binding sites that may give rise to varying degrees of proton relaxation enhancement. Hence, an independent method for determining the binding constants may be necessary to complement the PRE method.

The emissive properties of Eu(III) and/or Tb(III), are used to reflect the rates of emissive decay in distinct sites that the metal ion occupies. Hence, luminescence titration of the Eu(III) and Tb(III) complexes of the ligands with HSA is a good method for determining biomolecule affinity (Feig, A. L. P. et al., *Chem. & Biol.* 1999, 6, 801; Chaudhuri, D. H. et al., *Biochem.* 1997, 36, 9674; Cronce, D. T. H. et al., *Biochem.* 1992, 31, 7963.

Biodistribution and Acute Toxicity Studies

The conjugation of metal chelates to substituents that target specific regions of the body necessitated biodistribution studies on the new MRI agents. Typically, a preliminary in vitro cell screen is performed in order to identify the possible high affinity of these agents for specific mammalian cells (e.g. myocytes and hepatocytes). The in vitro cell cytotoxicity of the agents is assessed using, for example, the trypan blue exclusion method. Toxicity studies on healthy mice and rats are performed to obtain the $LD_{50}$ data for the complexes.

In another exemplary assay, the in vivo biodistribution of the chelating agents in tumor-induced rats is determined to assess tumor uptake of the agents. An exemplary assay involves radiotracer studies using $^{153}$Gd. The rodent is induced with the tumor of choice and the tumor is allowed to grow over several weeks to a diameter suitable for biodistribution experiments. The rodents are then transferred to a normal diet for an appropriate period of time. The radioactive MRI agent is then injected and the urine and feces collected and analyzed for counts periodically. The animal is subsequently sacrificed and the organs removed for radioactive analyses. The biodistribution of the MRI agent as a percentage of the injected dose (% ID) per organ and as a %ID/g of tissue weight is then calculated. This is then compared with the distribution of the MRI agent in a control group (healthy rodents of the same cell line). A study on the in vivo biodistribution of the chelating agents enables the identification of the localized distribution of the MRI agents in the presence and absence of tumors.

Pharmaceutical Formulations

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10 g, more typically 1.0 mg to 1 g, most typically 10 mg to 500 mg, according to the particular application and the potency of the active component. The composition can, if desired, also contain other compatible therapeutic or diagnostic agents.

Effective Dosages

MRI contrast agents are typically administered at a dosage of 0.1-0.3 mmol/kg patient in 0.5 M solutions (Caravan, P. E. et al., *Chem. Rev.* 1999, 99, 2293). The improved properties of the present agents allows their administration in amounts lower than art-recognized aminocarboxylate-based contrast agents. Adjusting the dose to achieve maximal efficacy in humans based on the methods described above and other methods as are well-known in the art is well within the capabilities of the ordinarily skilled artisan.

The Methods

In an exemplary embodiment, the invention provides a method for performing a contrast enhanced imaging study on a subject. The method includes administering a metal complex of the invention to the subject and acquiring an image of the subject. The complexes of the invention are of use in a range of diagnostic imaging modalities including, but not limited to, MRI, X-ray and CT.

The invention also provides a method for tuning a physical property of a metal complex of the invention. Exemplary physical properties that are tuned by the method of the invention include, but are not limited to, water exchange rate, rotational correlation time, in vivo residence time, relaxivity and water solubility. In one embodiment the method includes preparing a parent complex that may or may not have a poly(ether) as a component of the ligand and measuring the physical property of the complex. If the measured property is less than ideal, the property is adjusted by preparing an analogue of the ligand that includes a poly(ether), or that has a poly(ether) of a size and/or structure different from that of the first ligand. The inventors have recognized that, using the iterative method provided herein, it is possible to tune and refine a range of physical properties of the chelates of the invention.

Also provided by the present invention is a method for treating a patient for metal ion overload. The method includes administering to a patient in need of such treatment an amount of a compound prepared by the method of the invention. The amount of compound administered is effective to reduce the metal ion load in the patient. It is well within the abilities of one of skill in the art to ascertain an appropriate dosage and treatment regimen for a particular patient.

In a preferred embodiment, treating the patient with a compound prepared by a method of the invention results in a greater amount of metal ion being removed from the patient than is removed upon treating the patient with an identical dose of the same compound prepared by a previously known method.

The materials, methods and devices of the present invention are further illustrated by the examples that follow. These examples are offered to illustrate, but not to limit the claimed invention.

EXAMPLES

Example 1

Preparation of 6-methyl-3-hydroxy-2(1H)-pyridinone-4-carboxylic acid ethyl ester (Formula 8 in Scheme 2)

6-methyl-3-hydroxy-2(1H)-pyridinone 4-carboxylic acid ethyl ester-is a known material; however the previous preparation results in an impure product of low yield. Therefore, an improved procedure has been developed, which is higher yielding and can be scaled up to give large quantities of the product in high purity. The details are described as follows:

Sodium diethyloxylacetate (42.1 g, 200 mmol) was dissolved in THF (500 ml) and then placed into a 1-liter 3-neck round bottom flask. Chloroacetone (16 ml, 200 mmol) was added to the mixture. After waiting 10 minutes, $NH_3$ gas was bubbled through the reaction and $AlCl_3$ (2.67 g, 20 mmols) was slowly and carefully added. The reaction was stirred under ambient conditions for 5 days. The resulting orange solid was filtered, and taken up in 1 M HCl (500 ml) so that the pH<3. The resulting suspension was stirred for 30 min and the precipitate filtered, washed with distilled water and recrystallized from hot EtOH (approx 1 L) to yield colorless crystals (Yield: 15.7 g, 40%). mp 227-229° C. $^1$H NMR ($d_6$-DMSO, 300 MHz): δ=1.24 (t, 3H, $CH_3$), 2.07 (s, 3H, $CH_3$), 4.22 (q, 2H, $CH_2$), 6.07 (s, 1H, CH) ppm. Anal. Calcd (Found) for $C_9H_{11}O_4N$: C, 54.82 (55.06); H, 5.62 (5.53); N, 7.11 (7.07). EI-MS (+): m/z: 198[M+H]$^+$.

Example 2

Preparation of 3-benzyloxy-4-carboxy-6-methyl-2 (1H)-pyridinone (Formula 11 in Scheme 2)

6-methyl-3-hydroxy-2(1H)-pyridinone-4-carboxylic acid ethyl ester (11.8 g, 60 mmol) and $K_2CO_3$ (9.06 g, 65 mmol) were dissolved in $H_2O$ (650 ml) with aid of ultra-sonication. This solution was added to a solution of benzyl bromide (7.8 mL, 65 mmol) in $CH_2Cl_2$ (500 ml) in a 2-liter 3-neck round bottom flask. Cetylpyridinium chloride (9.09 g, 30 mmol) was added as the phase transfer catalyst for this reaction. The solution was stirred with an overhead stirrer, at 40° C. for 1 day until the reaction was judged to be complete by TLC. The two layers were separated, and the aqueous layer was extracted twice with $CH_2Cl_2$ (100 ml). The organic layers were combined and the solvents were removed. Purification, of this crude product (3-benzyloxy-6-methyl-2(1H)-pyridinone-4-carboxylic acid ethyl ester (9) was possible by column chromatography, although it was found to be more convenient to use the crude product directly in the subsequent ester hydrolysis reaction, and purify after this step. $^1$H NMR ($CDCl_3$, 300 MHz): δ=1.29 (t, 3H, $CH_3$), 2.35 (s, 3H, $CH_3$), 4.30 (q, 2H, $CH_2$), 5.26 (d, 2H, $CH_2$), 6.22 (s, 1H, CH), 7.35 (m, 5H, Ph) ppm. The product was dissolved in a solution of KOH (16.68 g, 297 mmol) in MeOH (300 ml) and the solution heated under reflux for 24 h or until the reaction was judged to be complete by TLC. The solution was filtered and acidified to pH=1 with 6M HCl. The white solid was filtered, washed with 100 mL of $H_2O$ and recrystallized from EtOH (400 ml) to give a white crystalline solid (Yield: 7.06 g, 46% from 4-carboxyethylester-6-methyl-3-hydroxy-2(1H)-pyridinone). $^1$H NMR ($d_6$-DMSO, 300 MHz): δ=2.11 (s, 3H, $CH_3$), 5.07 (d, 2H, $CH_2$), 5.97 (s, 1H, CH), 7.30 (m, 5H, Ph) ppm. Anal. Calcd (Found) for $C_{14}H_{13}O_4N$: C, 64.88 (64.73); H, 5.02 (5.15); N, 5.41 (5.37). El-MS (+): m/z: 259[M]$^+$.

Example 3

Preparation of 3-benzyloxy-6-methyl-4-(2-thioxo-thiazolidine-3-carbonyl)-2(1H)-pyridinone (Formula 12 in Scheme 2)

3-benzyloxy-4-carboxy-6-methyl-2(1H)-pyridinone (5.39 g, 21.1 mmol) was dissolved in dry THF (200 ml). Then 2-mercaptothiazoline (2.71 g, 23.2 mmol) and DMAP (0.25 g, 2.0 mmol) were added and the solution stirred under an atmosphere of $N_2$ for 1 h. Then dicyclohexylcarbodiimide (DCC, 5.12 g, 25.3 mmol) was added in small portions at intervals split over 3 hrs. The reaction was left to stir for 16 h, and then left to stand at 0° C. for a further 24 h. The dicyclohexylurea (DCU) was removed by filtration, and the solvents removed. The remaining residue was dissolved in $CH_2Cl_2$, filtered and purified by a gradient flash silica column (2-6% $CH_3OH$ in $CH_2Cl_2$). The solvents were removed from the appropriate fractions by rotary evaporation, and the residue recrystallized from acetone, yielding yellow crystals (3.78 g, 56%). $^1$H NMR (CDCl$_3$, 300 MHz): δ=7.32-7.47 (m, 5H, aromatic Bn), 5.98 (s, 1H, CH), 5.34 (s, 2H, Bn $CH_2$), 4.34 (t, J=7.3 Hz, 2H, $CH_2$), 2.92 (t, J=7.3 Hz, 2H, $CH_2$), 2.34 (s, 3H, $CH_3$) ppm. Anal. Calcd (Found) for $C_{17}H_{16}N_2O_3S_2$: C, 56.65 (56.50); H, 4.47 (4.51); N, 7.77 (7.70). FAB-MS (+): m/z: 361[M+H]$^+$.

Example 4

Preparation of 1-benzyl-3-benzyloxy-4-carboxy-6-methyl-2(1H)-pyridinone (Formula 49 in Scheme 10)

$K_2CO_3$ (10.5 g, 75.4 mmol) was added to a suspension of 6-methyl-3-hydroxy-2(1H)-pyridinone-4-carboxylic acid ethyl ester (5.20 g, 26.4 mmol) in dry DMF (10 ml) under an atmosphere of $N_2$. Benzyl chloride (6.96 g, 55.0 mmol) was added and the reaction stirred at 65° C. for 30 h, the progress of the reaction was monitored by TLC. The solvents were removed by rotary evaporation and the residue taken up in EtOAc (100 ml) and water (100 ml) The organic layer was washed with water (5×100 ml), dried ($Na_2SO_4$), filtered and evaporated to dryness. The crude product, 1-benzyl-3-benzyloxy-6-methyl-2(1H)-pyridinone-4-carboxylic acid ethyl ester (Formula 10), was partially purified by column chromatography (eluent: $CH_2Cl_2$), and it was obtained as a light brown oil. (Crude yield: 7.46 g, 75%). $^1$H NMR (CDCl$_3$, 300 MHz): δ=7.10-7.51 (m, 10H, Bn), 6.18 (s, 1H, HOPO), 5.36 (s, 2H, Bn-$CH_2$), 5.31 (s, 2H, Bn-$CH_2$), 4.30 (q, J=7.1 Hz, 2H, $CH_2$), 2.26 (s, 3H, HOPO $CH_3$), 1.28 (t, J=6.9 Hz, 3H, $CH_3$ Et ester) ppm. FAB-MS (+): m/z: 378.2[M+H]$^+$. The resulting oil was dissolved in a solution of KOH (2.3 g, 40 mmol) in MeOH (200 ml).

The reaction was left stirring for 2 days, by which time TLC indicated that the reaction had gone to completion. The solvent was removed, and the residue dissolved in distilled water. The pH of the solution was lowered to 1 by addition of 6.0M HCl, to yield a white precipitate which was filtered and dried (Yield: 6.27 g, 68% based on 6-methyl-3-hydroxy-2 (1H)-pyridinone-4-carboxylic acid ethyl ester). $^1$H NMR (CDCl$_3$, 400 MHz): δ=7.30-7.44 (m, 10H, Bn), 6.58 (s, 1H, HOPO), 5.63 (s, 2H, Bn-$CH_2$), 5.37 (s, 2H, Bn-$CH_2$), 2.30 (s, 3H, HOPO $CH_3$) ppm. Anal. Calcd (Found) for $C_{21}H_{19}NO_4 \cdot 0.4H_2O$: C, 70.73 (72.19); H, 5.60 (5.66); N, 3.93 (3.94). FAB-MS (+): m/z: 350[M+1]$^+$. Crystals suitable for X-ray diffraction were obtained by slow evaporation of a solution of AcOEt.

Example 5

Preparation of 1-benzyl-3-benzyloxy-6-methyl-4-(2-thioxo-thiazolidine-3-carbonyl)-2(1H)-pyridinone (Formula 50 in Scheme 10)

1-benzyl-3-benzyloxy-4-carboxy-6-methyl-2(1H)-pyridinone (5.36 g, 15.3 mmol) was dissolved in $CH_2Cl_2$ (100 ml) under an atmosphere of nitrogen. Then 2-mercaptothiazoline (1.88 g, 16.1 mmol) and dimethylaminopyridine (DMAP, 0.16 g, 1.0 mmol) were added and the solution stirred for 1 h. Dicyclohexylcarbodiimide (DCC, 3.45 g, 16.9 mmol) was then added in small portions and the reaction mixture stirred for 16 h, and then allowed to stand for 24 h at 0° C. The reaction mixture was filtered and the solvent removed by evaporation. EtOAc (10 ml) was added, and the solution filtered. This last step was repeated 3 times in order to remove the dicyclohexylurea (DCU), yielding a yellow oil. The product was purified by flash column chromatography (silica, $CH_2Cl_2$ as eluent). The solvents were removed by rotary evaporation, yielding a viscous yellow oil, which was recrystallized from acetone to give a yellow crystalline solid (Yield: 5.10 g, 74%). $^1$H NMR (CDCl$_3$, 400 MHz): δ=7.12-7.49 (m, 10H, Bn), 5.98 (s, 1H, HOPO), 5.38 (s, 2H, Bn-$CH_2$), 5.34 (s, 2H, Bn-$CH_2$), 4.59 (t, J=7.3 Hz, 2H, thiaz), 2.90 (t, 2H, J=7.3 Hz, thiaz), 2.27 (s, 3H, HOPO $CH_3$) ppm. Anal. Calcd (Found) for $C_{24}H_{22}N_2O_3S_2$: C, 63.98 (64.04); H, 4.92 (5.02); N, 6.22 (6.03). FAB-MS (+): m/z: 451 [M+H]$^+$.

Example 6

Preparation of 4-(2-ethanolcarbamoyl)-3-hydroxy-6-methyl-2(1H)-pyridinone (Formula 10C)

(1) Preparation of 3-benzyloxy-4-(2-ethanolcarbamoyl)-6-methyl-2(1H)-pyridinone (10B)

Ethanolamine (0.044 ml, 0.672 mmol) was added to a solution of 3-benzyloxy-6-methyl-4-(2-thioxo-thiazolidine-3-carbonyl)-2(1H)-pyridinone (0.200 g, 0.577 mmol) in $CH_2Cl_2$ (15 ml). The resulting solution was stirred in the dark for 10 h under ambient conditions during which time the solution turned from yellow to colorless. This solution was purified by a gradient flash silica column (2-8% CH3OH in CH2Cl2), and the solvent removed to yield a white solid, (Yield: 0.161 g, 97%). $^1$H NMR (CDCl$_3$, 300 MHz): δ=8.21 (t, 1H, NH), 7.38-7.46 (m, 5H, Bn), 6.64 (s, 1H, HOPO-H), 5.38 (s, 6H, $CH_2$), 3.61 (t, J=4.8 Hz, 2H, $CH_2$), 3.38 (q, J=4.8 Hz, 2H, $CH_2$), 2.33 (s, 3H, $CH_3$) ppm. Anal. Calcd (Found) for $C_{16}H_{18}N_2O_4$: C, 63.56 (63.21); H, 6.00 (6.12); N, 9.27 (8.99) ES-MS (+): m/z: 302[M]$^+$.

(2) Preparation of 4-(2-ethanolcarbamoyl)-3-hydroxy-6-methyl-2(1H)-pyridinone (10C)

5% Pd on C (0.100 g) was added to a solution of 3-benzyloxy-4(2-ethanolcarbamoyl)-6-methyl-2(1H)-pyridinone (0.100 g, 0.348 mmol) in AcOH (5 ml) and MeOH (5 ml) and the mixture stirred under an atmosphere of $H_2$ under ambient conditions for 12 h. The reaction was then filtered and the solvent removed. The residue was then re-precipitated from AcOH/MeCN to yield a light tan colored solid. (Yield: 0.042 g, 61%). $^1$H NMR ($D_2O$, 500 MHz): δ=6.44 (s, 1H, HOPO- H), 3.79 (t, J=5.3 Hz, 2H, CH$_2$), 3.56 (t, J=5.3 Hz, 2H, CH$_2$), 2.27 (s, 3H, CH$_3$) ppm. Anal. Calcd (Found) for C$_9$H$_{12}$N$_2$O$_4$: C, 50.94 (50.60); H, 5.70 (5.72); N, 13.20 (13.29) ppm. El-MS (+): m/z: 212[M]$^+$.

Example 7

Preparation of N,N,N,-tris[3-hydroxy-6-methyl-2 (1H)-pyridinone-4-carboxylamideethyl]amine (TREN-6-Me-3,2-HOPO, Formula 14 in Scheme 2)

(1) Preparation of N,N,N,-tris[3-benzyloxy-6-methyl-2(1H)-pyridinone-4-carboxylamideethyl]amine (Formula 13 in Scheme 2)

3-benzyloxy-6-methyl-4-(2-thioxo-thiazolidine-3-carbonyl)-2(1H)-pyridinone (1.5 g, 4.3 mmol) was dissolved in CH$_2$Cl$_2$ (30 ml). To this were added successive portions of tris(2-aminoethylamine) with a 4 h delay between subsequent additions until the solution turned from yellow to colorless. The solution was purified by two separate elutions down a silica column (solvent: CH$_2$Cl$_2$ with increasing gradient of MeOH from 2% to 8%). Removal of the solvent afforded a white glassy solid. (Yield: 0.91 g, 76%). $^1$H NMR (d$_6$-DMSO, 400 MHz): δ=8.12 (t, J=7.2 Hz, 3H, NH), 7.20-7.37 (m, 15H, Bn), 5.95 (s, 3H, HOPO-H), 5.12 (s, 6H, Bn CH$_2$), 3.14 (m, 6H, TREN CH$_2$), 2.42 (m, 6H, TREN CH$_2$), 2.08 (s, 9H, CH$_3$) ppm. Anal. Calcd (Found) for C$_{48}$H$_{51}$N$_7$O$_9$: C, 66.27 (65.97); H, 5.91 (5.91); N, 11.27 (11.17). FAB-MS (+): m/z: 870[M+H]$^+$.

(2) Preparation of N,N,N,-tris[3-hydroxy-6-methyl-2 (1H)-pyridinone-4-carboxylamideethyl]amine (TREN-6-Me-3,2-HOPO, Formula 14 in Scheme 2)

5% Pd on carbon (0.235 g) was added to a solution of N,N,N,-tris[3-benzyloxy-6-methyl-2(1H)-pyridinone-4-carboxylamideethyl]amine (0.360 g, 0.414 mmol) in AcOH (10 ml) and H$_2$O (5 ml) and the mixture stirred under an atmosphere of H$_2$ under ambient conditions for 2 h. The reaction was then filtered and the solvent removed. The remaining residue converted to the Cl$^-$ salt by dissolving in MeOH (10 ml) and one drop of conc. HCl and the solvent removed (×3). Excess HCl was then removed by dissolving the residue in MeOH (10 ml) and removing the solvent under reduced pressure (×3). The remaining residue was taken up in MeOH (2 ml) and added to a rapidly stirring solution of Et$_2$O (200 ml) to afford a white precipitate, which was filtered and dried under vacuum. (Yield: 0.225 g, 78%). $^1$H NMR (D$_2$O, 500 MHz): δ=5.87 (s, 3H, HOPO-H), 3.79 (m, 6H, TREN CH$_2$), 3.61 (m, 6H, TREN CH$_2$), 1.96 (s, 9H, CH$_3$) ppm. Anal. Calcd (Found) for TREN-6-Me-3,2-HOPO-HCl.3H$_2$O, C$_{27}$H$_{34}$N$_7$O$_8$Cl.3H$_2$O: C, 46.39 (46.09); H, 5.91 (5.82); N, 14.02 (13.80) ppm. FAB-MS (+): m/z: 600[M]$^+$.

Example 8

Preparation of the Gadolinium(III) Ion Complex with N,N,N,-tris[3-hydroxy-6-methyl-2(1H)-pyridinone-4-carboxylamideethyl]amine (Gd-TREN-6-Me-3,2-HOPO) (Formula 15, Scheme 2)

GdCl$_3$.6H$_2$O (0.0532 g, 0.136 mmol) was added to a solution of TREN-6-Me-HOPO (0.100 g, 0.143 mmol) in H$_2$O (10 ml) with an excess of pyridine and the solution heated to reflux for 2 h. A microcrystalline white solid precipitated from solution, which was filtered and dried under vacuum. (Yield: 0.080 g, 70%). Anal; Calcd (Found) for Gd(TREN-6-Me-3,2-HOPO)(H$_2$O)$_2$.H$_2$O, C$_{27}$H$_{38}$N$_7$O$_{10}$Gd.H$_2$O: C, 39.05 (39.37); H, 4.87 (4.42); N, 13.80 (13.37); Gd, 15.49 (15.35) ppm.

Example 9

Preparation of 2,3-bis-benzyloxy-1,4-bis(2-thioxo-thiazolidine-3-carbonyl)-benzene (BnTAMdiThiaz) (Formula 23 in Scheme 3)

Oxalyl Chloride (14 ml, 160 mmol) and DMF (1 drop) was added to a suspension of 2,3-Bis-benzyloxy-terephthalic acid (20 g, 52 mmol) in dry toluene (250 ml). After 24 h of stirring under an atmosphere of N$_2$, a light brown solution was obtained. The solvent was removed by rotary evaporation, and the residue dissolved in dry THF (200 ml). The solution was cooled to −35° C., and a solution of 2-mercaptothiazoline (12.6 g, 104 mmol) and NEt$_3$ (10.1 g, 100 mmol) in THF (100 ml) was added dropwise over a period of 2 h. The solution was filtered at 0° C. to remove NEt$_3$.HCl. The solvents were removed, and the residue dissolved in CH$_2$Cl$_2$ (50 ml) and filtered through a silica plug to yield a bight yellow solution. The solvent was removed and the product was recrystallized from acetone (500 ml) to afford a bright yellow prisms. (Yield: 22.9 g, 76%). $^1$H NMR (CDCl$_3$, 400 MHz): δ=7.20-7.36 (m, 12H, aromatic H), 5.08 (s, 4H, Bn CH$_2$), 4.32 (t, J=7.3 Hz, 4H, CH$_2$), 2.96 (t, J=7.3 Hz, 4H, CH$_2$) ppm. Anal. Calcd (Found) for C$_{28}$H$_{24}$N$_2$O$_4$S$_4$: C, 57.91 (57.92); H, 4.17 (4.13); N, 4.82 (4.74). FAB-MS (+): m/z: 581 [M+H]$^+$.

Example 10

Preparation of TREN-1-Bn-6-Me-3,2-HOPO-TAM (19C)

(1) Preparation of benzyl protected TREN-1-Bn-6-Me-3,2-HOPO-TAM-thiazolide (19A)

A solution of 1-benzyl-3-benzyloxy-6-methyl-4-(2-thioxo-thiazolidine-3-carbonyl)-2(1H)-pyridinone (1.5 g, 3.3 mmol) in CH$_2$Cl$_2$ (100 ml) was added dropwise to a rapidly stirring solution of tris(2-aminoethylamine) (TREN, 0.219 g, 1.5 mmol) in CH$_2$Cl$_2$ (100 ml). The resulting solution was purified by a gradient flash silica column (2-10% CH$_3$OH and 1% Et$_3$N in CH$_2$Cl$_2$) This compound, TREN-(1-Bn-6-Me-3, 2-HOPO)$_2$ (Formula 7, R$_1$=benzyl, R$_2$=methyl, c=1, p=2) was dissolved in CH$_2$Cl$_2$ and added dropwise to a rapidly stirring solution of BnTAMdiThiaz (Formula 8, 14 g, 24 mmol) in CH$_2$Cl$_2$ (100 ml) over 2 h. The product was purified by a gradient flash silica column (2-5% CH$_3$OH in CH$_2$Cl$_2$), and obtained as a yellow foam. (Yield: 1.39 g, 73%). $^1$H NMR (CDCl$_3$, 400 MHz): δ=8.30 (br s, 1H, TAM NH), 7.94 (br s, 2H, HOPO NH), 7.85 (d, 1H, TAM CH), 7.27 (br s, 1H, TAM NH), 7.09-7.38 (m, 31H, aromatic H), 6.58 (s, 2H, HOPO-H), 5.35 (s, 8H, HOPO Bn CH$_2$), 5.12 (s, 2H, TAM Bn CH$_2$), 5.09 (s, 2H, TAM Bn CH$_2$), 4.37 (t, J=7.3 Hz, 2H, thiazolide CH$_2$), 3.38 (m, 6H, TREN CH$_2$), 2.93 (t, J=7.3 Hz, 2H, thiazolide CH$_2$), 2.37 (m, 6H, TREN CH$_2$), 2.25 (s, 6H, HOPO CH$_3$) ppm. Anal. Calcd (Found) for C$_{73}$H$_{71}$N$_7$O$_{10}$S$_2$.3.5H$_2$O: C, 65.77 (65.52); H, 5.86 (5.56); N, 7.36 (7.04). FAB-MS (+): m/z: 1270.5 [M+1]$^+$.

(2) Benzyl Protected TREN-1-Bn-6-Me-3,2-HOPO-TAM (19B)

Excess methylamine (solution in H$_2$O) was shaken with a solution of benzyl protected TREN-1-Bn-6-Me-3,2-HOPO- TAM-thiazolide (1.12 g, 0.883 mmol) in $CH_2Cl_2$ (100 ml), and the solution tuned from yellow to colorless within a few seconds. The product was purified by a gradient flash silica column (2-10% $CH_3OH$ in $CH_2Cl_2$) to yield a white foam after removal of solvents. (Yield: 0.76 g, 73%). $^1H$ NMR ($CDCl_3$, 400 MHz): δ=8.20-8.25 (m, 4H, NH), 7.05-7.37 (m, 32H, aromatic H), 6.18 (s, 2H, HOPO-H), 5.28 (s, 4H, HOPO Bn $CH_2$), 5.18 (s, 4H, HOPO Bn $CH_2$), 5.03 (s, 2H, TAM Bn $CH_2$), 5.00 (s, 2H, TAM Bn $CH_2$), 3.29 (m, 6H, TREN $CH_2$), 2.71 (d, 3H, TAM $CH_3$), 2.51 (m, 6H, TREN $CH_2$), 2.17 (s, 6H, HOPO $CH_3$) ppm. Anal. Calcd (Found) for $C_{71}H_{71}N_{70}O_{10}.2H_2O$: C, 69.99 (69.96); H, 6.20 (6.03); N, 8.05 (7.88). FAB-MS (+): m/z: 1182.6 $[M+1]^+$.

(3) TREN-1-Bn-6-Me-3,2-HOPO-TAM (19C)

10% Pd on carbon (0.235 g) was added to a solution of benzyl protected TREN-1-Bn-6-Me-HOPO-TAM (0.540 g, 0.457 mmol) in AcOH (10 ml) and $H_2O$ (5 ml) and the mixture stirred under an atmosphere of $H_2$ under ambient conditions for 48 h. The reaction was then filtered and the solvent removed. The remaining residue was converted to the $Cl^-$ salt by dissolving in MeOH (10 ml) and one drop of conc. HCl and the solvent removed (×3). Excess HCl was removed by dissolving the residue in MeOH (10 ml) and removing the solvent under reduced pressure (×3). The remaining residue was taken up in MeOH (2 ml) and added to a rapidly stirring solution of $Et_2O$ (200 ml) to afford a white precipitate which was filtered and dried under vacuum. (Yield: 0.324 g, 79%). $^1H$ NMR ($d_6$-DMSO, 300 MHz): δ=9.11 (br s, 1H, NH), 8.90 (br s, 1H, NH), 8.68 (br s, 2H, NH), 7.04-7.32 (m, 12H, aromatic H), 6.36 (s, 2H, HOPO-H), 5.27 (s, 4H, Bn $CH_2$), 3.72 (m, 6H, TREN $CH_2$), 3.46 (m, 6H, TREN $CH_2$), 2.79 (d, J=3.3 Hz, 3H, $CH_3$) ppm. Anal. Calcd (Found) for $C_{43}H_{47}N_7O_{10}.HCl.3H_2O$: C, 56.61 (56.60); H, 5.97 (5.89); N, 10.75 (10.46). FAB-MS (+): m/z: 822 $[M+H]^+$.

Example 11

Preparation of the Gadolinium(III) Ion Complex with TREN-1-Bn-6-Me-3,2-HOPO-TAM (Formula 19 in Scheme 2)

Excess pyridine was added to a solution of $GdCl_3.6H_2O$ (0.040 g, 0.109 mmol) and TREN-1-Bn-6-Me-HOPO-TAM (0.100 g, 0.114 mmol) in $H_2O$ (10 ml). The resulting pale yellow solution was heated under reflux for 2 h, during which time a cream precipitate developed. The solvent was removed and the residue suspended in iPrOH, sonicated and filtered three times. The resulting light brown solid was dried under vacuum. (Yield: 0.114 g, 95%). Anal. Calcd (Found) for GdH(TREN-1-Bn-6-Me-HOPO-TAM)($H_2O)_2.2H_2O$ $C_{43}H_{51}N_7O_{12}Gd.2H_2O$: C, 49.32 (48.95); H, 4.90 (4.09); N, 9.36 (8.91). FAB-MS (−): m/z: 975.2 $[M]^-$.

Example 12

Preparation of TREN-1-Me-3,2-HOPO-TAM-DME (27B)

(1) Preparation of Benzyl protected TREN-1-Me-HOPO-3,2-TAM-DME (Formula 27 in Scheme 3, R=—$CH_2CH_2N(CH_3)_2$)

1,1-dimethylethyldiamine (0.11 ml, 1.00 mmol) was added to a solution of TREN-Me-3,2-HOPO-TAM-Thiaz (1.00 g, 0.973 mmol) in $CH_2Cl_2$ (30 ml). The resulting mixture was left to stir under ambient conditions for 8 h, during which time the color changed from yellow to clear. The solvent was removed by rotary evaporation and the residue was purified by a gradient flash silica column (2-10% $CH_3OH$ and 1% $Et_3N$ in $CH_2Cl_2$). The solvents were removed to afford a white solid, which was taken up in MeOH (10 ml) and evaporated once again (repeated twice) in order to remove excess $NEt_3$ (Yield: 0.84 g, 85%). $^1H$ NMR ($CDCl_3$ with a trace of $NEt_3$ added to improve signal of DME protons, 500 MHz): δ=8.04 (t, 1H, TAM amide NH), 7.80 (m, 3H, TAM-H and HOPO amide NH), 7.68 (d, J=8.4 Hz, 1H, TAM-H), 7.57 (br t, 1H, TAM amide NH) 7.28-7.41 (m, 20H, Bn), 7.06 (d, J=7.2 Hz, 2H, HOPO-H), 6.61 (d, J=7.2 Hz, 2H, HOPO-H), 5.29 (s, 4H, HOPO Bn $CH_2$), 5.15 (s, 2H, TAM Bn $CH_2$), 5.06 (s, 2H, TAM Bn $CH_2$), 3.57 (s, 6H, HOPO $CH_3$), 3.45 (q, 2H, DME $CH_2$), 3.10 (m, 6H, TREN $CH_2$), 2.30 (m, 8H, TREN $CH_2$ and DME $CH_2$) 2.13 (s, 6H, DME $CH_3$) ppm. Anal. Calcd (Found) for $C_{60}H_{66}N_8O_{10}.2.5H_2O$: C, 65.29 (65.28); H, 6.44 (6.31); N, 10.15 (10.01). ES-MS (+): m/z: 1059.3$[M+H]^+$.

(2) Preparation of TREN-1-Me-3,2-HOPO-TAM-DME (27B)

10% Pd on carbon (0.10 g) was added to a solution of benzyl protected TREN-1-Me-HOPO-TAM-DME (0.826 g, 0.781 mmol) in AcOH (10 ml). The resulting mixture was stirred under an atmosphere of $H_2$ under ambient conditions for 2 days. The Pd/C was removed by filtration, and the solvent was removed by rotary evaporation. The remaining residue was converted to the $Cl^-$ salt by dissolving in MeOH (10 ml) and one drop of conc. HCl and the solvent removed (×3). Excess HCl was then removed by dissolving the residue in MeOH (10 ml) and removing the solvent under reduced pressure (×3). The remaining residue was taken up in MeOH (2 ml) and added to a rapidly stirring solution of $Et_2O$ (200 ml) to afford a white precipitate which was filtered and dried under vacuum. (Yield: 0.640 g, 95%). $^1H$ NMR ($D_2O$, 500 MHz): δ=7.01 (d, J=10.9 Hz, 1H, TAM-H), 6.97 (d, J=10.9 Hz, 1H, TAM-H), 6.88 (d, J=9.1 Hz, 2H, HOPO-H), 6.23 (d, J=9.10Hz, 2H, HOPO-H), 3.87 (m, 6H, TREN $CH_2$), 3.82 (t, J=7.4 Hz, 2H, DME $CH_2$), 3.70 (m, 6H, TREN $CH_2$), 3.48 (s, 6H, DME $CH_3$), 3.43 (t, J=7.4 Hz, 2H, DME $CH_2$), 2.97 (s, 6H, TREN $CH_3$), ppm. Anal. Calcd (Found) for $C_{32}H_{42}N_8O_{10}.2HCl3.5H_2O$: C, 46.05 (46.15); H, 6.16 (6.29); N, 13.42 (13.33). FAB-MS (+): m/z: 699$[M+H]^+$.

Example 13

Preparation of the Gadolinium(III) Ion Complex with TREN-1-Me-HOPO-TAM-DME (27C)

$GdCl_3.6H_2O$ (0.073 g, 0.195 mmol) was added to a solution of TREN-HOPO-TAM-DME (0.150 g, 0.195 mmol) in $H_2O$ (10 ml) and the solution stirred for 1 h. Imidazole (0.093 g, 1.17 mmol) was added and the solution heated to reflux for 2 h during which time a white solid precipitated from solution. The solvents were evaporated and the residue suspended in iPrOH, sonicated, filtered, and dried under vacuum. (Yield: 0.128 g, 74%). Anal. Calcd (Found) for Gd(L)($H_2O)_2$, $C_{32}H_{43}N_8O_{12}Gd$: C, 43.28 (42.97); H, 4.88 (4.87); N, 12.60 (12.33); Gd, 17.69 (18.14). ES-MS (+): m/z: 853 $[M+H]^+$.

The UV/Vis spectrum was identical to that of Gd-TREN-1-Me-HOPO-TAM at neutral pH.

Example 14

Preparation of TREN-1-Me-3,2-HOPO-TAM-PEG-5000 (Formula 47A)

(1) Preparation of Benzyl protected TREN-1-Me-3,2-HOPO-TAM-Thiazolide (Formula 25 in Scheme 3)

A solution of TREN(1-Me-HOPO)$_2$ (3.00 g, 4.77 mmol) in CH$_2$Cl$_2$ (150 ml) was added dropwise to a solution of BnTAMdiThiaz (20.77 g, 47.7 mmol) in CH$_2$Cl$_2$ (250 ml) over a period of 1 h. The resulting solution was then stirred for a further 8 h before purified (twice) by a gradient flash silica column (0-4% CH$_3$OH in CH$_2$Cl$_2$)). The solvents were removed under reduced pressure to afford a yellow foam. (Yield: 3.56 g, 68%). $^1$H NMR (CDCl$_3$, 500 MHz): δ=7.82 (t, J=5.3 Hz, 2H, HOPO amide NH), 7.78 (d, J=8.2 Hz, 1H, TAM-H), 7.22-7.41 (m, 20H, Bn), 7.18 (d, J=8.2 Hz, 1H, TAM-H), 7.08 (d, J=7.2 Hz, 2H, HOPO-H), 6.65 (d, J=7.2 Hz, 2H, HOPO-H), 5.30 (s, 4H, HOPO Bn CH$_2$), 5.11 (s, 2H, TAM Bn CH$_2$), 5.06 (s, 2H, TAM Bn CH$_2$), 4.38 (t, J=7.3 Hz, 2H, TAM thiaz), 3.57 (s, 6H, CH$_3$), 3.12 (m, 6H, TREN CH$_2$), 2.93 (t, J=7.3 Hz, 2H, TAM thiaz), 2.29 (m, 6H, TREN CH$_2$) ppm. Anal. Calcd (Found) for C$_{59}$H$_{59}$N$_7$O$_{10}$S$_2$: C, 65.00 (64.68); H, 5.45 (5.30); N, 8.99 (8.73). FAB-MS (+): m/z: 1090.5[M+H]$^+$.

(2) Preparation of Benzyl Protected TREN-1-Me-HOPO-TAM-PEG-5000 (Formula 27 in Scheme 3, R=(CH$_2$CH$_2$O)$_n$CH$_3$, average n=121)

PEG-5000 monoamine (1.85 g, 0.370 mmol) was added to a solution of benzyl protected TREN-1-Me-HOPO-TAM-thiazolide (0.4 g, 0.377 mmol) in dry CH$_2$Cl$_2$ (5 ml). The resulting solution was left stirring for several days at 313K under a nitrogen atmosphere. After 4 days, a few drops of Net3 and a catalytic amount of dimethylaminopyridine (DMAP) were added. After TLC indicated that the reaction was complete, the solvent was removed and the residue was purified by a gradient flash silica column (2-10% CH$_3$OH in CH$_2$Cl$_2$)) and sephadex LH-20 (solvent: MeOH) column chromatography until pure by GPC analysis. (Yield: 1.95 g, 91%). $^1$H NMR (CDCl$_3$ with AcOH added, 500 MHz): δ=8.12 (m, 4H, NH's), 7.70 (d, J=8.3 Hz, 1H, TAM-H), 7.54 (d, J=8.3 Hz, 1H, TAM-H), 7.26-7.37 (m, 20H, Bn), 7.06 (d, J=7.5 Hz, 2H, HOPO-H), 6.53 (d, J=7.5 Hz, 2H, HOPO-H), 5.30 (s, 4H, HOPO Bn CH$_2$), 5.12 (s, 2H, TAM Bn CH$_2$), 5.09 ppm. All other peaks are obscured by PEG and AcOH peaks in the between 2 and 4 ppm. MS-ES(+): m/z: 1582 (average mass), [M]$^{4+}$ with 121 —(CH$_2$CH$_2$O)— units. Peaks in this region were separated by 11 mass units, as expected for a PEG compound.

(3) Preparation of TREN-1-Me-HOPO-TAM-PEG-5000 (47A)

5% Pd on C (0.20 g) was added to a solution of benzyl protected TREN-1-Me-HOPO-TAM-PEG-5000 (2.00 g, 0.334 mmol) in AcOH (20 ml). The resulting mixture was stirred under an atmosphere of H$_2$ under ambient conditions for 3 days. The Pd/C was removed by filtration, and the solvent was removed by rotary evaporation. The remaining residue was converted to the Cl$^-$ salt by dissolving in MeOH (10 ml) and one drop of conc. HCl and the solvent removed (×3). Excess HCl was then removed by dissolving the residue in MeOH (10 ml) and removing the solvent under reduced pressure (×3). The remaining residue was taken up in MeOH (2 ml) and added to a rapidly stirring solution of Et$_2$O (200 ml) to afford a white precipitate, which was filtered and dried under vacuum. (Yield: 1.95 g, 91%). $^1$H NMR (D$_2$O, 500 MHz): δ=6.96 (d, 1H, TAM-H), 6.91 (d, 1H, TAM-H), 6.73 (d, J=7.2 Hz, 2H, HOPO-H), 6.04 (d, J=7.2 Hz, 2H, HOPO-H), 3.2-2.8 (m, large integral, PEG and other protons) ppm. Anal. Calcd (Found) with 121 —(CH$_2$CH$_2$O)— units for C$_{271}$H$_{52}$ON$_7$O$_{131}$Cl: C, 54.17 (53.76); H, 8.72 (8.77); N, 1.63 (1.35).

Example 15

Preparation of the Gadolinium(III) Ion Complex with TREN-1-Me-3,2-HOPO-TAM-PEG-5000 (formula 47)

GdCl$_3$.6H$_2$O (0.0146 g, 0.0392 mmol) was added to a solution of TREN-1-Me-HOPO-TAM-PEG-5000 (0.220 g, 0.0392 mmol) in H$_2$O (10 ml). An excess of aqueous ammonia was added and the solution was heated to reflux for 2 h. The solution was filtered and the solvents removed from the filtrate by rotary evaporation. The product was purified by elution down a Sephadex LH-20 column, after which the solution was added to a rapidly stirring solution of Et$_2$O (200 ml) to afford a pale yellow precipitate, which was filtered off and dried under vacuum. (Yield: 0.196 g, 87%). Anal. Calcd (Found) with 121 —(CH$_2$CH$_2$O)— units for [Gd(L)] .NH$_4$.3NH$_4$Cl, C$_{271}$H$_{531}$N$_{11}$O$_{131}$GdCl$_3$: C, 51.63 (51.53); H, 8.49 (8.91); N, 2.44 (2.65); Gd, 2.49 (2.89). MS-ES-TOF (−): m/z: 3093 (median mass), both the mass and the isotope distribution correspond to [Gd(LH)+2Cl]$^{2-}$ with 121 —(CH$_2$CH$_2$O)— units. The UV/vis spectrum of this compound was identical to that of Gd-TREN-1-Me-HOPO-TAM at neutral pH.

Example 16

Preparation of TREN-1-Me-3,2-HOPO-TAM-PEG-2000 (46A)

(1) Preparation of TAM-Thiazolide-PEG-2000 (Formula 26 in Scheme 3, R=(CH$_2$CH$_2$O)$_n$CH$_3$, average n=42)

A solution of PEG-2000-monoamine (1.0 g, 0.5 mmol) in CH$_2$Cl$_2$ (50 ml) was added drop wise to a rapidly stirring solution of BnTAMdiThiaz (10.0 g, 17.5 mmol) in CH$_2$Cl$_2$ (150 ml) under an atmosphere of N$_2$. After 2 days, the solution was reduced in volume and purified by a gradient flash silica column (2-10% CH$_3$OH in CH$_2$Cl$_2$). The first yellow band was unreacted BnTAMdiThiaz, and was saved for future use. The second yellow band was the desired product: the solvents were removed to yield a thick yellow oil, which solidified on standing over 4 h (Yield: 1.08 g, 87%). $^1$H NMR (d$_6$-DMSO, 400 MHz): δ=8.06 (br s, 1H, NH), 7.88 (d, J=8.3 Hz, 1H, TAM CH), 7.33-7.38 (m, 10H, aromatic H), 7.20 (d, J=8.3 Hz, 1H, TAM CH), 5.10 (s, 4H, Bn CH$_2$), 4.37 (t, J=6.8 Hz, 2H, thiazolide CH$_2$), 3.55-3.70 (m, large integral, PEG H), 2.94 (t, J=6.8 Hz, 2H, thiazolide CH$_2$). Anal. Calcd (Found) with 42 —(CH$_2$CH$_2$O)— units for C$_{110}$H$_{192}$N$_2$O$_{46}$S$_2$: C, 56.39 (56.29); H, 8.26 (8.19); N, 1.20 (1.26). MS-ES (+): m/z: 1172 (average mass), [M]$^{2+}$ with 42 —(CH$_2$CH$_2$O)— units.

Peaks in this region are separated by 22 mass units, as expected for a PEG compound.

(2) Preparation of Benzyl protected TREN-1-Me-3, 2-HOPO-TAM-PEG-2000 (Formula 27 in Scheme 3, R=$(CH_2CH_2O)_nCH_3$, average n=42)

TAM-thiazolide-PEG-2000 (1.0 g, 0.42 mmol) was added to a solution of TREN(1-Me-HOPO)$_2$ (0.341 g, 0.54 mmol) in $CH_2Cl_2$ (20 ml). The resulting yellow solution was stirred under an atmosphere of $N_2$ until, after 2 days, the solution turned colorless. The product was purified by a gradient flash silica column (2-8% $CH_3OH$ in $CH_2Cl_2$). The solvents were removed to yield a white solid (Yield: 0.91 g, 85%). $^1$H NMR (d6-DMSO, 500 MHz): δ=8.36 (t, 1H, TAM amide NH), 8.18 (t, 1H, TAM amide NH), 8.15 (t, 2H, HOPO amide NH), 7.47 (d, J=8.9 Hz, 2H, HOPO CH), 7.26-7.40 (m, 22H, aromatic H), 6.23 (d, J=8.9 Hz, 2H, HOPO CH), 5.18 (s, 4H, HOPO Bn $CH_2$), 5.05 (s, 2H, TAM Bn $CH_2$), 5.03 (s, 2H, TAM Bn $CH_2$), 3.17-3.66 (m, PEG and TREN H) ppm. Anal. Calcd (Found) with 42 —$(CH_2CH_2O)$— units for $C_{141}H_{228}N_7O_{52}$: C, 59.35 (59.09); H, 8.05 (8.30); N, 3.44 (3.34). MS-ES (+): m/z: 1427 (average mass), $[M^{2+}+1]$ with 42 —$(CH_2CH_2O)$— units. Peaks in this region are separated by 22 mass units, as expected for a PEG compound.

(3) Preparation of TREN-1-Me-3,2-HOPO-TAM-PEG-2000 (46A)

5% Pd on carbon (0.15 g) was added to a solution of benzyl protected TREN-1-Me-3,2-HOPO-TAM-PEG-2000 (0.86 g, 0.167 mmol) in AcOH (10 ml). The resulting mixture was stirred under an atmosphere of $H_2$ under ambient conditions for 3 days. The Pd/C was removed by filtration, and the solvent was removed by rotary evaporation. The remaining residue was converted to the Cl$^-$ salt by dissolving in MeOH (10 ml) and one drop of conc. HCl and the solvent removed (×3). Excess HCl was then removed by dissolving the residue in MeOH (10 ml) and removing the solvent under reduced pressure (×3). The remaining residue was taken up in MeOH (2 ml) and added to a rapidly stirring solution of $Et_2O$ (200 ml) to afford a white precipitate which was filtered and dried under vacuum. (Yield: 0.65 g, 85%). $^1$H NMR (d$_6$-DMSO, 500 MHz): δ=9.09 (br s, 1H, TAM amide NH), 8.96 (br s, 1H, TAM amide NH), 8.66 (br s, 1H, HOPO amide NH), 7.33 (d, 1H, TAM-H), 7.31 (d, 1H, TAM-H), 7.11 (d, J=7.2 Hz, 2H, HOPO-H), 6.42 (d, J=7.2 Hz, 2H, HOPO-H), 3.22-3.71 (m, large integral, PEG and TREN H) ppm. Anal. Calcd (Found) with 42 —$(CH_2CH_2O)$— units for $C_{113}H_{203}N_7O_{52}HCl.3H_2O$: C, 52.56 (52.27); H, 8.20 (8.00); N, 3.80 (3.96). MS-ES (+): m/z: 1246 (average mass), $[M]^{2+}$ with 42 —$(CH_2CH_2O)$— units. Peaks in this region are separated by 22 mass units, as expected for a PEG compound.

Example 17

Preparation of the Gadolinium(III) Ion Complex with TREN-1-Me-3,2-HOPO-TAM-PEG-2000 (Formula 46)

$GdCl_3.6H_2O$ (0.043 g, 0.135 mmol) was added to a solution of TREN-1-Me-3,2-HOPO-TAM-PEG-2000 (0.35 g, 0.135 mmol) in $H_2O$ (10 ml). An excess of aqueous ammonia was added and the solution was heated to reflux for 2 h. The solution was filtered and the solvents removed from the filtrate by rotary evaporation. The product was purified by elution down a Sephadex LH-20 column, after which the solution was added to a rapidly stirring solution of $Et_2O$ (200 ml) to afford a pale yellow precipitate, which was filtered off and dried under vacuum. (Yield: 0.297 g, 84%). Anal. Calcd (Found) with 42 —$(CH_2CH_2O)$— units for $[Gd(L)].NH_4$ $NH_4Cl$, $C_{113}H_{207}N_9O_{52}GdCl$: C, 49.96 (49.72); H, 7.68 (7.48); N, 4.63 (4.19); Gd, 5.79 (5.55). MS-ES-TOF (−): m/z: 2681 (median mass), both the mass and the isotope distribution correspond to $[Gd(LH)+Cl]^-$ with 42 —$(CH_2CH_2O)$— units.

Example 18

Preparation of TREN-1-Me-3,2-HOPO-TAM-O$_2$—NH$_2$ (27D)

(1) Preparation of Benzyl protected TREN-1-Me-3, 2-HOPO-TAM-O$_2$—NH$_2$ (Formula 27 in Scheme 3, R=$(CH_2CH_2O)_2CH_2CH_2NH_2$)

A solution of TREN-1-Me-3,2-HOPO-TAM-thiazolide (1.50 g, 1.41 mmol) in $CH_2Cl_2$ (100 ml) was added to a rapidly stirring solution of solution of 2-[2-(2-Aminoethoxy)-ethoxy]-ethylamine (10.46 g, 70.6 mmol) in $CH_2Cl_2$ (200 ml). The resulting clear solution was purified by a gradient flash silica column (2-10% $CH_3OH$ and 1% $Et_3N$ in $CH_2Cl_2$) The solvents were removed to yield a colorless oil. (Yield: 0.96 g, 61%). $^1$H NMR (d$_6$-DMSO, 400 MHz): δ=8.37 (br s, 1H, TAM NH), 8.18 (br s, 1H, TAM NH), 8.14 (br s, 2H, HOPO NH), 7.46 (d, J=6.8 Hz, HOPO H), 7.25-7.39 (m, 22H, aromatic H), 6.22 (d, J=6.9 Hz, HOPO H), 5.17 (s, 4H, Bn $CH_2$), 5.02 (s, 4H, Bn $CH_2$), 3.18-3.54 (m, 18H, $CH_2$ and HOPO $CH_3$) ppm. Anal. Calcd (Found) for $C_{62}H_{70}N_8O_{12}.2H_2O$: C, 64.46 (64.45); H, 6.46 (6.45); N, 9.70 (9.45). FAB-MS (+): m/z: 1119.7 $[M+H]^+$.

(2) Preparation of TREN-1-Me-3,2-HOPO-TAM-O$_2$—NH$_2$ (27D)

Benzyl protected TREN-1-Me-3,2-HOPO-TAM-O$_2$—NH$_2$ (0.83 g, 0.74 mmol) was dissolved in AcOH (10 ml) and concentrated HCl (10 ml) and stirred for 3 days. The solvents were removed, and the residual solid was dissolved in MeOH (2 ml), $H_2O$ (10 ml) and concentrated HCl (5 ml) for 10 h. After the removal of the solvent, the residue was dissolved in MeOH (10 ml) and the solvent again removed by rotary evaporation. This procedure was repeated six times, with 2 drops 6 M HCl being added to the first three solutions. The final residue was dissolved in MeOH (3 ml) and added to a rapidly stirring solution of $Et_2O$ (150 ml) to afford a white powder which was filtered, and dried under vacuum. (Yield: 0.48 g, 73%). $^1$H NMR (d$_6$-DMSO/D$_2$O, 500 MHz): δ=7.27 (d, 1H, TAM), 7.24 (d, 1H, TAM), 7.06 (d, J=7.4 Hz, 2H, HOPO), 6.35 (d, J=7.4 Hz, 2H, HOPO), 3.43-3.63 (m, aliphatic H) ppm. Anal. Calcd (Found) for $C_{34}H_{46}N_8O_{12}.2HCl.3H_2O$: C, 46.11 (46.48); H, 6.14 (6.16); N, 12.65 (12.21). FAB-MS (+): m/z: 759 $[M+H]^+$.

Example 19

Preparation of the Gadolinium(III) Ion Complex with TREN-1-Me-3,2-HOPO-TAM-O$_2$—NH$_2$ (27E)

Imidazole (0.058 g, 0.85 mmol) was added to a solution of $GdCl_3.6H_2O$ (0.060 g, 0.16 mmol) and TREN-HOPO-TAM-O$_2$—NH$_2$ (0.150 g, 0.169 mmol) in $H_2O$ (10 ml). The resulting pale yellow solution was heated under reflux for 2 h. The solvent was removed to yield a yellow residue which was suspended in —PrOH, sonicated and filtered three times. The resulting light brown solid was dried under vacuum. (Yield: 0.117 g, 73%). Anal. Calcd (Found) for Gd(TREN-HOPO-TAM-O$_2$—NH$_2$)(H$_2$O)$_2$ C$_{34}$H$_{47}$N$_8$O$_{14}$Gd: C, 43.03 (42.87); H, 4.99 (4.61); N, 11.81 (11.63). FAB-MS (+): m/z: 913.2 [M+H]$^+$.

Example 20

Preparation of TREN-1-Me-3,2-HOPO-TAM$_2$ (27H)

(1) Preparation of TAM-thiazolide-ethanolamine (27F)

A solution of ethanolamine (0.32 g, 5.26 mmol) in CH$_2$Cl$_2$ (100 ml) was added drop wise to a rapidly stirring solution of BnTAMdiThiaz (15.0 g, 26.3 mmol) in CH$_2$Cl$_2$ (150 ml) under ambient conditions. The reaction was stirred for 8 h, then the product was isolated by a gradient flash silica column (2-10% CH$_3$OH in CH$_2$Cl$_2$). The solvents were removed to yield a yellow oil which solidified upon standing over several hours (Yield: 2.17 g, 79%). $^1$H NMR (D$_2$O, 500 MHz): δ=8.17 (t, J=5.4 Hz, NH), 7.93 (d, J=8.2 Hz, TAM CH), 7.39 (m, 10H, Bn H), 7.23 (d, J=8.2 Hz, 2H, TAM CH), 5.14 (s, 2H Bn CH$_2$), 5.13 (s, 2H Bn CH$_2$), 4.40 (t, J=7.3 Hz, 2H, thiazolide CH$_2$), 3.62 (t, J=4.7 Hz, 2H, OCH$_2$), 3.39 (q, J=5.4 Hz, 2H, NCH$_2$), 2.97 (t, J=7.3 Hz, thiazolide CH$_2$) ppm. Anal. Calcd (Found) for C$_{25}$H$_{26}$N$_2$O$_5$S$_2$: C, 62.05 (61.81); H, 5.01 (5.06); N, 5.36 (5.14) ppm. FAB-MS (+): m/z: 523[M+H]$^+$.

(2) Preparation of Benzyl Protected TREN-1-Me-3,2-HOPO-TAM$_2$ (27G)

A solution of TAM-thiaz-ethanolamine (1.50 g, 2.81 mmol) in CH$_2$Cl$_2$ (100 ml) was added dropwise to a rapidly stirring solution of tris(2-aminoethylamine) (TREN, 0.229 g, 1.57 mmol) in CH$_2$Cl$_2$ (100 ml). Small extra portions of 1-Bn-6-Me-3,2-HOPO-thiazolide were also added as deemed necessary by TLC. The reaction mixture was purified by a gradient flash silica column (2-10% CH$_3$OH and 1% Et$_3$N in CH$_2$Cl$_2$). The solvents were then removed to yield a colorless oil. (Yield: 0.63 g, 34% relative to TREN). $^1$H NMR (d$_6$-DMSO, 400 MHz): δ=8.31 (br t, 2H, TAM NH), 8.22 (br t, 2H, TAM NH), 8.14 (t, 1H, HOPO NH), 7.45 (d, J=7.0 Hz, 1H, HOPO CH) 7.29-7.40 (m, 29H, aromatic H), 6.21 (d, J=7.0 Hz, 1H, HOPO CH), 5.19 (s, 2H, HOPO Bn CH$_2$), 5.03 (s, 8H, TAM Bn CH$_2$), 4.75 (t, 2H, OH), 3.45 (s, 3H, HOPO CH$_3$), 3.24-3.33 (m, 20H, CH$_2$) ppm. Calcd (Found) for C$_{68}$H$_{71}$N$_7$O$_{13}$.2H$_2$O: C, 66.38 (66.60); H, 6.14 (6.20); N, 7.97 (7.83). FAB-MS (+): m/z: 1194.6 [M+1]$^+$.

(3) Preparation of TREN-1-Me-3,2-HOPO-TAM$_2$ (27H)

Benzyl protected TREN-1-Me-3,2-HOPO-TAM$_2$ (0.470 g, 0.382 mmol) was dissolved in AcOH (5 ml) and concentrated HCl solution (5 ml), and left stirring for 3 days under ambient conditions. The solvents were removed, and the residue was dissolved in 6.0 M HCl and left stirring for another 24 h (this was in order to hydrolyze acetyl ester that had been found to have formed during the deprotection reaction). The solvents were removed, and the residue taken up in MeOH (5 ml), which was subsequently removed by rotary evaporation (×3). The residue was then taken up in MeOH (3 ml) and added to rapidly stirring solution of Et$_2$O (200 ml), to yield a white precipitate which was filtered and dried under vacuum (Yield 0.248 g, 77%). $^1$H NMR (d$_6$-DMSO, 300 MHz): δ=9.14 (br s, 2H, TAM NH), 8.93 (br s, 2H, TAM NH), 8.70 (br s, 1H, HOPO NH), 7.41 (d, J=8.8 Hz, 2H, TAM CH), 7.34 (d, J=8.8 Hz, 2H, TAM CH), 7.13 (d, J=7.3 Hz, 1H, HOPO CH), 6.43 (d, J=7.3 Hz, 1H, HOPO CH), 3.36-3.75 (m, 23H, aliphatic H) ppm (Also evidence of approx 0.15 equiv. of NEt$_3$, presumably present from the column in previous reaction). Calcd (Found) for C$_{33}$H$_{42}$N$_7$O$_{13}$Cl.0.15NEt$_3$HCl2.5H$_2$O: C, 48.14 (48.36); H, 5.89 (5.91); N, 11.84 (11.84). FAB-MS (+): m/z: 744 [M+H]$^+$.

Example 21

Preparation of TREN-Gly-1-Me-3,2-HOPO (6A)

(1) Preparation of Gly-1-Me-3,2-HOPO (4A)

1-Me-HOPO-3,2-thiazolide (Formula 4, Scheme 1) (3.00 g, 8.334 mmol) was dissolved in CH$_2$CH$_2$ (50 ml) and i-PrOH (50 ml) and added to a solution of NaOH (0.350 g, 8.60 mmol) and glycine (0.626 g, 8.334 mmol) in water (3 ml). The yellow mixture was then stirred for 24 h, during which time it turned colorless, and TLC indicated that the reaction was complete. The reaction mixture was purified by a gradient flash silica column (2-10% CH$_3$OH in CH$_2$Cl$_2$). The solvent was evaporated and the product purified further by recrystallization from hot EtOH to afford white needles (Yield: 2.06 g, 78%). $^1$H NMR (CDCl$_3$, 300 MHz): δ=8.51 (t, J=5.4 Hz, 1H, NH), 7.33-7.49 (m, 5H, Bn), 7.12 (d, J=7.2 Hz, 1H, HOPO CH), 6.78 (d, J=7.2 Hz, 1H, HOPO CH), 5.43 (s, 2H, BnCH$_2$), 4.05 (d, J=5.4 Hz, 2H, glycine CH$_2$), 3.61 (s, 3H, N—CH$_3$) ppm. Anal. Calcd (Found) for C$_{16}$H$_{16}$N$_2$O$_5$: C, 60.75 (60.84); H, 5.10 (5.11); N, 8.86 (8.70). EI-MS (+): m/z: 317 [M +H]$^+$.

(2) Preparation of Benzyl Protected TREN-Gly-1-Me-HOPO (5A)

N-hydroxysuccinimide (0.534 g, 4.64 mmol) was added to a solution of Gly-1-Me-HOPO (1.220 g, 3.87 mmol) in dry THF (60 ml) under a nitrogen atmosphere. After stirring for 20 min, dicyclohexylcarbodiimide (DCC, 0.956, 4.64 mmol) and dimethylaminopyridine (DMAP, 0.044 g, 0.46 mmol) were added. After 9 h, a white precipitate of dicyclohexylurea (DCU) had formed and the formation of the NHS-activated ester was judged to be complete by TLC. TREN (0.141 g, 0.967 mmol, 0.25equiv.) was added. The solvent was evaporated and the residue taken up in a 1.0M aqueous solution of HCl (50 ml). The suspension was filtered and the filtrate washed with CH$_2$Cl$_2$ (2×50 ml). The combined organic fractions were then back-extracted once with 1.0 M HCl (50 ml). 10M NaOH was added drop-wise to the combined aqueous fractions until the pH reached 11. The aqueous fractions were then extracted with CH$_2$Cl$_2$ (10×50 ml) and EtOAc (3×50 ml). The organic extracts were combined, dried (Na$_2$SO$_4$) and evaporated to dryness. The product was perified by a gradient flash silica column (2-8% CH$_3$OH in CH$_2$Cl$_2$). Evaporation of the solvent afforded a white foam (Yield: 0.753 g, 56%). $^1$H NMR (CDCl$_3$, 400 MHz): δ=8.58 (t, J=5.4 Hz, 3H, HOPO-glycine NH), 7.27-7.51 (m, 18H, Bn and glycine-TREN NH), 7.00 (d, J=7.2 Hz, 3H, HOPO), 6.59 (d, J=7.2 Hz, 3H, HOPO), 5.42 (s, 6H, Bn CH$_2$), 3.85 (d, J=5.4 Hz, 6H, glycine CH$_2$), 3.51 (s, 9H, N-CH$_3$), 3.20 (m, 6H, TREN NHCH$_2$), 2.51 (m, 6H, TREN NCH$_2$) ppm. Anal. Calcd (Found) for $C_{54}H_{60}N_{10}O_{12}.2H_2O$: C, 60.21 (59.96); H, 5.99 (5.96); N, 13.00 (12.93). FAB-MS (+): m/z: 1041.5 $[M+H]^+$.

(3) Preparation of TREN-Gly-1-Me-3,2-HOPO (6A)

TREN-Gly-1-Me-3,2-HOPO-Bn (0.650 g, 0.624 mmol) was dissolved in a mixture of MeOH (325 ml) and EtOH (325 ml) and added to a slurry of 5% Pd on C (0.65 g) in EtOH (65 ml). The reaction was stirred under an atmosphere of hydrogen for 6 h. The solution was filtered and the solvent removed by evaporation to afford a white solid (Yield: 0.296 g, 62%). This solid was found to be hygroscopic, and was therefore stored in a vacuum desiccator. $^1$H NMR ($d_6$-DMSO, 400 MHz): δ=8.71 (br s, 3H, HOPO-glycine NH), 7.95 (br s, 3H, glycine-TREN NH), 7.17 (d, J=7.3 Hz, 3H, HOPO), 6.52 (d, J=7.3 Hz, 3H, HOPO), 3.92 (br s, 6H, glycine $CH_2$), 3.46 (s, 9H, N-$CH_3$), 2.54 (br s, 6H, TREN $CH_2$) ppm. Anal. Calcd (Found) for $C_{33}H_{42}N_{10}O_{12}.3.5H_2O$: C, 47.54 (47.49); H, 5.92 (5.46); N, 16.80 (16.48). FAB-MS (+): m/z: 771 $[M+H]^+$.

Example 22

Preparation of the Gadolinium(III) Ion Complex with TREN-Gly-1-Me-3,2-HOPO (7A)

$GdCl_3.6H_2O$ (0.0327 g, 0.124 mmol) was dissolved in a solution of TREN-Gly-1-Me-3,2-HOPO (0.100 g, 0.138 mmol) in $H_2O$ (30 ml). Then an excess of aqueous ammonia solution was added to yield a light yellow precipitate. The suspension was heated under reflux for 2 h. After cooling, the solution was reduced in volume and the product filtered and dried under vacuum. (Yield: 0.079 g, 71%). Anal. Calcd (Found) for Gd(TREN-Gly-1-Me-3,2-HOPO)$(H_2O)_2.3H_2O$, $C_{33}H_{43}N_{10}O_{14}Gd.3H_2O$: N, 13.80 (13.37); Gd, 15.49 (15.35). FAB-MS (+): m/z: 924 $[M]^+$.

Example 23

Figure 16:
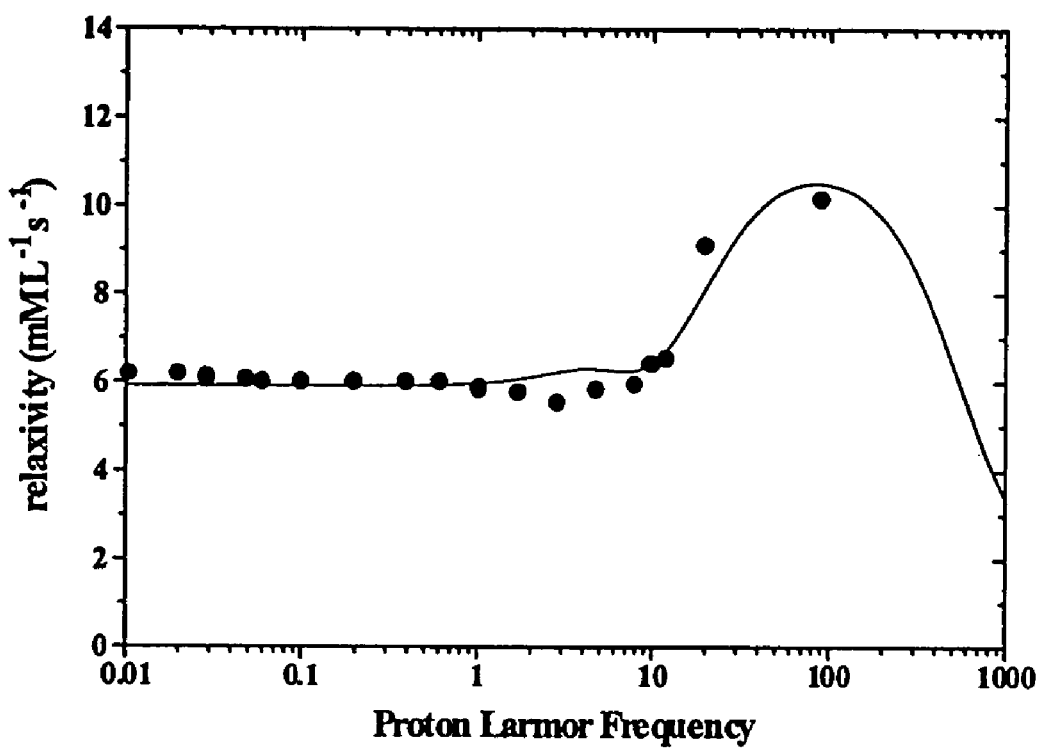
FIG. 16 is a NMRD profile of 47 in water at 25° C. and pH=7.4. Curve fitted with r=3.1 Å, q=1, $\tau_R$=300 ps, $\tau_M$=31 ns (from $^{17}$O NMR), $\tau_V$=27 ns, $\Delta^2$=8.4×10$^{19}$, a=4.0 Å, D=2.24× 10$^{-5}$ cm$^2$s$^{-1}$.

Nuclear Magnetic Resonance Dispersion (NMRD) Study on Poly (Ethylene Glycol) Functionalized Gd(III) Complexes The relaxivity parameters associated with Gd-TREN-1-Me-3,2-HOPO-TAM-PEG-5000 were monitored by fitting the Nuclear Magnetic Resonance Dispersion (NMRD) profile with a theoretical curve generated from a given set of relaxivity parameters. FIG. 16 below shows the NMRD profile of Gd-TREN-1-Me-3,2-HOPO-TAM-PEG-5000 in water at 25° C. and pH=7.4. Solid curve fitted with r=3.1 Å, q=1, $τ_R$=300 ps, $τ_M$=31 ns (from $^{17}$O NMR), $τ_V$=24 ns, $Δ^2$=7.3× $10^{19}$, a=4.0 Å, D=2.24×$10^{-5}$ $cm^2s^{-1}$. The fit is relatively poor, which may reflect a large degree of extra relaxivity due to the PEG chain organizing a network of hydrogen-bonded water molecules in the proximity of the metal center. This "second-sphere" relaxivity cannot be accounted for quantitatively and will most likely be reflected in the values for $τ_R$ or the zero-field value of the electronic relaxation time, $τ_{S0}$ being longer than in reality. Nevertheless, by far the best fit was obtained with q=1, in agreement with the value obtained from the $^{17}$O NMR study. In fact, the fit with q=2 (dotted line) is of very poor quality and forces $τ_R$ to assume a value unreasonably low (147 ns) for a complex of this molecular size.

Example 24

Figure 17:
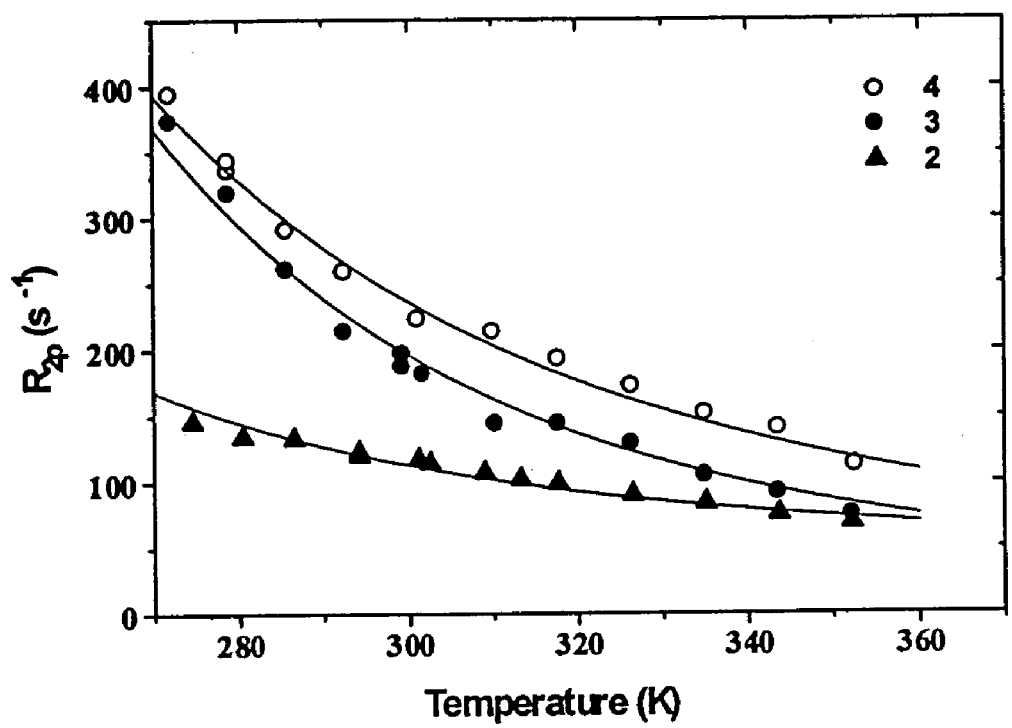
FIG. 17 is a graphical display of the $^{17}$O NMR transverse relaxation rates as a function of temperature (273-355 K), measured at 2.1 T (90 MHz proton Larmor frequency) for 21 mM aqueous solutions of the complexes: (a) Gd-TREN-bisHOPO-TAM-Me, pH=7.4, curve fitted with q=2, $\Delta^2$=1.9× 10$^{20}$ s$^{-2}$, $\tau_M$=8±1 ns (at 298 K) and $\Delta H_M$=2.4 kJ/mol; (b) 46, pH=7.6, curve fitted with q=1, $\Delta^2$=8.0×10$^{19}$ s$^{-2}$, $\tau_M$=19±2 ns (at 298 K) and $\Delta H_M$=10 kJ/mol and (c) 47, pH=7.5, curve fitted with q=1, $\Delta^2$=7.3×10$^{19}$ s$^{-2}$, $\tau_M$=31±2 ns (at 298 K) and $\Delta H_M$=6 kJ/mol.

$^{17}$O NMR Study of Water Exchange on Poly (Ethylene Glycol) Functionalized Gd(III) Complexes A variable temperature $^{17}$O NMR study of the transverse relaxation rate of $H_2^{17}O$ ($R_{2p}$) of Gd-TREN-1-Me-3,2-HOPO-TAM, Gd-TREN-1-Me-3,2-HOPO-TAM-PEG-2000 and Gd-TREN-1-Me-3,2-HOPO-TAM-PEG-5000 at 2.1 T was carried out. The profiles of $R_{2p}$ with temperature are shown in FIG. 17. Analysis of the profiles also allows the number of coordinated water molecules, q to be evaluated. Interestingly, it was found that q=2 for Gd-TREN-HOPO-1-Me-3,2-TAM, and q=1 for Gd-TREN-1-Me-3,2-HOPO-TAM-PEG-2000 and Gd-TREN-1-Me-3,2-HOPO-TAM-PEG-5000. The reduction in q that occurs in the presence of a PEG chain can be explained by partial displacement the two water molecules by the PEG oxygen donors. Significantly there appears to be an increase in $τ_M$ as the PEG chain is lengthened, with values of 8±1, 19±2 ns and 31±2 ns for Gd-TREN-1-Me-3,2-HOPO-TAM and Gd-TREN-1-Me-3, 2-HOPO-TAM-PEG-2000, Gd-TREN-1-Me-3,2-HOPO-TAM-PEG-5000 respectively.

Figure 18:
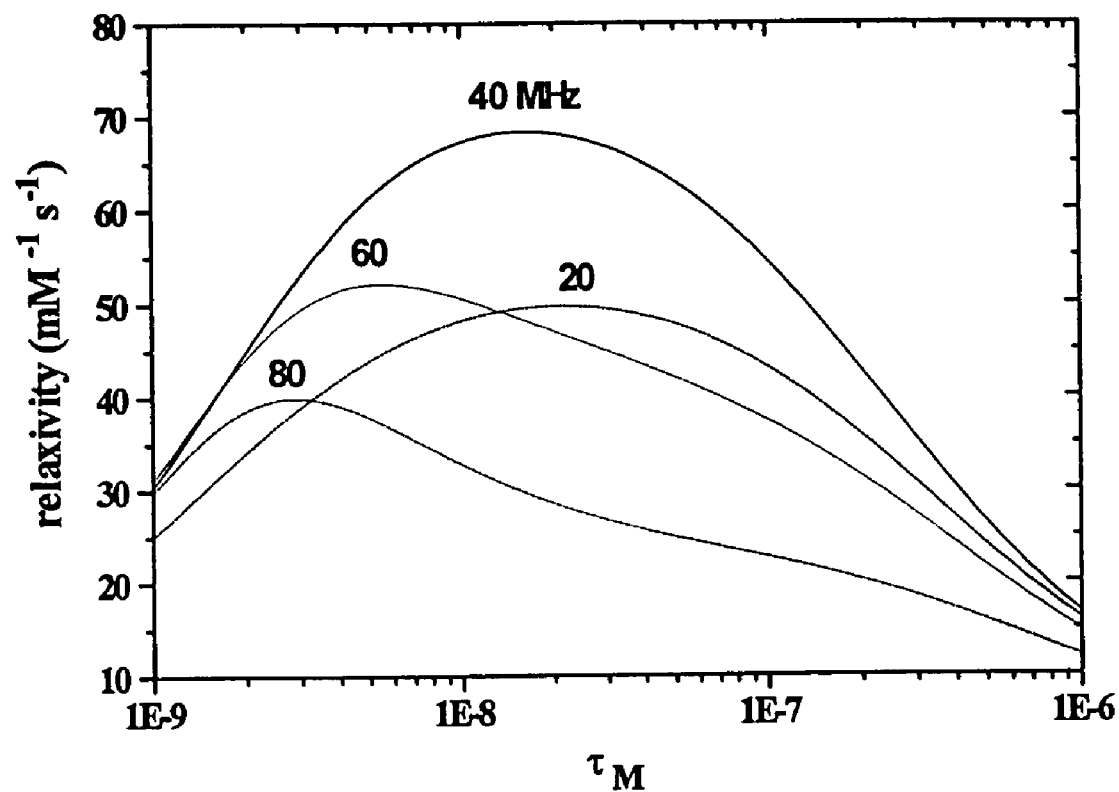
FIG. 18 displays the calculated relaxivity at 20, 40, 60 and 80 MHz as a function of $\tau_M$ for a macromolecular complex ($\tau_R$=10 ns). Typical parameters of DOTA-like Gd(III) complexes were utilized: q=1, r=3.0 Å, $\Delta^2$=1.5×10$^{19}$ s$^{-2}$, $\tau_V$=20 ps, a=3.8 Å, D=2.24×10$^{-5}$ cm$^2$s$^{-1}$.

The optimal value for $τ_M$ depends on several variables, in particular the field strength of the MRI scanner machine. Previous reports have suggested optimal $τ_M$ values of a few tens of nanoseconds. In order to investigate the likely optimal values of $τ_M$ for the complexes reported herein, the optimal $τ_M$ across a range of field strengths that are typical in MRI (FIG. 18) has been calculated. The results clearly show that the water exchange rates span a range which is optimal for clinical MRI.

Example 25

Effect of Binding to HSA on the Relaxivity of Poly (ethylene glycol) Functionalized Gd(III) Complexes The relaxivity of Gd-TREN-1-Me-3,2-HOPO-TAM-PEG-5000 at pH=7.5 is 9.1 $mM^{-1}s^{-1}$ (20 MHz, 25° C.), which compares to 8.8 $mM^{-1}s^{-1}$ (20 MHz, 25° C.) for Gd-TREN-HOPO-TAM. The increase in relaxivity observed upon addition of the PEG chain is very modest considering the large increase in molecular weight, reflecting the decrease in q and the effect of rapid internal motions of the PEG chain on $τ_R$.

Figure 19:
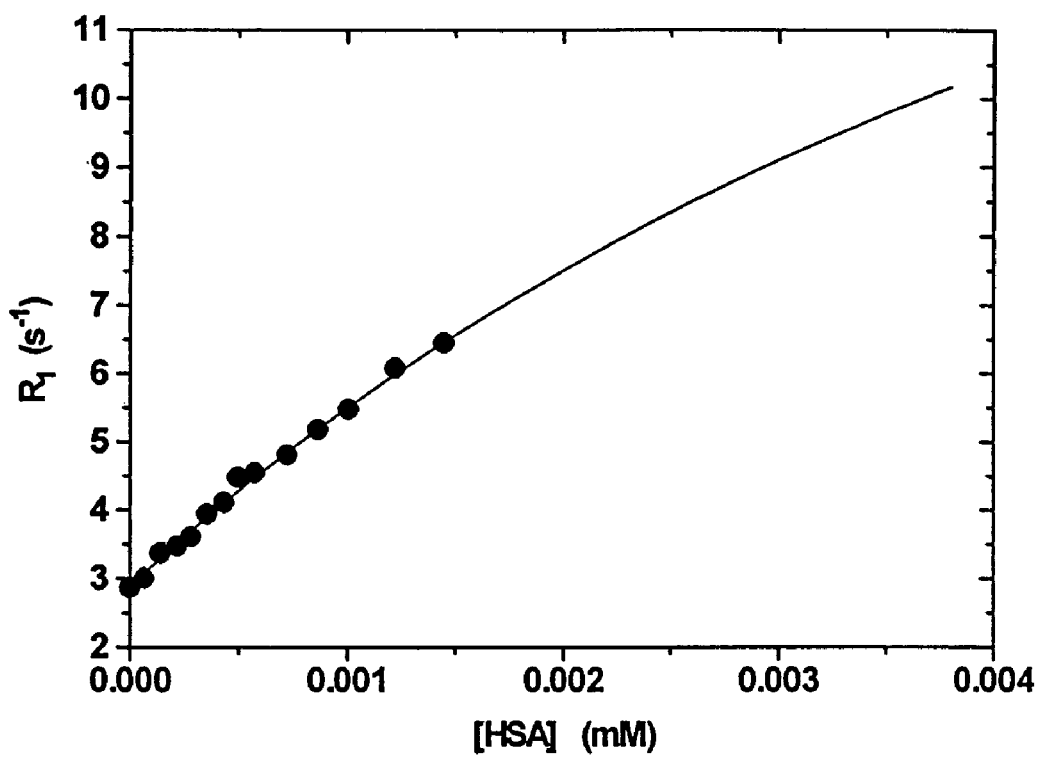
FIG. 19 displays the $^1$H longitudinal relaxation rate of H$_2$O as a function of HSA concentration. Experiment involved titration of a 0.25 mmol/L solution of the 47 with HSA at 20 MHz, 25° C. and pH=6.5. Analysis of data according to the PRE (Proton Relaxation Enhancement) method gives $K_A$=186±50 M$^{-1}$ and $r_{1p}$(bound)=74±14 mM$^{-1}$ s$^{-1}$. The relatively weak interaction results in large standard errors.

The longitudinal relaxation rate ($R_1$) of water protons in a 0.25 M solution of Gd-TREN-1-Me-3,2-HOPO-TAM-PEG-5000 was measured with increasing concentrations of HSA (FIG. 19) at 20 MHz and 25° C. The results clearly show an increase in $R_1$ as the HSA concentration is increased. From these data, the relaxivity of the TREN-1-Me-3,2-HOPO-TAM-PEG-5000-HSA adduct was calculated to be 74±14 $mM^{-1}s^{-1}$ with a formation constant, $K_a$ of 186±50 $M^{-1}$. This represents relatively weak binding, which would result in a mixture of bound and unbound complex under physiological concentrations of HSA. The value of relaxivity observed for this adduct is considerably higher than that of any other complexes reported to date (per $Gd^{III}$ center), reflecting an optimized water exchange rate and a slow rotational correlation time.

Example 26

Synthesis of 1,2-HOPOBn acid chloride (1) General

All chemicals were obtained from commercial suppliers (Aldrich or Fisher) and were used as received. 6-Hydroxypicolinic acid was purchased from Fluka. Me-3,2-HOPOBn-thiazolide was prepared as previously described (Xu et al., *J. Med. Chem.* 38: 2606-2614 (1995)). Reactions were carried out under an atmosphere of nitrogen. Flash silica gel chomatography was performed using Merck 40-70 mesh silica gel. Unless otherwise specified, all NMR spectra were recorded at ambient temperature on a Bruker DRX 500, AMX 400 or AMX 300 spectrometer in the University of California, Berkeley NMR laboratory. HPLC analyses were performed on a Varian Pro Star System with a Dynamax-60A C18-reversed phase column (mobile phase: 65% methanol in water). Microanalyses were performed by the Microanalytical Services Laboratory, College of Chemistry, University of California Berkeley. Mass spectra were recorded at the Mass Spectrometry Laboratory, College of Chemistry, University of California, Berkeley.

(2) Synthesis of 6-carboxy-1,2-HOPO 35A

Acetic anhydride (100 mL) was mixed with 30% $H_2O_2$ solution (25 mL) with cooling. The mixture was stirred for 4 h until a homogenous peracetic acid solution formed. This peracetic acid solution was added slowly with stirring to a solution of 6-hydroxy-picolinic acid (Fluka, 25 g, 0.18 mol) in a mixture of trifluoroacetic acid (150 mL) and glacial acetic acid (100 mL) (CAUTION! solid particles in the mixture cause vigorous oxygen evolution and can lead to an uncontrolled reaction). The mixture was stirred at room temperature for 1 h, and then heated slowly to 80° C. (oil bath temperature) and kept at 80° C. for 10 h. A white precipitate formed during this period, which was collected by filtration, washed with cold methanol, and dried. It was dissolved in aqueous 10% KOH, heated to 80° C. for 6 hours, and re-precipitated with concentrated HCl. The product was collected by filtration, washed with water and dried in a vacuum oven. Yield 20.5 g (0.132 mol, 73%). mp 176-177° C. Anal. Calc'd. (Found) for $C_6H_5NO_4$ (F.W. 155.15): C, 46.46 (46.31); H, 3.25 (3.45); N, 9.03 (9.12). $^1$H NMR (500 MHz, DMSO-$d_6$): δ 6.63 (dd, J=7.0, 1.5 Hz, 1H), 6.71 (dd, J=9.2, 1.5 Hz, 1H), 7.43 (dd, J=9.0, 7.1 Hz, 1H). 13C NMR (125 MHz, DMSO-d6): δ106.9, 120.5, 134.9, 137.3, 157.4, 163.3. IR (KBr pellet): 1734 $cm^{-1}$ (br, C=O); 1616 $cm^{-1}$ (m, C=O).

(3) Synthesis of 1-Benzyloxy-6-carboxy-2(1H)-pyridinone 36A 35A (15.5 g, 0.1 mol) and anhydrous potassium carbonate (27.6 g, 0.2 mol) was mixed with benzyl chloride (15.2 g, 0.12 mol) in methanol (250 mL). The mixture was refluxed for 16 h, filtered, and the filtrate was evaporated to dryness. The residue was dissolved in water (50 mL) and acidified with 6 N HCl to pH 2. The resulting white precipitate was isolated by filtration, washed with cold water, and dried in vacuum to yield 22.3 g (91%) of 36A, mp 176-177° C. Anal. Calc'd. (Found) for $C_{13}H_{11}NO_4$: C, 63.66 (63.75); H, 4.53 (4.55); N, 5.71 (5.52). $^1$H NMR (500 MHz, DMSO-$d_6$): δ 5.26 (s, 2H, CH2), 6.54 (dd, J=6.7, 1.1 Hz, 1H), 6.73 (dd, J=9.2, 1.6Hz, 1H), 7.39-7.51 (m, 6H). $^{13}$C NMR (125 MHz, DMSO-$d_6$): δ 77.9, 106.0, 124.1, 128.5, 129.1, 129.6, 133.8, 138.7, 140.4, 157.6, 161.7.

(4) Synthesis of 1,2-HOPOBn acid chloride 37A

To a suspension of bezyloxy1,2-HOPO carboxylic acid (5.0 g, 20 mmol) in toluene or benzene (50-70 mL), excess oxalyl chloride (5.0 g) was added while stirring. Gas was evolved and the suspension became clear upon the addition of a drop of DMF as a catalyst. The mixture was then warmed to 60° C. (oil bath) for 4-6 h. The solvent was removed by rotary evaporation, leaving a pale brown oil. After co-evaporation twice with toluene (5 mL), the residue was dissolved in dry THF, passed though a flash silica gel plug and eluted with dry THF. The 1,2-HOPOBn acid chloride so obtained after the solvent was removed under reduced pressure, was a thick, pale yellow oil: crude yield 5.0 g (95%). The crude product was used directly for reaction without further purification. $^1$H NMR (300 MHz, CDCl$_3$): δ5.32 (s, 2H, CH2), 6.88(d, J=7.0 Hz, 1 H), 6.726(d, J=9.0 Hz, 1 H), 7.32-7.51(m, 6 H). $^{13}$C NMR (125 MHz, DMSO-$d_6$): δ 78.5, 112.2, 128.5, 128.6, 129.4, 130.3, 132.7, 136.4, 140.1, 158.1, 158.8.

Example 27

Synthesis of 3,4,3-LI(1,2-Me-3,2-HOPO)

(1) Synthesis of 3,4,3-LI(1,2-HOPO)Bn 38A

To a solution of crude 1,2-HOPOBn acid chloride (5.0 g, 19 mmol) and triethylamine (2.5 mL) in dry THF (60 mL), spermine (0.8 g, 4 mmol) was added in three portions while stirring. The mixture was heated at 60° C. (oil bath) overnight in a stoppered 100 mL round-bottomed flask. The solvent was then removed on a rotary evaporator, and the residue was partitioned into a mixture of water (50 mL) and dichloromethane (50 mL). The organic phase was separated and it was washed successively with 1 M NaOH (100 mL), 1 M HCL (100 mL), and saline solution (100 mL), and loaded onto a flash silica column. Elution with 2-6% methanol in dichloromethane allowed separation of the benzyl-protected precursor 3,4,3-LI-(1,2-HOPOBn) as a white foam. Yield 70%. $^1$H NMR (500 MHz, CDCl$_3$): δ 0.4-1.8(m, 16H), 2.8-3.6(m, 24H), 4.8-5.1(m, 2H), 4.88-5.05(m, 2H), 5.15-5.30(m, 4H), 5.30-5.45(m, 2H), 6.00-6.46(m, 4H), 6.55-6.70(m, 4H), 7.25-7.55(m, 24H), 8.72-8.95(m, 2H, NH). $^{13}$C NMR (125 MHz, DMSO-$d_6$): δ 23.4, 24.2, 24.5, 24.6, 26.4, 26.6, 26.7, 27.3, 27.7, 36.6, 36.7, 41.8, 42.0, 42.4, 43.7, 46.2, 47.4, 47.7, 48.1, 79.2, 102.7, 104.7, 123.1, 128.3, 128.4, 128.7, 129.2, 129.3, 129.4, 130.0, 130.1, 130.2, 130.3, 130.4, 132.8, 132.9, 133.0, 133.1, 138.2, 142.0, 142.5, 142.6, 143.3, 157.9, 158.1, 158.3, 160.4, 160.6, 161.2, 161.3. MS(FAB+): 1111.5(MH+).

(2) Synthesis of 3,4,3-LI(1,2-HOPO) 39A

The precursor, 3,4,3-LI-(1,2-HOPOBn) was deprotected at room temperature over four days by the action of 1:1 HCl (37%)/glacial HOAc. All of the volatiles were removed in vacuo, and the resulting residue was dissolved in a minimum amount of water, filtered and evaporated to dryness: yield 81%. $^1$H NMR (400 MHz, DMSO-$d_6$): δ 0.25-1.87(m, 8H), 2.81-3.63 (m, 24H), 6.11-6.22 (m, 3H), 6.29-6.34(m, 2H), 6.48-6.58(m, 4H), 7.31-7.42(m, 4H), 8.82(q, J=7.2 Hz,1H). 8.91(q, J=7.2 Hz,1H). $^{13}$C NMR (125 MHz, D$_2$O): δ 23.1, 23.7, 24.2, 25.4, 26.7, 36.6, 36.8, 41.9, 44.0, 45.8, 47.7, 48.1, 106.2, 106.5, 108.7, 109.0, 118.9, 120.1, 138.8, 139.0, 139.6, 140.0, 140.5, 159.2, 161.1, 161.2, 162.2. MS(FAB+): 751 (MH+). Anal. for $C_{34}H_{38}N_8O_{12}$.H2O.2HCl (841.68), Calc'd. (found): C, 48.52 (48.16); H, 5.03 (4.82); N, 13.31 (13.23).

(3) Synthesis of 3,4,3-LI-Bis(Me-3,2-HOPOBn) 41A

To a solution of spermine (0.5 g, 2.5 mmol) in dry dichloromethane (60 mL), Me-3,2-HOPO-thiazolide (2.0 g, 5.5 mmol) was added while stirring. The mixture was stirred at room temperature overnight, then washed with 1 M KOH solution (30 mL×3). The organic phase was then dried in vacuum, leaving a pale brown oil: yield 85%. $^1$H NMR(300 MHz, CDCl$_3$): δ 1.434(m, br, 4H), 1.506(quint, J=6.7 Hz, 4H), 2.443(t, J=6.7 Hz, 8H), 3.255(q, J=6.7 Hz, 4H), 3.575(s, 6H), 5.341(s, 4H, OCH2), 6.725(d, J=7.2 Hz, 2H), 7.101(d, J=7.2 Hz, 2H), 7.2-7.5(m, 10H), 8.095(t, J=5.3 Hz, 2H). $^{13}$C NMR (125 MHz, CDCl$_3$): δ 27.25, 28.74, 37.43, 37.69, 46.84, 49.22, 74.56, 104.66, 128.52, 128.60, 128.81, 130.72, 132.00, 136.12, 146.08, 159.42, 163.16. MS(FAB+): 685.3 (MH+).

(4) 3,4,3-LI(1,2-Me-3,2-HOPO)Bn 41B

The crude 3,4,3-LI-Bis(Me-3,2-HOPO Bn), 41A, (0.82 g, 1.2 mmol) was dissolved in dry THF (50 mL) containing triethylamine (1.2 mL) and slowly added over 4 h to a solution of crude benzyloxy 1,2-HOPO acid chloride (1.7 g, 6.4 mmol) in dry THF (60 mL). The reaction mixture was maintained overnight at 60° C. After removing the solvents, the residue was partitioned into a mixture of water (50 mL) and dichloromethane (50 mL). The resulting organic phase was washed successively with 1 M NaOH (100 mL), 1 M HCl (100 mL), and saline water (100 mL), and loaded onto a flash silica column. Elution with 3-8% methanol in dichloromethane allowed the separation of the benzyl-protected precursor as white foam: yield 75%. $^1$H NMR(500 MHz, CDCl$_3$): δ0.9-1.6(m, 16H), 2.65-3.45(m, 24H), 3.546(s, 6H), 4.90-5.02(m, 4H), 5.20-5.6(m, 8H), 5.80-6.10(m, 4H), 6.54-6.80(m, 8H), 7.07-7.11(m, 4H), 7.15-7.51(m, 20H), 7.75 (m, br, 2H), 7.99(m, br, 1H). $^{13}$C NMR (125 MHz, CDCl$_3$): δ 24.99, 26.35, 26.65, 27.66, 36.47, 36.60, 36.68, 37.39, 41.80, 43.68, 45.61, 47.85, 74.39, 74.42, 74.75, 74.82, 78.88, 79.03, 104.19, 104.22, 104.35, 104.40, 122.51, 128.18, 128.20, 128.24, 128.41, 128.44, 128.47, 128.50, 128.54, 128.70, 128.73, 128.75, 129.86, 129.91, 131.95, 133.11, 142.81, 157.80 157.93, 159.14, 159.26, 161.42, 163.04, 163.12. MS(FAB+):1139.8.

(5) Synthesis of 3,4,3-LI(1,2-Me-3,2-HOPO) 43A

The benzyl-protected precursor 3,4,3-LI(1,2-Me-3,2-HOPO)Bn was deprotected in the same manner as 3,4,3-LI-(1,2-HOPO), above. The crude product was dissolved in a minimum amount of distilled water. Pure 3,4,3-LI(1,2-Me-3,2-HOPO) was precipitated as a beige solid upon cooling. The solid was filtered and dried under vacuum: yield 73% (based on spermine). $^1$H NMR(500 MHz, DMSO-d$_6$): δ 1.2-1.85(m, 16H), 2.85-3.35(m, 24H), 3.453(s, 6H), 6.10-6.52 (m, 6H), 7.10-7.41(m, 4H), 8.32(m, 1H). $^{13}$C NMR (500 MHz, D$_2$O/NaOD): δ 23.85, 24.02, 24.14, 24.19, 24.54, 24.83, 25.05, 26.89, 27.06, 28.13, 28.30, 35.67, 35.71, 36.47, 36.51, 36.58, 37.55, 42.93, 43.04, 43.16, 44.76, 44.90, 44.93, 45.11, 46.77, 48.34, 48.41, 48.67, 105.74, 106.15, 106.22, 106.44, 106.93, 107.14, 114.87, 114.96, 115.02, 115.87, 116.17, 119.61, 119.98, 132.70, 132.80, 133.06, 142.87, 143.12, 160.37, 161.93, 162.21, 164.41, 164.47, 165.60, 165.75, 169.49, 169.64. MS(FAB+):779.4(MH+), Anal. for C$_{36}$H$_{42}$N$_8$O$_{12}$.3H$_2$O.2HCl (905.76), Calc'd. (found): C, 47.74 (48.05); H, 5.56(5.22); N, 12.37 (12.16).

The purity of compound 43A was confirmed by analytical HPLC. The chromatogram indicates that the purity of the compound is above 99%.

Example 28

Synthesis of 2,3-Dimethyl-5-benzyloxy-6-carboxy-4-pyrimidinone

(1) Preparation of tetrahydropyran-2-yloxy-acetic acid ethyl ester (Formula 28, Scheme 4)

To a stirred solution of ethyl glycolate (35.3 g, 0.339 mol) containing a few crystals of p-toluene sulfonic acid, 3,4-dihydropyran (30.0 g, 0.357 mol) was added dropwise (15 g over one hour followed by 15 g over 30 min). After stirring overnight at room temperature, the mixture was diluted with diethyl ether (80 mL) and washed with a NaHCO$_3$ solution (from 30 mL sat. NaHCO$_3$ and 10 mL water). The organic layer was separated and dried (Na$_2$SO$_4$) followed by evaporation of the ether. The residue was distilled under high vacuum to give 58.4 g (91.5%) of 28 as a clear liquid. $^1$H NMR (CDCl$_3$, 400 MHz)δ: 1.29 (t, 3H, J=7.1 Hz, CH$_3$), 1.53-1.95 (m, 6H, 3,4,5-THP-CH$_2$'s), 3.50-3.55 (m, 1H, 6-THP-CH$_2$), 3.83-3.89 (m, 1H, 6-THP-CH$_2$), 4.19 (s, 2H, OCH$_2$CO$_2$R), 4.20 (t, 2H, J=7.1 Hz, CH$_2$Me), 4.75 (m, 1H, THP-CH). $^{13}$C NMR (CDCl$_3$, 100 MHz) δ: 14.1, 18.7, 25.2, 30.0, 60.7, 61.9, 63.8, 170.4.

(2) Preparation of 2-Methyl-3H-5-tetrahydropyran-2-yloxy-6-tetrahydropyran-2-yloximethyl-4-pyrimidinone 29

THPO-ethyl glycolate (34.0 g, 0.195 mol) in ether (180 mL) was stirred with Na shot (2.24 g, 0.0974 mol) for 20 hrs under a N$_2$ atmosphere, resulting in a yellow solution. NaH (0.54 eq.) can be used in place of Na, but usually requires the addition of 2-5% m/m EtOH to promote the reaction. The ether was removed and the residue covered with abs. ethanol (20 mL). An acetamidine solution was prepared from acetamidine.HCl (9.32 g, 0.0989 mol), which was stirred for 2 hr in sodium ethoxide in ethanol (130 mL, by addition of 2.36 g of Na). This suspension was filtered onto the ethanol covered residue from above and the filter cake washed with ethanol (5 mL). The reaction mixture was then stirred and heated at reflux 3.5 hr, cooled to room temperature and the solvent evaporated. The residue was dissolved in CH$_2$Cl$_2$ (80 mL) and HOAc was added (to pH 6, wet pH paper). After washing with water (2×80 mL) the organic layer was dried (Na$_2$SO$_4$) and most of the solvent removed. To the viscous CH$_2$Cl$_2$ solution, hexanes (100 mL) was added, producing a white precipitate which was filtered and washed with hexanes to afford 2, 20.6 g (65.2%). Mp: 113-114° C. (+)FABMS: m/z 325 +. $^1$H NMR (CDCl$_3$, 300 Mhz): δ 1.4-2.0 (m, 12H, 3,4,5-THP-CH$_2$), 2.42 (s, 3H, 2-CH$_3$), 3.50-356 (m, 2H, 6-THP-CH$_2$), 3.86-3.96 (m, 2H, 6-THP-CH$_2$), 4.44-4.81(4 d's, 2H, CH$_2$-OTHP), 4.79 (br m, 1H, THP-CH), 5.83 (br m, 1H, THP-CH), 11.44 (br s, 1H, NH). $^{13}$C NMR (CDCl$_3$, 100 MHz): δ 10.5, 18.5, 18.5, 19.1, 19.3, 21.1, 25.0, 25.38, 25.40, 29.9, 30.3, 30.4, 61.9, 62.2, 62.70, 62.74, 63.6, 63.8, 82.8, 98.4, 98.6, 98.63, 98.7, 138.58, 138.63, 152.4, 152.9, 161.6. Anal. Calcd (found) for C$_{15}$H$_{24}$N$_2$O$_5$: C, 59.24 (59.10); H, 7.46 (7.51); N, 8.64(8.94).

(3) Preparation of 2,3-Dimethyl-5-tetrahydropyran-2-yloxy-6-tetrahydropyran-2-yloximethyl-4-pyrimidinone 30

The THP-protected pyrimidine 29 (17.9 g, 54.9 mmol) dissolved in DMF (70 mL) was dripped into a slurry of NaH (2.30 g, 60% in oil, 57.5 mmol) in DMF (100 mL) maintaining a gentle effervescence. The reaction was stirred a for another 10 min then MeI (3.45 mL, 55.4 mmol) was added. After stirring 18 hr a few drops of methanol were added, followed after a few minutes by evaporation of the solvent under reduced pressure. The residue was dissolved in CHCl$_2$ (150 mL) and washed with water (3×150 mL). The solvent was removed and the residue dissolved in acetonitrile, then washed with hexanes (50 mL). After removal of the solvent this afforded 16.2-18.6 g (87-100%) of the crude product (>90% pure by $^1$H NMR). $^1$H NMR (CDCl$_3$, 400 MHz): δ

1.52-1.89 (m, 12H, 3,4,5-THP-CH$_2$), 2.49 (s, 3H, 2-CH$_3$), 3.49 (s, 3H, N-Me), 3.49-3.55 (m, 2H, 6-THP-CH$_2$), 3.92-3.96 (m, 2H, 6-THP-CH$_2$), 4.39-4.82 (m, 3H, CH$_2$—OTHP+THP-CH), 5.77 (br s, 1H, THP-CH).

(4) Preparation of 2,3-Dimethyl-5-hydroxy-6-(hydroxymethyl)-4-pyrimidinone.HCl (31.HCl).

Method A. The protected pyrimidine 30 (3.38 g, 10 mmol) was dissolved in $^1$PrOH (20 mL), diethyl ether (20 mL) and conc. HCl (1 mL). After standing at room temperature for 4 hr the crystallizing solution was refrigerated (0° C.) overnight. After filtration and washing with 1:1 $^1$PrOH/Et$_2$O (3×5 mL) then Et$_2$O (10 mL), the white solid was dried under high vacuum at room temperature to give 1.83 g (88.8%) of 31.HCl.

Method B. A Hydrogen chloride/dioxane solution (50 mL, 4M) was dripped into a solution of the protected pyrimidine 30 (30.1 g, 89 mmol) in EtOH (20 mL). A white solid rapidly precipitated and, after standing for a few hours at room temperature, the solid was filtered and washed with dioxane (3×10 mL) and diethyl ether (2×10 mL). Drying in vacuo overnight at 40° C. gave 16.08 g (88.8%) of 31HCl. This absorbs leq of H$_2$O upon standing exposed in air. Mp:>200° C. (dec.). (+)FABMS: m/z 171 {MH]+. $^1$H NMR (DMSO-d$_6$, 300 MHz): δ 2.68 (s, 3H, 2-Me), 3.49 (s, 3H, N-Me), 4.47 (s, 2H, CH$_2$O). $^{13}$C NMR (DMSO-d$_6$, 100 MHz): δ 18.7, 31.8, 54.1, 132.9, 138.0, 155.2, 157.2. Anal. Calcd (found) for C$_7$H$_{13}$ClN$_2$O$_4$: C, 37.43 (37.65); H, 5.83 (5.91); N, 12.47 (12.46).

(5) Preparation of 2,3-Dimethyl-5-benzyloxy-6-(hydroxymethyl)-4-pyrimidinone (32)

In a flask protected from direct light, DMF (300 mL), the above pyrimidine, 31.HCl, (14.14 g, 68.43 mmol) and K$_2$CO$_3$ (20.0 g, 145 mmol) were mechanically stirred for 1 hr at 65° C., followed by addition of BnCl (8.30 mL, 72.1 mmol) in one portion. Additional BnCl was added as the reaction progressed if TLC indicated it necessary. After stirring 8 hr at 65° C., the reaction mixture was cooled to room temperature, filtered (washing the cake with 2×20 mL DMF), and the solvent removed. The residue, in CH$_2$Cl$_2$ (100 mL), was filtered again and concentrated to ~20 mL at which point the cooled solution began to deposit a white crystalline mass. Dilution with diethyl ether (~100 mL) afforded slightly off-white crystals (10.1 g, 56.7%) of 5. Mp: 93-95° C. (+)FABMS: m/z 261 [MH]$^+$. $^1$H NMR (CDCl$_3$, 300 MHz): δ 2.49 (s, 3H, 2-Me), 3.19 (br s, 1H, OH), 3.53 (s, 3H, N-Me), 4.37 (s, 2H, CH$_2$O), 5.17 (s, 2H, CH$_2$Ph), 7.28-7.40 (m, 5H, Ph). $^{13}$C NMR (CDCl$_3$ 100 MHz): δ 22.9, 31.3, 58.8, 73.2, 128.3, 128.4, 128.6, 136.7, 137.5, 150.6, 153.9, 158.9. Anal. Calcd (found) for C$_{14}$H$_{16}$N$_2$O$_3$: C, 64.60 (64.62); H, 6.20 (6.04); N, 10.76 (10.82).

(6) Preparation of 2,3-Dimethyl-5-benzyloxy-6-carboxy-4-pyrimidinone (33)

The above pyrimidine, 32 (9.00 g, 34.6 mmol), TEMPO catalyst (55 mg), Adogen-464 phase transfer catalyst (690 mg) and NaBr (360 mg, 3.50 mmol) were combined in CH$_2$Cl$_2$ (400 mL) and water (10 mL). After cooling to 0° C. the reaction was stirred at 1500 r.p.m. while adding a cooled (10° C.) buffered bleach solution (125 mL commercial bleach+125 mL water +12.5 g NaHCO$_3$) keeping the reaction <4° C. (takes approx. 15 min). After a further 5 min, 2M NaOH solution was added until a solution of pH 10 was obtained. The CH$_2$Cl$_2$ layer was separated and extracted with basic water (pH 10, 100 mL). The combined aqueous solutions were washed with CH$_2$Cl$_2$ (50 mL). The aqueous phase was concentrated to ~200-250 mL and carefully acidified (conc. HCl) to pH 2, concomitant with precipitation. After standing at 5° C. overnight the white solid was filtered, washed with water and dried under high vacuum to give 5.20 g (54.9%) of 33. Mp: 180-181° C. (+)FABMS: m/z 275. 1H NMR (CDCl$_3$, 300 MHz): δ 2.53 (s, 3H, 2-Me), 3.55 (s, 3H, N-Me), 5.46 (s, 2H, BnCH$_2$), 7.30-7.38 (m, 3H, Ph), 7.49-7.52 (m, 2H, Ph). $^{13}$C NMR (DMSO-d$_6$, 100 MHz): δ 22.6, 31.2 73.3, 128.0, 128.2, 128.3, 136.9, 139.1, 143.0, 155.7, 159.2, 165.7. Anal. Calcd (found) for C$_{14}$H$_{14}$N$_2$O$_4$: C, 61.31 (61.36); H, 5.14 (5.06); N, 10.21(10.30).

Example 29

Synthesis of 2,3-Dimethyl-5-benzyloxy-6-carboxy-4-pyrimidinone (33) via 2,3-Dimethyl-5-benzyloxy-6-carboxy-4-pyrimidinone ethyl ester (35)

(1) Preparation of 2-Methyl-3H-5-benzyloxy-6-carboxy-4-pyrimidinone ethyl ester 34

Benzyl benzyloxyacetate (14.13 g, 55.13 mmol) and diethyloxalate (8.060 g, 55.13 mmol) and ethanol (0.2 mL) were stirred in dry THF (100 mL) with NaH (2.34 g, 60% in oil, 58.5 mmol) at room temperature for 24 hr. The THF was removed on a rotary evaporator and the residue dissolved in ethanol (100 mL) followed by addition of sodium ethoxide (3.75 g, 55.1 mmol) and acetamidine hydrochloride (5.21 g, 5.11 mmol). After stirring at 60° C. for 1.5 hr, the resulting suspension was cooled to room temperature and the solvent removed. The resulting oil was partitioned between CH$_2$Cl$_2$ (80 mL) and water (50 mL) and the pH adjusted to ~6. Filtration was performed if necessary. The CH$_2$Cl$_2$ was separated and combined with a CH$_2$Cl$_2$ (30 mL) wash of the aqueous phase. The CH$_2$Cl$_2$ solution was washed with water, separated, dried (Na$_2$SO$_4$) and the volume reduced until a thick oil was obtained. This was immediately shaken with diethyl ether (30 mL) and a white solid precipitated. After dilution with hexanes (~10% by volume) the solution was filtered and the cake washed with cold ether (3×10 mL). After drying, 7.2 g (45%) of 34 was obtained as a pale powder. Mp: 125-126° C. (+)FABMS: m/z 289 ([MH]+). $^1$H NMR (CDCl$_3$, 400 MHz): δ 1.31 (t, 3H, J=7.1 Hz, ethyl-Me), 2.50 (s, 3H, 2-Me), 4.35 (q, 2H, J=7.1 Hz, OCH$_2$), 5.25 (s, 2, NCH$_3$), 7.32-7.38, 7.44-7.46 (m, 3+2H, Ph), 13.14 (br t, 1H, amide NH). $^{13}$C NMR (CDCl$_3$, 100 MHz): δ 14.1, 21.3, 62.2, 74.5, 128.4, 128.5, 136.4, 141.9, 144.9, 153.6, 162.2, 164.2. Anal. Calcd (found) for C$_{15}$H$_{16}$N$_2$O$_4$: C, 62.49 (62.51); H, 5.59 (5.62); N, 9.72 (9.71).

(2) Preparation of 2,3-Dimethyl-5-benzyloxy-6-carboxy-4-pyrimidinone ethyl ester 35

To a stirred suspension of 33 (0.380 g, 1.39 mmol) in CH$_2$Cl$_2$ (20 mL) was added carbonyl diimidazole (0.230 g, 1.42 mmol). The suspension rapidly dissolved and after ~3 min the solution was diluted with ethanol (20 mL) and stirred overnight. After chromatography (SiO$_2$, 2% MeOH/CH$_2$Cl$_2$) and recrystallization from ether/hexanes, 35, (0.19 g, 45%) was afforded as a white powder. Mp: 110-111.5° C. (+)FABMS: m/z 303 ([MH]+). $^1$H NMR (CDCl$_3$, 400 MHz): δ 1.29 (t, 3H, J=7.1 Hz, ethyl-Me), 2.52 (s, 3H, 2-Me), 3.55 (s, 3H, NCH$_3$), 4.32 (q, 2H, J=7.1 Hz, OCH$_2$), 5.23 (s, 2, BnCH$_2$), 7.30-7.36, 7.45-7.47 (m, 3+2H, Ph). $^{13}$C NMR (CDCl$^{13}$, 100 MHz): δ 13.9, 23.0, 31.5, 61.8, 74.0, 128.1, 128.2, 128.4, 136.5, 141.2, 141.6, 154.1, 159.8, 164.2. Anal. Calcd (found) for C$_{16}$H$_{18}$N$_2$O$_4$: C, 63.56 (63.78); H, 6.00 (6.09); N, 9.27(9.24).

(3) Preparation of 2,3-Dimethyl-5-benzyloxy~6-carboxy-4-pyrimidinone 33 via 2,3-Dimethyl-5-benzyloxy~6-carboxy-4-pyrimidinone ethyl ester 35.

To a stirred suspension of NaH (0.745 g, 60% in oil, 18.6 mmol) in dry DMF (30 mL) was added dropwise a solution of 34 (4.88 g, 16.9 mmol) in DMF (20 mL) over ~20 min (maintaining gentle effervescence). After H$_2$ evolution had ceased, methyl iodide (1.27 mL, 20.4 mmol) was added in one portion and the reaction stirred at ambient temperature. Fine crystals deposited and after ~2 hr the reaction was complete (by TLC, silica gel, 4% MeOH/CH$_2$Cl$_2$). The excess hydride was quenched with ethanol (2 mL) and the DMF removed by rotary evaporation. Addition of water produced an oily solid which became an off-white crystalline mass upon further shaking. This solid was separated by filtration, dried briefly and then washed with hexanes (3×20 mL) to afford 3.0 g (~10 mmol) of crude 35 (>95% pure by NMR). The spectroscopic properties of this material corresponded to those of 35 synthesized in Preparation 1. This crude product was dissolved in methanol (50 mL) and KOH (0.660 g, 11.8 mmol) and stirred at room temperature. After 6 hr the hydrolysis was complete and a fine white precipitate had formed. After evaporation of the solvent under reduced pressure the residue was dissolved in water (20 mL), filtered and slowly acidified with conc. HCl. A small amount of yellowish sticky solid initially precipitated and the solution was decanted from this. Acidification continued (to pH 2) and a white solid was isolated by filtration, followed by an aqueous wash (2×10 mL) to give after drying in vacuo 2.63 g of 33 (57% from 34). This material had identical spectroscopic properties to 33 synthesized in Preparation 1. Mp. 179-180° C. Anal. Calcd (found) for C$_{14}$H$_{14}$N$_2$O$_4$: C, 61.31 (61.50); H, 5.14 (5.13); N, 10.21 (10.30).

Example 30

Ligand Syntheses from HOPY Acid (33)

(1) Preparation of Tris[(2,3-Dimethyl-5-benzyloxy-6-carboxamido-4-pyrimidinone) ethyl]amine 33A.

To a slurry of HOPY acid 33 (1.99 g, 7.26 mmol) in CH$_2$Cl$_2$ (20 mL), carbonyl diimidazole (1.25 g, 7.71 mmol) was added in 0.3 g portions over 10 min. After a further 5 min tris(2-aminoethyl)amine (0.350 g, 2.39 mmol) in CH$_2$Cl$_2$ (5 mL) was added dropwise over 5 min and the reaction stirred overnight. The CH$_2$Cl$_2$ was removed and the resultant oil shaken into ethanol (20 mL). Upon standing, a white crystalline mass separated which was filtered and washed with ethanol (5×5 mL). After drying under high vacuum at 40° C., 1.53 g (69%) of (33A) was isolated. Mp: 110-113° C. (+)FABMS: m/z 915 [MH]+. $^1$H NMR (CDCl$_3$, 400 MHz): δ 2.28 (s, 3H, 2-Me), 2.64 (t, 2H, J=5.8 Hz, cap NCH$_2$), 3.34-3.37 (m, 3+2H, NCH$_3$+CH$_2$NHCOR), 5.10 (s, 2H, BnCH$_2$), 7.27-7.35, (m, 3H, Ph), 7.50-7.52 (m, 2H, Ph), 7.79 (br t, 1H, amide NH). $^{13}$C NMR (CDCl$_3$, 100 MHz): δ 22.8, 31.9, 37.8, 53.3, 74.6, 128.3, 128.4, 129.0, 136.7, 141.1, 141.4, 153.4, 160.1, 162.9. Anal. Calcd (found) for C$_{48}$H$_{54}$N$_{10}$O$_9$.H$_2$O: C, 61.79 (61.48); H, 6.05 (5.98); N, 15.01(14.98).

(2) Preparation of N-Ethyl-2,3-dimethyl-5-benzyloxy-6-carboxamido-4-pyrimidinone 33B.

Synthesized by the method above for 33A, and isolated as a white solid in 59% yield after chromatography (SiO$_2$, 2% MeOH/CH$_2$Cl$_2$). (+)FABMS: m/z 302 [MH]$^+$. $^1$H NMR (CDCl$_3$, 400 MHz): δ 1.08 (t, 3H, J=7.3Hz, ethyl-Me), 2.49 (s, 3H, 2-Me), 3.33 (m, 2H, CH$_2$NHCOR), 3.50 (s, 3H, NMe), 5.22 (s, 2H, BnCH$_2$), 7.27-7.35, 7.38-7.40 (m, 3+2H, Ph), 7.41 (br s, 1H, amide NH). $^{13}$C NMR (CDCl$_3$, 100 MHz): δ 14.4, 23.1, 31.6, 34.3, 74.7, 128.4, 128.9, 136.3, 140.6, 141.9, 153.1, 160.3, 162.4. Anal. Calcd (found) for C$_{16}$H$_{19}$N$_3$O$_3$: C, 63.77 (63.84); H, 6.36 (6.27); N, 13.94 (14.00).

(3) Preparation of N,N-Dimethyl-2,3-Dimethyl-5-benzyloxy-6-carboxamido-4-pyrimidinone 33C Synthesized by the method above for 33A and isolated as a white solid in 68% yield after chromatography (SiO$_2$, 2% MeOH/CH$_2$Cl$_2$). (+)FABMS: m/z 302 [MH]$^+$. $^1$H NMR (CDCl$_3$, 400 MHz): δ 2.48 (s, 3H, 2-Me), 2.74 (s, 3H, amide N-Me), 2.99 (s, 3H, amide N-Me), 3.52 (s, 3H, NMe), 5.16 (s, 2H, BnCH$_2$), 7.26-7.33, 7.38-7.40 (m, 3+2H, Ph). $^{13}$C NMR (CDCl$_3$, 100 MHz): δ 23.04, 31.43, 34.30, 37.50, 74.02, 128.11, 128.27, 128.43, 136.83, 138.43, 145.98, 154.95, 159.50, 165.56. Anal. Calcd (found) for C$_{16}$H$_{19}$N$_3$O$_3$: C, 63.77 (64.08); H, 6.36 (6.35); N, 13.94 (13.90).

(4) Preparation of Tris[(2,3-Dimethyl-5-hydroxy-6-carboxamido-4-pyrimidinone)ethyl]amine 33D The benzyloxypyrimidinone 33A (1.12 g, 1.22 mmol) was dissolved in acetic acid (10 mL) and 5%Pd/C (60 mg) was added. The reaction mixture was stirred under an atmosphere of H$_2$ for 2 hrs at room temperature. The Pd/C was removed by filtration and the solution concentrated to a thick oil. Dilution with MeOH (5 mL) then water (25 mL) lead to precipitation of the product as a white powder which was dried in vacuo to afford 0.70 g of 33D (86%). Mp: 217-219° C. (melts and resolidifies), 242-244° C. (dec.). (+)FABMS: m/z 665 [MH]$^+$. $^1$H NMR (CDCl$_3$, 400 MHz): δ 1.63 (br s, 2H, water), 2.36 (br s, 3H, 2-Me), 2.81 (br t, 2H, J=6 Hz, cap NCH$_2$), 3.48 (br t+s, 2+3H, CH$_2$NHCOR+NCH$_3$), 7.83 (br, t, 1H amide NH), 11.91 (s, 1H, OH). $^{13}$C NMR (CDCl$_3$, 100 MHz): δ 22.2, 31.3, 37.1, 52.6, 125.1, 145.4, 149.0, 157.5, 168.1. Anal. Calcd (found) for C$_{27}$H$_{36}$N$_{10}$O$_9$.H$_2$O: C, 48.94 (48.69); H, 5.78 (5.89); N, 21.14 (20.78).

(5) Preparation of N-Ethyl-2,3-dimethyl-5-hydroxy-6-carboxamido-4-pyrimidinone 33E Synthesized by the method above for 33D as a white solid in 95% yield after crystallization of the crude filtrate from 2-propanol/ether. Mp: 138-139° C. (+)FABMS: m/z 212[MH]$^+$. $^1$H NMR (CDCl$_3$, 400 MHz): δ 1.24 (t, 3H, J=7.3 Hz, ethyl-Me), 2.44 (s, 3H, 2-CH$_3$), 3.43 (m, 2H, CH$_2$NCOR), 3.52 (s, 3H, NCH$_3$), 7.61 (br s, 1H, amide NH), 12.06 (s, 1H, OH). $^{13}$C NMR (CDCl$_3$, 100 MHz): δ 14.5, 22.5, 31.6, 33.9, 125.2, 146.4, 147.9, 158.6, 168.0. Anal. Calcd (found) for C$_9$H$_{13}$N$_3$O$_3$: C, 51.18 (51.40); H, 6.20 (6.10); N, 19.89 (19.79).

(6) Preparation of N,N-Dimethyl-2,3-dimethyl-5-hydroxy-6-carboxamido-4-pyrimidinone 33F Synthesized by the method above for 33D as a white solid in 92% yield after crystallization of the crude filtrate from ethanol. Mp: 203-204° C. (+)FABMS: m/z 212 [MH]$^+$. $^1$H NMR (CDCl$_3$, 400 MHz): δ 2.42 (s, 3H, 2-Me), 3.04 (br s, 3H, amide NCH$_3$), 3.22 (br s, 3H, amide NCH$_3$), 3.50 (s, 3H, NCH$_3$), 9.98 (s, 1H, OH). $^{13}$C NMR (CDCl$_3$, 100 MHz): δ 22.5, 31.6, 36.2, 38.7, 130.4, 143.2, 147.5, 159.2, 167.2. Anal. Calcd (found) for C$_9$H$_{13}$N$_3$O$_3$: C, 51.18 (51.10); H, 6.20 (6.08); N, 19.89 (19.88).

Example 31

Synthesis of Ligands with PEG Substituents (1) Preparation of TREN-bis(6-Me-1-Bn-HOPOBn$_2$)-NH$_2$ (Formula 51, Scheme 10)

A solution of 6-Me-1-Bn-3,2-HOPO-thiaz (1.125 g, 2.50 mmol) in CH$_2$Cl$_2$ (100 ml) was added dropwise, over 20 h, to a rapidly stirring solution of tris(2-aminoethylamine) (TREN, 0.201 g, 1.37 mmol) in CH$_2$Cl$_2$ (100 ml). The reaction was allowed to continue for 30 h (TLC indicated the formation of the tris-, bis-, and mono-substituted products). The solvent was evaporated and the bis-substituted product purified by flash column chromatography (silica, eluent: 99:1 CH$_2$Cl$_2$:NEt$_3$ with increasing gradient of MeOH to 5%). Evaporation of the solvents yielded a white foam (Yield: 1.02 g, 92.0%). $^1$H NMR (CDCl$_3$, 400 MHz): δ=8.02-8.08 (t, 2H, amide NH), 7.02-7.36 (m, 20H, ar. H), 6.52 (s, 1H, HOPO), 6.48 (s, 1H, HOPO), 5.33 (s, 4H, Bn-CH$_2$), 5.29 (s, 4H, Bn-CH$_2$), 3.26 (m, 4H, TREN HN-C$\underline{H}_2$), 2.32-2.47 (m, 8H, TREN CH$_2$), 2.18 (s, 3H, CH$_3$), 2.19 (s, 3H, CH$_3$).

(2) Preparation of PEG550-Cl (52A)

SOCl$_2$ (2.32 mL, 32 mmol) was added to a solution of poly(ethylene glycol) methyl ether (avg. M$_n$ ca. 550) (10.89 ml, 18 mmol) in toluene (20 ml) at 70° C. The temperature was reduced to room temperature after 2 days and stirring continued for another 2 days. The reaction mixture was then neutralized to pH 7. The solvent was evaporated and then the crude product dissolved in CH$_2$Cl$_2$. The un-dissolved salt was filtered and the organic layer was washed with water (80 ml×2). The CH$_2$Cl$_2$ was evaporated to yield a light yellow semi-solid (yield: 10.4 g, 98.0%). FAB-MS(+), m/z 579 (median) [M+1]$^+$ with 12 (CH$_2$CH$_2$O) units. The peaks are separated by 44 m/z units in the range 359-887 m/z corresponding to 7-19 (CH$_2$CH$_2$O) units.

(3) Preparation of PEG550-phthalimide (52B)

PEG550-Cl (10.40 g, 18.0 mmol) and potassium phthalimide (10.74 g, 58.0 mmol) were dissolved in dry DMF (75 ml) and heated at 130° C. for 42 h. The reaction mixture was filtered and the filtrate evaporated. The resulting yellow paste was partitioned between 1:1 CH$_2$Cl$_2$:H$_2$O (100 ml×4), the organic component extracted and dried in MgSO$_4$. Evaporation of CH$_2$Cl$_2$ yielded crude product which was purified twice by flash column chromatography (silica, eluent: CH$_2$Cl$_2$ with increasing gradient of MeOH from 0-10%). The product was isolated as a yellow oil (yield: 6.83 g, 55%). $^1$H NMR (CDCl$_3$, 400 MHz): δ=7.61-7.71 (m, 2H, ar. H), 7.51-7.57 (m, 2H, ar. H), 3.69 (t, 2H, CH$_3$O—C$\underline{H}_2$), 3.54 (t, 2H, CH$_3$OCH$_2$—C$\underline{H}_2$), 3.33-3.50 (m, large integral, PEG-CH$_2$), 3.17 (s, 3H, CH$_3$) ppm.

(4) Preparation of PEG550-NH$_3$.Cl (52C)

PEG550-phthalimide (16, 5.19 g, 7.53 mmol) and hydrazine monohydrate (1.26 g, 25.2 mmol) were refluxed for 2 h in MeOH (120 ml). The reaction mixture was cooled and the solvent evaporated resulting in a white solid residue. H$_2$O (200 ml) and concentrated HCl (10 ml) were added and the mixture refluxed for 1 h then cooled to 0° C. The phthalhydrazine white residue was removed by filtration and the filtrate evaporated yielding the product as a semi-solid. This semi-solid was washed with anhydrous ethanol and the resulting precipitate filtered. This step was repeated with MeOH and the filtrate evaporated to yield a semi-solid which was dried under vacuum (yield: 4.19 g, 99%). $^1$H NMR (D$_2$O, 400 MHz): δ=3.54-3.72 (m, 48H, CH$_2$), 3.31 (s, 3H, CH$_3$) ppm. FAB-MS (+), m/z: 516 (median); [MH]$^+$with 11 (CH$_2$CH$_2$O) units. The peaks are separated by 44 m/z units in the range 296-693 m/z, corresponding to 6-15 (CH$_2$CH$_2$O) units.

(5) Preparation of PEG550-TAM-thiaz (Formula 52, Scheme 10)

PEG550-NH$_3$.Cl (0.54 g, 98 mmol) in CH$_2$Cl$_2$ (200 ml) was added dropwise to a rapidly stirring solution of 23 (5.73 g, 987 mmol) in dry CH$_2$Cl$_2$ (250 ml) over the course of 48 hours. Triethylamine (0.09 g, 100 mmol) in CH$_2$Cl$_2$ (50 ml) was added dropwise to the yellow solution overnight. The solvent was then evaporated and the product purified by column chromatography (silica, eluent: CH$_2$Cl$_2$, with increasing gradient of MeOH from 0-9%). The product was isolated as a yellow oil (0.806 g, yield 87.0%) $^1$H NMR (CDCl$_3$ 400 MHz) δ=8.05 (s, 1H, NH), 7.89 (d, 1H, TAM H), 7.18-7.7 (m, 10H, Bn H), 7.19 (d, 1H, TAM H), 5.09 (s, 4H, Bn CH$_2$), 4.35 (t, 2H, thiaz CH$_2$), 3.46-3.64 (m, 44H, PEG CH$_2$), 3.36 (s, 3H, PEG CH$_3$), 2.90 (t, 2H, thiaz CH$_2$) ppm. FAB-MS(+), m/z 977 (medium) [M+1]$^+$ with 11 (CH$_2$CH$_2$O) units. The peaks are separated by 44 m/z units in the range 768-1153 m/z corresponding to 6-15 (CH$_2$CH$_2$O) units.

(6) Preparation of TREN-bis(6-Me-HOPO-Bn$_2$)-(Bn$_2$-TAM-PEG550) (Formula 53, Scheme 10)

51 (0.72 g, 0.89 mmol) and 52 (0.72 g, 0.73 mmol) were stirred in CH$_2$Cl$_2$ (40 ml) under N$_2$ for two days. The solution remained bright yellow and TLC indicated the reaction was incomplete. Triethylamine (0.09 g, 0.89 mmol) and dimethylaminopyridine (DMAP, 0.01 g, 0.09 mmol) were added and the reaction continued for two days. The yellow solution was then partitioned between CH$_2$Cl$_2$ and 0.5 M KOH solution. The organic component was extracted, dried with MgSO$_4$, and then filtered. The solvent was evaporated and the brown oil residue purified by flash column chromatography (silica: eluent: CH$_2$Cl$_2$ with increasing gradient of MeOH from 0-5%). The product was isolated as a light brown oil (yield: 1.08 g, 88%). $^1$H NMR (CDCl$_3$, 400 MHz): δ=8.06 (t, 1H, NH), 7.92 (t, 2H, NH), 7.80 (d, 1H, TAM CH), 7.73 (d, 1H, TAM CH), 7.62 (t, 1H, NH), 7.26-7.39 (m, 26H, aromatic H), 7.07 (m, 4H, aromatic H), 6.52 (s, 2H, HOPO H), 5.31 (s, 8H, Bn CH$_2$), 5.14 (s, 2H, TAM Bn CH$_2$), 5.08 (s, 2H, TAM Bn CH$_2$), 3.47-3.64 (m, 52H, PEG CH$_2$), 3.36 (s, 3H, PEG CH$_3$), 3.16 (m, 6H, TREN CH$_2$), 2.33 (m, 6H, TREN CH$_2$), 2.23 (s, 6H, HOPO CH$_3$) ppm.

(7) Preparation of TREN-bis(HOPO-Bn)-(TAM-PEG550) (Formula 54, Scheme 10)

TREN-bis(HOPO-Bn$_2$)-(Bn$_2$-TAM-PEG550) (53, 0.36 g, 0.22 mmol) was dissolved in acetic acid (10 ml) and then 12N HCl (10 ml) added to the solution. The solution was stirred in the dark at room temperature for 2 days. The solvents were evaporated yielding a yellow crystalline solid. MeOH (10 ml)

was added and the solvent evaporated (×3). MeOH (2 ml) was then added to the residue and the resulting solution added dropwise to a rapidly stirring solution of diethyl ether (450 ml). After stirring overnight, the mixture was filtered and the residue dried in vacuum overnight. The final product was isolated as a black, glass-like solid (yield: 0.29 g, 96%). $^1$H NMR (d$_6$-DMSO, 400 MHz): δ=9.2 (br s, 1 H, NH), 8.9 (br s, 1H, NH), 8.7 (br s, 2H, NH), 7.2-7.4 (m, 8H, Bn and TAM CH), 7.06 (d, 4H, Bn CH), 6.38 (s, 2H, HOPO H), 5.27 (s, 4H, Bn CH$_2$), 3.73 (m, 6H, TREN CH$_2$), 3.3-3.6 (m, large integral obscured by H$_2$O peak, PEG and TREN CH$_2$), 2.12 (s, 6H, HOPO CH$_3$) ppm. Anal. Calc. for 54.HCl.2H$_2$O (average of 11 ethers), (Found): C, 56.62 (56.81); H, 7.02 (7.07); N, 7.11 (6.85). FAB-MS (+), m/z: 1307 (median); [MH]$^+$with 11 (CH$_2$CH$_2$O) units. The peaks are separated by 44 m/z units in the range 1130-1483 m/z, corresponding to 7-15 (CH$_2$CH$_2$O) units.

(8) Preparation of Gd-TREN-bis(HOPO-Bn)-(TAM-PEG550) (Formula 55, Scheme 10)

TREN-bis(HOPO-Bn)-(TAM-PEG550) (54, 0.180 g, 0.131 mmol) and Gd(acac)$_3$.2H$_2$O (0.060 g, 0.126 mmol) were dissolved in MeOH (15 ml) and heated under reflux for 15 minutes. Pyridine (0.030 g, 0.382 mmol) was added and heating continued for 2 h. The solvent was evaporated and the residue purified by column chromatography (Sephadex LH-20, eluent: MeOH). The product isolated was then dissolved in MeOH (4 ml) and added dropwise to a rapidly stirring solution of diethyl ether (450 ml). The mixture was stirred overnight and then filtered. The residue was dried under vacuum overnight and isolated as a grey powder (yield: 0.135 g, 73%). Anal. Calc. for H55.3H$_2$O (average of 11 ethers), (Found): C, 51.54 (51.47); H, 6.25 (6.42); N, 6.47 (6.39). ES-MS (−), m/z: 1458 (median); [GdL]$^−$, i.e. L with 11 (CH$_2$CH$_2$O) units. The isotopic abundance of the clusters are characteristic of mononuclear Gd-containing species. The peaks are separated by 44 m/z units in the range 1284-1636 m/z, corresponding to 7-15 (CH$_2$CH$_2$O) units.

Results (1) Water Proton Relaxation

Table 3 shows some of the relaxivity properties of selected Gd complexes of the TREN-bisHOPO-TAM series.

obtained with q=1, $\tau_m$=11 ns, $\Delta H_M$=20 kJ/mol, $\Delta^2$=1.4×10$^{20}$ s$^{-1}$, $\tau_V$=24 ps. For Gd$^{III}$, the electronic relaxation rate is usually ascribed to a transient zero field splitting (ZFS) brought about by solvent collisions or molecular vibrations. $\tau_V$ is a correlation time for the modulation of this ZFS and $\Delta^2$ is the mean square of the ZFS splitting energy.

Binding to HSA

Figure 21:
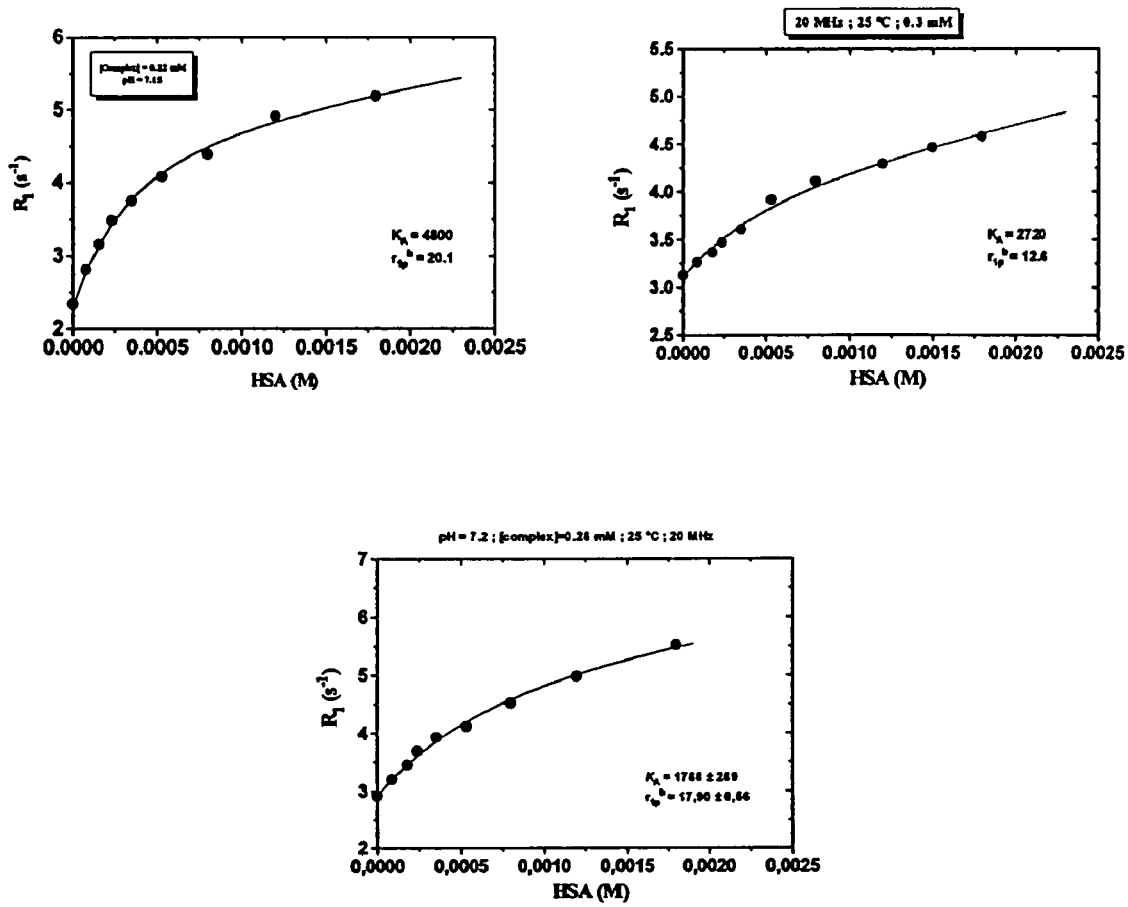
FIG. 21 displays the water proton longitudinal relaxation rate of a solution of complex as a function of HSA concentration: 55 (top left), 58 (top right), 48 (bottom)

An objective of synthesizing the Bn and MOB chelates was to investigate their interaction with HSA. The non-covalent interaction between HSA and the Gd complexes was investigated using the well-established proton relaxation enhancement (PRE) method that allows both the binding parameters (KA) and the relaxivity enhancement of the (Gd$^{3+}$ complex)-HSA adduct to be determined. In this method, the water proton longitudinal relaxation rates (R$_1$) of solutions containing the Gd complex and increasing concentrations of the serum protein are measured. The results of the PRE study of 55, 58 and 48 with HSA are shown in FIG. 21.

Example 32

Biodistribution Studies

Figure 22:
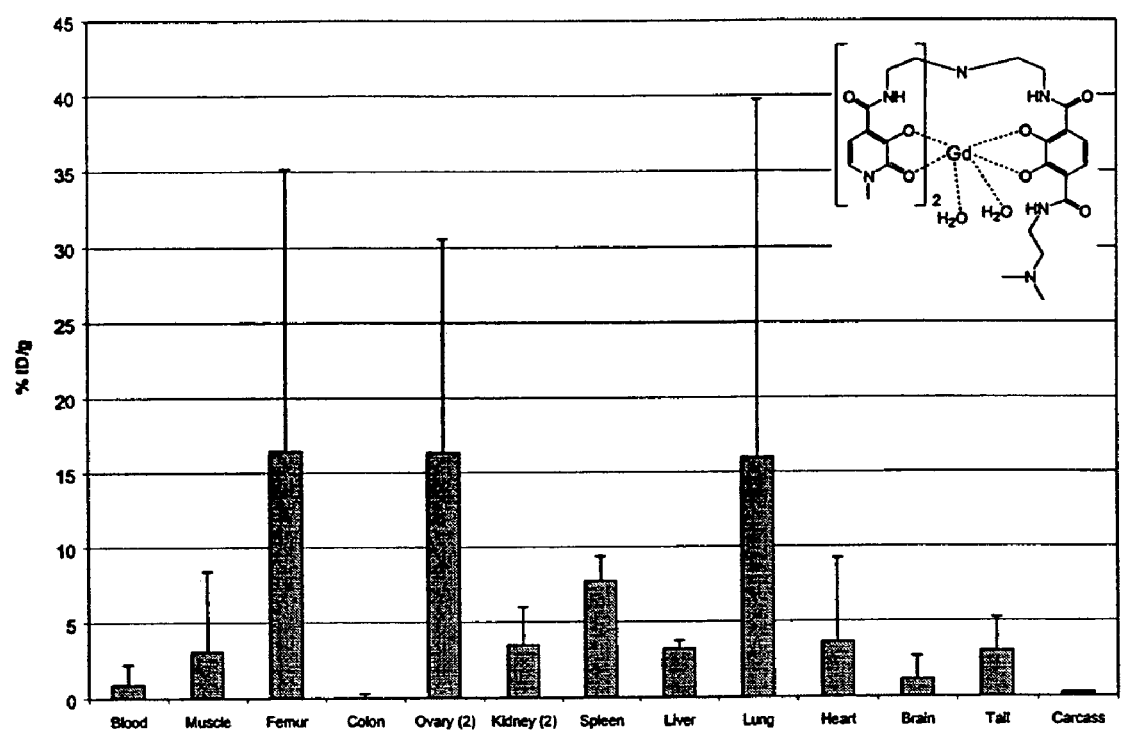
FIG. 22 displays the 24 h post injection biodistribution of $^{153}$Gd[TREN-bis(HOPO)-(TAM-DME)].

A preliminary 24 hour study of the biodistribution of $^{153}$Gd [TREN-bisHOPO-(TAM_DME)] indicated that the complex is completely cleared from mice within 24 hours of administration. Approximately 75% of the injected dose is cleared via the liver and kidneys (excreted as urine and feces). The results for the percent-injected dose per gram of tissue are shown in FIG. 22.

Example 33

Solution Thermodynamic General Methods (1) General Methods

All solutions were prepared using distilled water that was further purified by passing through a Millipore Milli-Q cartridge system (resistivity =18 MΩcm) and then degassed by boiling for at least 30 min. while bubbling with argon. Once prepared, solutions were protected from the ingress of oxygen

TABLE 3

|  | Gd-DTPA | 55 | 58 | 27E | 19 | 48 | 47 |
|---|---|---|---|---|---|---|---|
| $r_{1p}$/mM$^{-1}$s$^{-1}$ (20 MHz) | 4.3 | 8.8 | 9.2 | 9.9 | 10.4 | 8.9 | 9.1 |
| $K_A$(HSA)/M$^{-1}$ | <100 | 4242 ± 730 | 1823 ± 400 | 6860 ± 1500 | 2500 ± 400 | 959 ± 190 | 186 ± 50 |
| $r_{1p}^b$/mM$^{-1}$s$^{-1}$ (HSA) | 4.3 | 21 ± 1 | 16 ± 1 | 15.5 ± 0.3 | 22.5 ± 0.3 | 18 ± 1 | 74 ± 14 |
| $\tau_M$/ns | 303 | 11 | 8 | / | / | 10 | 31 |

Variable Temperature $^{17}$O NMR

Figure 20:
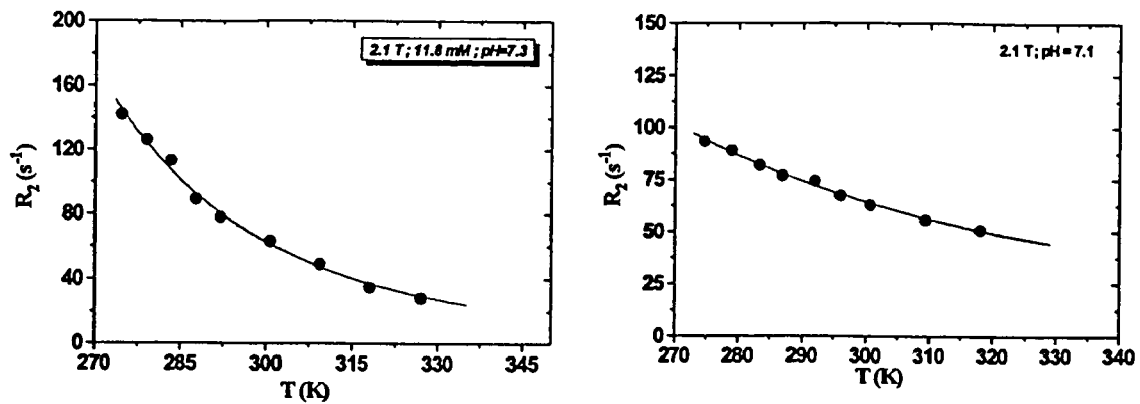
FIG. 20 displays the temperature dependence of the paramagnetic contribution ($R_2$) to the transverse $^{17}$O water relaxation rate of 55 (left) and 58 (right).

The value of $\tau_m$, was independently obtained by a variable temperature (VT) $^{17}$O NMR measurement of the water nuclear transverse relaxation rate (R$_2$). The VT $^{17}$O NMR for 55 and 58 are shown in FIG. 20. The data were measured at 2.1 T (90 MHz for the proton and 12 MHz for 17O) and pH≈7. The curve was analyzed in terms of the well established equations of Swift-Connick, rearranged in a form suitable for Gd. As an initial estimate of the values of the structural and dynamic parameters, those previously found for 47 were used in fitting the profile of 55. An excellent fit of the data was and carbon dioxide by storing under a slight positive pressure of argon, which was purified by passing through an Ascarite II (A. H. Thomas) scrubber.

A solution of 0.100 M KCl was prepared from 99.99% KCl (Fisher Scientific) and was used to maintain constant ionic strength during all titrations. Carbonate-free 0.1 M KOH was prepared from Baker Dilut-It analytic concentrated KOH and was standardized against potassium hydrogen phthalate to a phenolphthalein endpoint. Gadolinium(III) and zinc(II) solutions, each ~0.100 M in metal ion, dissolved in ~0.100 M HCl were prepared from anhydrous 99.99% chloride salts (Alpha). The metal ion content was checked by EDTA titration with Xylenol Orange as indicator using sodium acetate buffer. The proton concentration of the standard solutions was checked by titration of a known volume of metal ion solution and a slight excess of EDTA (~1.005 eq.) to the equivalence point. (Harris et al., *J. Am. Chem. Soc.*, 101:2722 (1979)). For all titrations, the observed pH was measured as $-\log[H^+]$. The glass electrode was calibrated in hydrogen ion concentration units by titrating 2.000 mL of standardized HCl diluted in 50.00 mL of 0.100 M KCl, with 4.200 mL of standardized KOH. The calibration titration data were analyzed by a non-linear least-squares program. (Martell, A. E.; Motekaitis, R. M, *Determination and Use of Stability Constants*; VCH: New York (1988)).

(2) Potentiometric pH Titrations

As previously reported, (Turowski et al., *Inorg. Chem.*, 27:474 (1988)) potentiometric titrations were performed using an automated apparatus consisting of a Accumet pH meter (models 925, 825MP or 15), a pH electrode (Orion Ross semi-micro combination, Cole Parmer semi-micro combination or Corning high performance combination electrodes), an autoburet (Metrohm 665 Dosimat or 702 SM Titrino) fitted with a 5 mL piston exchange unit and a jacketed Ar swept titration cell maintained at 25.0° C. by a Lauda K-2/R or Neslab RTE-111 constant temperature circulating bath. The electronic systems were integrated for automated collection with an IBM PC clone.

In this study, ligand and metal complex solutions were titrated from low to high pH and back again if possible. Titrations for the Zn/HOPY systems were not reversible, presumably due to the formation of mixed ML hydroxide complexes. In this case, titrations from low to high pH were carried out with differing point-by-point equilibration times (~45-120 see) to check for consistency in the determination. Formation constants calculated from the potentiometric titration data were determined with the aid of a FORTRAN non-linear least-squares refinement program (BETA 90). (Harris et al., *Am. Chem. Soc.*, 103:2667 (1981); Kappel et al., *Inorg. Chem.*, 21:3437 (1982)). Due to low solubility of the neutral $LH_3$ species of Tren-$Me_2$-5,4-HOPY, titrations could not be carried out at ligand concentrations of >0.25 mM. Although this is a low concentration for potentiometric titrations, the buffer regions corresponding to the protonation steps are around neutral pH, and so could still be determined.

(3) Spectrophotometric pH Titrations

As previously reported, (Garrett et al., *Am. Chem. Soc.*, 113:2965 (1991)) spectrophotometric titrations were carried out in a custom-built automatic titration apparatus using a HP 8450A or HP 8452A spectrophotometer and the pH monitoring equipment mentioned above for potentiometric titrations. Solutions were titrated from low to high and high to low pH to ensure equilibrium had been achieved. At least three data sets were collected and the spectra (~50-100), pH values and volumes were transferred to an IBM PC clone for analysis. Data from 230-400 nm were used in the refinement. Models used to fit the titration data and determine formation constants were refined using the factor analysis and least-squares refinement program REFSPEC. (Turowski et al., *Inorg. Chem.*, 27:474 (1988)).

(4) Relaxivity Measurements

Water proton relaxation measurements were carried out at 20 MHz with a Stelar Spinmaster Spectrometer (Mede, Pv, Italy) on 0.5-2 mM solutions of the Gd(III) complex. Spin-lattice relaxation times $T_1$ were measured by the standard inversion recovery method with typical 90° pulse width of 3.5 ms, 16 experiments of 4 scans. The reproducibility of the data is ±1%. The temperature was controlled by a Stelar VTC-91 air-flow heater equipped with copper-constantan thermo-couple (uncertainty ±0.1° C). The $1/T_1$ nuclear magnetic relaxation dispersion (NMRD) profiles of water protons were measured from 0.00024 to 1.2 T (corresponding to the range 0.01-50 MHz of proton Larmor frequencies) at 15, 25 and 39° C. using 1.5 mM solutions of the complex on the field-cycling Koenig-Brown relaxometer of the University of Torino (Italy). The temperature was controlled by circulating freon from an external bath and measured by a thermometer inserted into the freon close to the sample. The reproducibilities of the measured $T_1$ values were estimated to be ±2%. Technical details of the instrument and of the data acquisition procedure are given elsewhere. (Koenig, S. H.; Brown III, R. D., *NMR Spectroscopy of Cells and Organism*; CRC Press: Boca Raton (1987)). The sample for the NMRD profile in blood serum was prepared by dissolving a 1 mol $L^{-1}$ solution of the Gd(III) complex in a lyophilized serum of human origin (Seronorm™, Nycomed) from controlled voluntary blood donors of Scandinavian blood banks.

Variable-temperature $^{17}O$ NMR measurements were recorded on a JEOL EX-400 (9.4 T) spectrometer, equipped with a 5 mm probe, by using $D_2O$ for external lock of the magnetic field. Experimental settings were: spectral width 10000 Hz, pulse width 7 μs, acquisition time 10 ms, 1000 scans and no sample spinning. The solution used contained 17O enriched water (2.6%, Yeda, Israel). The observed transverse relaxation rates ($R^o_{2obs}$) were calculated from the linewidth of the resonance at half height.

(5) Single-Crystal X-ray Diffraction

Diffraction quality crystals of N,N-Dimethyl-6-carboxamido-2,3-dimethyl-5,4-hydroxypyrimidinone were grown by diffusion of ether into an ethanol solution at room temperature.

(6) Physical Measurements

The NMR spectra were recorded on Bruker AMX 300, AMX 400 or DRX 500 spectrometers. Chemical shifts (δ) are reported in ppm referenced to residual protio-solvent resonances. Melting points were obtained on a Buchi apparatus and are uncorrected. Electronic absorption spectra were recorded on a HP 8450A or HP 8452A UV-Vis diode array spectrophotometer with 1 cm quartz cells. Elemental analyses were performed by the Analytical Services Laboratory, College of Chemistry, University of California, Berkeley, Calif. Mass spectra (FAB+ and El) were obtained by the Mass Spectrometry Laboratory at the College of Chemistry, University of California, Berkeley, Calif.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition comprising a targeting group attached to a complex between a gadolinium (III) ion and an organic ligand, said complex comprising a structure according to Formula I:

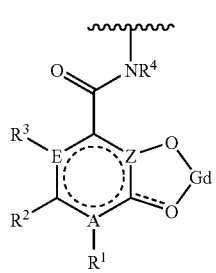

(I)

wherein $R^1$, $R^2$, and $R^3$ are members independently selected from a linking member, H, substituted or unsubstituted alkyl, substituted or unsubstituted aryl, substituted or unsubstituted heteroalkyl, hydroxy, carboxy, amide, ester, and amino groups, with the proviso that when A is nitrogen, $R^1$ is other than amino, and with the further proviso that when E is nitrogen, $R^3$ is not present;

$R^4$ is a member selected from a linking member, H, substituted or unsubstituted alkyl, substituted or unsubstituted heteroalkyl, substituted or unsubstituted aryl, hydroxy, carboxy, amide, and ester groups; and A, E and Z are members independently selected from carbon and nitrogen, said complex having a solubility in water of at least about 15 mM.

2. The composition according to claim 1, wherein at least one of $R^1$, $R^2$, $R^3$ and $R^4$ comprises a linker attaching said complex to said targeting group.

3. The composition according to claim 2 wherein said linker has the structure

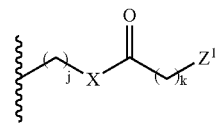

wherein $Z^1$ is a member selected from H, $CH_2$, $OR^{10}$, $SR^{10}$, $NHR^{10}$, $OCOR^{11}$, $OC(O)NHR^{11}$, $NHC(O)OR^{10}$, $OS(O)_2OR^{10}$, and $C(O)R^{11}$;

$R^{10}$ represents H, substituted or unsubstituted alkyl, or substituted or unsubstituted heteroalkyl;

$R^{11}$ is a member selected from H, $OR^{12}$, $NR^{12}NH_2$, SH, $C(O)R^{12}$, $NR^{12}H$, substituted or unsubstituted alkyl and substituted or unsubstituted heteroalkyl;

$R^{12}$ is a member selected from H, and substituted or unsubstituted alkyl;

X is a member selected from $CH_2$, O, S and $NR^{13}$;

$R^{13}$ is a member selected from H, substituted or unsubstituted alkyl and substituted or unsubstituted heteroalkyl; and j and k are each independently selected from the integers 1 to 20.

4. The composition according to claim 1, wherein said targeting group is a small molecule or a macromolecule selected from saccharides, lectins, receptors, receptor ligands, proteins, antibodies, poly(ethers), dendrimers and poly(amino acids).

5. The composition according to claim 1 wherein said complex is targeted to the blood pool.

6. The composition according to claim 5 wherein said complex binds to human serum albumin (HSA).

7. The composition according to claim 1 wherein said complex is targeted to a liver or a component of the reticuloendothelial system.

8. The composition according to claim 1 wherein said complex is selective for tumors.

9. The composition according to claim 8 wherein said targeting group is a sapphyrin.

\* \* \* \* \*

UNITED STATES PATENT AND TRADEMARK OFFICE
CERTIFICATE OF CORRECTION

PATENT NO. : 7,718,781 B2
APPLICATION NO. : 10/902772
DATED : May 18, 2010
INVENTOR(S) : Kenneth N. Raymond et al.

It is certified that error appears in the above-identified patent and that said Letters Patent is hereby corrected as shown below:

Col. 1, beginning at line 16, insert the following titled paragraph:

--STATEMENT OF GOVERNMENT RIGHTS

This invention was made with government support under AI011744, DK057814, and GM017358 awarded by the National Institutes of Health and under DE-AC03-76SF00098 awarded by the Department of Energy. The government has certain rights in the invention.--

Signed and Sealed this
First Day of January, 2013

David J. Kappos
*Director of the United States Patent and Trademark Office*